United States Patent [19]

Reiffen et al.

[11] Patent Number: 4,490,369
[45] Date of Patent: Dec. 25, 1984

[54] BENZAZEPINE DERIVATIVES, THEIR PHARMACEUTICAL COMPOSITIONS AND METHOD OF USE

[75] Inventors: Manfred Reiffen, Biberach; Joachim Heider, Warthausen; Norbert Hauel, Biberach; Volkhard Austel, Biberach; Wolfgang Eberlein, Biberach, all of Fed. Rep. of Germany; Walter Kobinger; Christian Lillie, both of Vienna, Austria; Klaus Noll, Warthausen, Fed. Rep. of Germany; Helmut Pieper, Biberach, Fed. Rep. of Germany; Gerd Krüger, Biberach, Fed. Rep. of Germany; Johannes Keck, Biberach, Fed. Rep. of Germany

[73] Assignee: Dr. Karl Thomae Gesellschaft mit beschränkter Haftung, Biberach an der Riss, Fed. Rep. of Germany

[21] Appl. No.: 547,940

[22] Filed: Nov. 2, 1983

Related U.S. Application Data

[63] Continuation-in-part of Ser. No. 523,630, Aug. 15, 1983, abandoned, which is a continuation-in-part of Ser. No. 377,599, May 12, 1982, abandoned.

[30] Foreign Application Priority Data

May 19, 1981 [DE] Fed. Rep. of Germany ....... 3119874
Nov. 18, 1982 [DE] Fed. Rep. of Germany ....... 3242599

[51] Int. Cl.[3] .................. A61K 31/55; C07D 223/16; C07D 491/55; C07D 521/00
[52] U.S. Cl. ............................ 424/244; 260/239.3 B; 260/239.3 T; 260/239 BB; 260/239 BD; 549/433
[58] Field of Search ................ 260/239.3 B, 239.3 T, 260/239 BD, 239 BB; 549/433; 424/244

[56] References Cited

U.S. PATENT DOCUMENTS

| | | | |
|---|---|---|---|
| 3,474,090 | 10/1969 | Wright | 260/239.3 B |
| 3,719,669 | 3/1973 | Shetty | 260/239 BB |
| 3,780,023 | 12/1973 | Suh | 260/239.3 B |
| 4,137,318 | 1/1979 | Eberlein | 260/239.3 B |
| 4,210,749 | 7/1980 | Shetty | 260/239.3 B |

FOREIGN PATENT DOCUMENTS 2639718 3/1978 Fed. Rep. of Germany ... 260/239.3 B

*Primary Examiner*—Robert T. Bond
*Attorney, Agent, or Firm*—Hammond & Littell, Weissenberger & Dippert

[57] ABSTRACT

Compounds of the formula

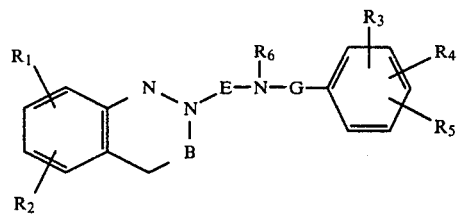

wherein
A is $-CH_2-CH_2-$, $-CH=CH-$, $-NH-CO-$, $-CH_2-CO-$ or

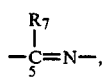

where
$R_7$ is alkyl of 1 to 3 carbon atoms, and
B is methylene, carbonyl or thiocarbonyl, or
A is $-CO-CO-$, $-N=CH-$,

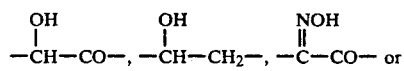

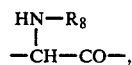

where
$R_8$ is hydrogen or alkyl of 1 to 3 carbon atoms substituted by a phenyl, methoxyphenyl or dimethoxyphenyl, and
B is methylene;
E is n-alkylene of 2 to 4 carbon atoms optionally substituted by an alkyl of 1 to 3 carbon atoms, 2-hydroxy-n-propylene, 2-hydroxy-n-butylene or 3-hydroxy-n-butylene;
G is n-alkylene of 1 to 5 carbon atoms optionally substituted by an alkyl of 1 to 3 carbon atoms, wherein one methylene group of an n-alkylene of 2 to 5 carbon atoms can be replaced by a carbonyl group, with the proviso that B represents a methylene or carbonyl group, or methylene-n-hydroxyalkylene of 1 to 4 carbon atoms, where the methylene group is attached to the nitrogen atom; and
$R_1$ to $R_5$ are simple substituents of various types;
and non-toxic, pharmacologically acceptable acid addition salts thereof. The compounds as well as their salts are useful as bradycardiacs.

14 Claims, No Drawings

BENZAZEPINE DERIVATIVES, THEIR PHARMACEUTICAL COMPOSITIONS AND METHOD OF USE

This is a continuation-in-part of copending application Ser. No. 523,630, filed Aug. 15, 1983, now abandoned which in turn is a continuation-in-part of application Ser. No. 377,599, filed May 12, 1982, now abandoned.

This invention relates to novel benzazepine derivatives and acid addition salts thereof, to methods of preparing these compounds, to pharmaceutical compositions containing them as active ingredients, and to methods using them as bradycardiacs.

THE PRIOR ART

British Patent No. 1,548,844 discloses, inter alia, the compound of the formula

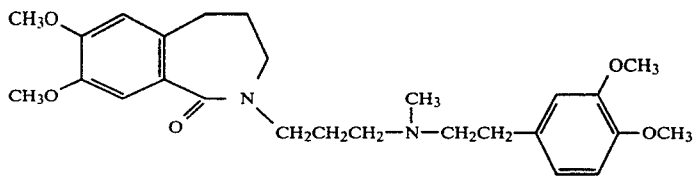

and pharmacologically acceptable acid addition salts thereof which exhibit useful pharmacodynamic properties, that is, not only mild hypotensive activity but also a selective bradycardiac activity.

THE INVENTION

More particularly, the present invention relates to a novel class of compounds represented by the formula

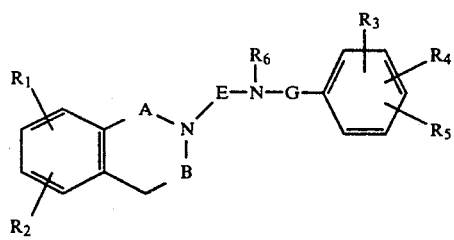

A is —CH$_2$—CH$_2$—, —CH=CH—, —NH—CO—, —CH$_2$CO— or

where R$_7$ is alkyl of 1 to 3 carbon atoms, and B is methylene, carbonyl or thiocarbonyl; or
A is —CO—CO—, —N=CH—,

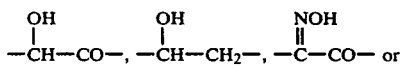

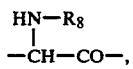

where R$_8$ is hydrogen or alkyl of 1 to 3 carbon atoms substituted by a phenyl, methoxyphenyl or dimethoxyphenyl, and B is methylene;

E is n-alkylene of 2 to 4 carbon atoms optionally substituted by an alkyl of 1 to 3 carbon atoms, 2-hydroxy-n-propylene, 2-hydroxy-n-butylene or 3-hydroxy-n-butylene;

G is n-alkylene of 1 to 5 carbon atoms optionally substituted by an alkyl of 1 to 3 carbon atoms, wherein one methylene group of an n-alkylene of 2 to 5 carbon atoms can be replaced by a carbonyl group, with the proviso that B represents a methylene or carbonyl group; or methylene-n-hydroxyalkylene of 1 to 4 carbon atoms, whereby the methylene group is attached to the nitrogen atom;

R$_1$ is hydrogen, fluorine, chlorine, bromine, trifluoromethyl, amino, hydroxy, alkyl, alkoxy, phenylalkoxy, alkylamine or dialkylamine, whereby each alkyl part may contain 1 to 3 carbon atoms;

R$_2$ is hydrogen, fluorine, chlorine, bromine, hydroxy, alkyl, alkoxy or phenylalkoxy, whereby each alkyl part may contain 1 to 3 carbon atoms; or R$_1$ and R$_2$, together with each other, are (alkylene of 1 to 2 carbon atoms) dioxy;

R$_3$ is hydrogen, fluorine, chlorine, bromine, hydroxy, cyano, nitro, trifluoromethyl, alkyl of 1 to 4 carbon atoms or alkoxy of 1 to 4 carbon atoms;

R$_4$ is hydrogen, alkyl of 1 to 3 carbon atoms, hydroxy, alkoxy of 1 to 3 carbon atoms, amino, (alkyl of 1 to 3 carbon atoms)amino, di(alkyl of 1 to 3 carbon atoms)amino, (alkanoyl of 1 to 3 carbon atoms)amino, (alkoxy of 1 to 3 carbon atoms)carbonylamino, bis[(alkoxy of 1 to 3 carbon atoms)-carbonyl]amino, (trifluoromethylmethyl)-amino or (trifluoromethyl-ethyl)-amino; or R$_3$ and R$_4$, together with each other, are (alkylene of 1 to 2 carbon atoms)dioxy;

R$_5$ is hydrogen, chlorine, bromine, cyano, hydroxy, alkyl or alkoxy, whereby each alkyl part may contain 1 to 4 carbon atoms; and R$_6$ is hydrogen, alkyl of 1 to 3 carbon atoms, phenyl(alkyl of 1 to 3 carbon atoms), alkanoyl of 1 to 3 carbon atoms, (alkoxy of 1 to 3 carbon atoms)carbonyl or alkenyl of 3 to 5 carbon atoms;

and non-toxic, pharmacologically acceptable acid addition salts thereof.

Specific examples of R$_1$, R$_2$, R$_3$, R$_4$, R$_5$, R$_6$, R$_7$, R$_8$, E and G in formula I are the following:

R$_1$: Hydrogen, methyl, ethyl, n-propyl, isopropyl, fluorine, chlorine, bromine, trifluoromethyl, hydroxy, methoxy, ethoxy, n-propoxy, isopropoxy, benzyloxy, 1-phenylethoxy, 2-phenyl-ethoxy, 3-phenyl-propoxy, amino, methylamino, ethylamino, n-propylamino, isopropylamino, dimethylamino, diethylamino, di-n-propylamino, diisopropylamino, methylethylamino, methyl-n-propylamino, methyl-isopropylamino or ethyl-n-propylamino;

R$_2$: Hydrogen, methyl, ethyl, n-propyl, isopropyl, fluorine, chlorine, bromine, hydroxy, methoxy, ethoxy, n-propoxy, isopropoxy, benzyloxy, 1-phenyl-ethoxy, 2-phenyl-ethoxy, 2-phenyl-propoxy or 3-phenyl-propoxy;

R$_3$: Hydrogen, fluorine, chlorine, bromine, methyl, ethyl, n-propyl, isopropyl, n-butyl, hydroxy, methoxy, ethoxy, n-propoxy, isopropoxy, n-butoxy, trifluoromethyl, nitro or cyano;

R$_4$: Hydrogen, methyl, ethyl, n-propyl, isopropyl, hydroxy, methoxy, ethoxy, n-propoxy, isopropoxy, amino, methylamino, ethylamino, n-propylamino, isopropylamino, dimethylamino, diethylamino, di-n-propylamino, diisopropylamino, methylethylamino, ethyl-n-propylamino, methyl-n-propylamino, methyl-isopropylamino, formylamino, acetylamino, propionylamino, methoxycarbonylamino, ethoxycarbonylamino, n-propoxycarbonylamino, isopropoxycarbonylamino, bis(ethoxycarbonyl)amino or $\beta,\beta,\beta$-trifluoroethylamino;

R$_5$: Hydrogen, chlorine, bromine, cyano, methyl, ethyl, n-propyl, isopropyl, hydroxy, methoxy, ethoxy, n-propoxy or isopropoxy;

R$_6$: Hydrogen, methyl, ethyl, n-propyl, isopropyl, benzyl, 1-phenyl-ethyl, 2-phenyl-ethyl, 3-phenyl-propyl, allyl, n-butene-2-yl, n-butene-3-yl, n-penten-2-yl, formyl, acetyl, propionyl, methoxycarbonyl, ethoxycarbonyl, n-propoxycarbonyl or isopropoxycarbonyl;

R$_7$: Methyl, ethyl, n-propyl or isopropyl;

R$_8$: Hydrogen, benzyl, 1-phenyl-ethyl, 2-phenylethyl, 3-phenyl-propyl, 2-(4-methoxyphenyl)-ethyl), 2-(3,4-dimethoxyphenyl)-ethyl, 3-(4-methoxy-phenyl)-propyl or 3-(3,4-dimethoxyphenyl)-propyl;

R$_1$ together with R$_2$ and/or R$_3$ together with R$_4$: Methylenedioxy or ethylenedioxy;

E Ethylene, n-propylene- n-butylene, 1-methyl-ethylene, 2-ethyl-ethylene, 1-propyl-ethylene, 1-methyl-n-propylene, 2-methyl-n-propylene, 1-ethyl-n-propylene, 3-ethyl-n-propylene, 2-propyl-n-propylene- 2-methyl-n-butylene, 2-hydroxy-n-propylene, 2-hydroxy-n-butylene or 3-hydroxy-n-butylene;

G: Methylene, ethylidene, propylidene, n-butylidene, 2-methyl-propylidene, ethylene, 1-methyl-ethylene, 2-ethyl-ethylene, 1-propyl-ethylene, 2-methyl-ethylene, n-propylene, n-butylene, n-pentylene, 1-methyl-n-propylene, 1-methyl-n-butylene, 1-methyl-n-pentylene, 1-ethyl-n-propylene, 2-ethyl-n-propylene, 2-methyl-n-butylene, methylenecarbonyl, ethylenecarbonyl, n-propylenecarbonyl, n-butylenecarbonyl, carbonylmethylene, carbonylethylene, carbonyl-n-propylene, carbonyl-n-butylene, methylenecarbonylmethylene, ethylenecarbonyl-methylene, 2-hydroxyethylene, 2-hydroxy-n-propylene, 3-hydroxy-n-propylene, 2-hydroxy-n-butylene, 3-hydroxy-n-butylene, 4-hydroxy-n-butylene or 2-hydroxy-n-pentylene.

A preferred subgenus is constituted by those compounds of the formula I
wherein
A is —CH$_2$CH$_2$—, —CH=CH—,

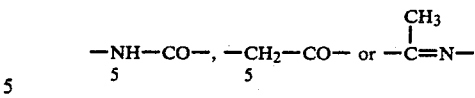

and
B is methylene, carbonyl or thiocarbonyl; or
A is —CO—CO—,

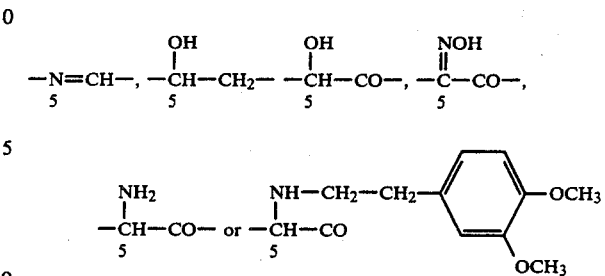

and
B is methylene;
E is ethylene, n-propylene, n-butylene, 2-methyl-n-propylene or 2-hydroxy-n-propylene;
G is methylenecarbonyl, with the proviso that B represents a methylene or carbonyl group, n-alkylene of 1 to 5 carbon atoms or methylene-n-hydroxyalkylene of 1 to 2 carbon atoms, where the methylene group is attached to the nitrogen atom;
R$_1$ is hydrogen, chlorine, bromine, trifluoromethyl, methyl, hydroxyl, benzyloxy, alkoxy of 1 to 3 carbon atoms, amino, methylamino or dimethylamino;
R$_2$ is hydrogen, chlorine, bromine, methyl, hydroxy or methoxy, or
R$_1$ and R$_2$, together with each other, are methylenedioxy;
R$_3$ is hydrogen, fluorine, chlorine, bromine, trifluoromethyl, nitro, cyano, alkyl of 1 to 4 carbon atoms or alkoxy of 1 to 4 carbon atoms;
R$_4$ is hydrogen, methoxy, amino, methylamino, dimethylamino, acetylamino, ethoxycarbonylamino, bis(ethoxycarbonyl)amino or $\beta,\beta,\beta$-trifluoroethylamino, or
R$_3$ and R$_4$, together with each other, are methylenedioxy;
R$_5$ is hydrogen, chlorine, bromine, methyl or methoxy; and
R$_6$ is hydrogen, alkyl of 1 to 3 carbon atoms, benzyl, allyl, acetyl or ethoxycarbonyl;
and non-toxic, pharmacologically acceptable acid addition salts thereof.

A particularly preferred subgenus is constituted by those compounds of the formula

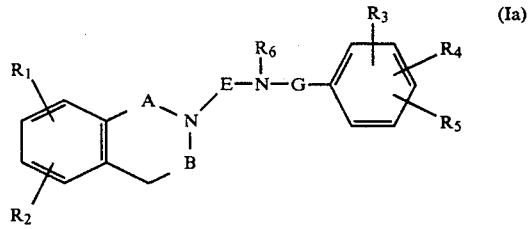

(Ia)

wherein
A is —CH$_2$—CH$_2$—, —CH=CH— or $$-\underset{|}{\overset{CH_3}{C}}=N-$$

and B is carbonyl or thiocarbonyl; or
A is —CH=CH—, $$-NH-CO-, \ -\underset{|}{\overset{OH}{C}H}-CO-$$

or —CO—CO— and
B is methylene;
E is n-propylene;
G is n-alkylene of 2 to 5 carbon atoms $$-CH_2-\underset{|}{\overset{OH}{C}H}-, \text{ or } -CH_2-CH_2-\underset{|}{\overset{OH}{C}H}-;$$

$R_1$ is hydroxy, methoxy, amino, methylamino or dimethylamino;
$R_2$ is hydrogen or methoxy, or
$R_1$ and $R_2$, together with each other, are methylenedioxy;
$R_3$ is hydrogen, fluorine, chlorine, bromine, trifluoromethyl, methyl, methoxy or nitro;
$R_4$ is hydrogen, methoxy, amino or dimethylamino, or
$R_3$ and $R_4$, together with each other, are methylenedioxy;
$R_5$ is hydrogen, chlorine or bromine; and
$R_6$ is hydrogen, methyl, ethyl, n-propyl or allyl; and non-toxic, pharmacologically acceptable acid addition salts thereof.

The compounds embraced by formula I may be prepared by the following methods:

Method A

For the preparation of a compound of the formula I wherein
A is —CH$_2$CH$_2$—, —CH=CH—,

—NH—CO—, —COCO—, —CH$_2$—CO—, $$-\underset{|}{\overset{R_7}{C}}=N- \text{ or } -N=CH-,$$

and
B is —CH$_2$— or —CO—:
By reacting a compound of the formula (II)

wherein
A' is —CH$_2$—CH$_2$—, —CH=CH—,

—NH—CO—, —COCO—, —CH$_2$—CO—, $$-\underset{|}{\overset{R_7}{C}}=N- \text{ or } -N=CH-;$$

B' is —CH$_2$— or —CO—;
$R_1'$ is hydroxyl, amino or (alkyl of 1 to 3 carbon atoms)amino, each protected by a protective group such as trimethylsilyl, acetyl, benzyl or tetrahydropyranyl, or has the meanings previously defined for $R_1$; and
$R_2'$ is hydroxyl, protected by a protective group such as trimethylsilyl, acetyl, benzyl or tetrahydropropyranyl, or has the meanings previously defined for $R_2$;

with a compound of the formula (III)

wherein
$R_6$, E and G have the meanings previously defined,
$R_3'$ and $R_5'$ are each hydroxyl protected by a protective group such as trimethylsilyl, acetyl, benzyl or tetrahydropyranyl, or have the meanings previously defined for $R_3$ and $R_5$;
$R_4'$ is hydroxy, amino or (alkyl of 1 to 3 carbon atoms)amino, each protected by a protective group such as trimethylsilyl, acetyl, benzyl or tetrahydropyranyl, or has the meanings previously defined for $R_4'$; and
Z is a nucleophilically exchangeable substituent such as halogen or a sulfonyl group, for instance chlorine, bromine or iodine, methanesulfonyloxy, p-toluenesulfonyloxy or ethoxysulfonyloxy, or with an inner quaternary salt thereof of the formula (IIIa)

wherein E, G, Z, $R_3'$, $R_4'$, $R_5'$ and $R_6'$ have the meanings previously defined, which may be present in the reaction mixture, optionally followed by removal of the protective group or groups.

The reaction is optionally carried out in a solvent or mixture of solvents, for instance in acetone, dimethylformamide, acetone/dimethylformamide, dimethylsulfoxide or chlorobenzene, and, depending on the reactivity of substituent Z, the reaction is advantageosly carried out at temperatures between 0° and 150° C., preferably at the boiling point of the solvent which is used. It is advantageous to carry out the reaction in the presence of an acid-binding agent, for example an alcoholate such as sodium methylate, an alkali metal hydroxide such as sodium hydroxide, an alkali metal carbonate such as potassium carbonate, an alkali metal amide such as sodium amide, an alkali metal hydride such as sodium hydride or a tertiary organic base such as triethylamine or pyridine, or a reaction accelerator such as potassium iodide.

The optional subsequent removal of the protective group or groups is preferably carried out by hydrolysis in an aqueous solvent, for instance in water, isopropanol/water, tetrahydrofuran/water or dioxane/water, in the presence of an acid such as hydrochloric acid or sulfuric acid or in the presence of an alkali metal base such as sodium hydroxide or potassium hydroxide at temperatures between 0° and 100° C., preferably at the boiling point of the reaction mixture. The removal of a benzyl protective group, however, may be carried out by hydrogenation, for instance with hydrogen in the presence of a catalyst such as palladium-on-charcoal, in a solvent such as methanol, ethanol, ethyl acetate or glacial acetic acid, and optionally in the presence of an acid such as hydrochloric acid at temperatures between 0° and 50° C., preferably at room temperature, and a hydrogen pressure of 1 to 7 bar, preferably 3 to 5 bar.

Method B

For the preparation of a compound of the formula I wherein $R_6$ is hydrogen, alkenyl of 3 to 5 carbon atoms, alkyl of 1 to 3 carbon atoms or phenylalkyl with 1 to 3 carbon atoms in the alkyl moiety:

By reacting a compound of the formula

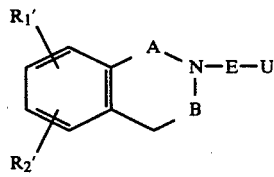
(IV)

with a compound of the formula

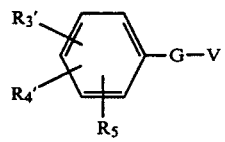
(V)

in which A, B, E, G and $R_1'$ to $R_5'$ have the meanings previously defined, one of the radicals U and V is $R_6'$—NH— where $R_6'$ is hydrogen, alkenyl of 3 to 5 carbon atoms, alkyl of 1 to 3 carbon atoms or phenylalkyl with 1 to 3 carbon atoms in the alkyl moiety, and the other of radicals U and V is a nucleophilically exchangeable group such as a halogen atom or a sulfonyloxy group, for example chlorine, bromine, iodine, methanesulfonyloxy, p-toluenesulfonyloxy or ethoxysulfonyloxy, or the radical U, together with the hydrogen atom in the β-position of the radical E is an oxygen atom and V is $R_6'$—NH—, where $R_6'$ has the meanings defined above, optionally followed by removal of the protective radical or radicals.

The reaction is advantageously carried out in a solvent or mixture of solvents such as acetone, diethyl ether, methylformamide, dimethylformamide dimethylsulfoxide, benzene, chlorobenzene, tetrahydrofurane, benzene/tetrahydrofuran, dioxane or in an excess of the compounds of the formulas IV and/or V and optionally in the presence of an acid-binding agent, for instance an alcoholate such as potassium tert.butylate, an alkali metal hydroxide such as sodium or potassium hydroxide, an alkali metal carbonate such as potassium carbonate, an alkali metal amide such as sodium amide, an alkali metal hydride such as sodium hydride, a tertiary organic base such as triethylamine or pyridine, where the latter may simultaneously serve as solvents, or a reaction accelerator such as potassium iodide, and, depending on the reactivity of the nucleophilically exchangeable group, the reaction is advantageously carried out at temperatures between 0° and 150° C., preferably at temperatures between 50° and 120° C., for example at the boiling point of the solvent which is used. However, the reaction may also be carried out without a solvent. It is, however, particularly advantageous to carry out the reaction in the presence of a tertiary organic base or an excess of the particular amine of the formula V which is used.

The optional subsequent removal of the protective radical or radicals is preferably carried out by hydrolysis in an aqueous solvent, for instance in water, isopropanol/water, tetrahydrofuran/water of dioxane/water, in the presence of an acid such as hydrochloric acid or sulfuric acid or in the presence of an alkali metal base such as sodium hydroxide or potassium hydroxide at temperatures between 0° and 100° C., preferably at the boiling point of the reaction mixture. The removal of a benzyl protective radical, however, may also be carried out by hydrogenation, for example with hyrogen in the presence of a catalyst such as palladium-on-charcoal, in a solvent such as methanol, ethanol, ethyl acetate or glacial acetic acid, and optionally in the presence of an acid such as hydrochloric acid, at temperatures between 0° and 50° C., preferaboy at room temperature, and a hydrogen pressure of 1 to 7 bar, preferably 3 to 5 bar.

Method C

For the preparation of a compound of the formula I, wherein $R_6$ is hydrogen, alkenyl of 3 to 5 carbon atoms, alkyl of 1 to 3 carbon atoms or phenylalkyl with 1 to 3 carbon atoms in the alkyl moiety, and A is other than

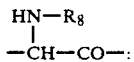

By reacting a compound of the formula

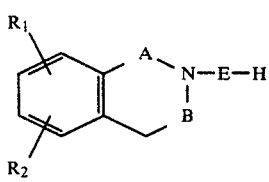
(VI)

wherein A, B, E, $R_1$ and $R_2$ have the meanings previously defined, where, however, in the radical E two hydrogen atoms of a —$CH_2$— or $CH_3$-group are replaced by an oxygen atom, with an amine of the formula

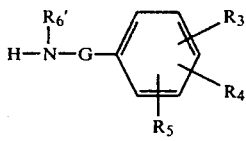

wherein G and R₃ to R₅ have the meanings previously defined, and R₆' is hydrogen, alkenyl of 3 to 5 carbon atoms, alkyl of 1 to 3 carbon atoms or phenylalkyl with 1 to 3 carbon atoms in the alkyl moiety, in the presence of a reducing agent.

The reaction is advantageously carried out in a suitable solvent or mixture of solvents such as methanol, ethanol, ethanol/ethyl acetate or dioxane, at temperatures between 0° and 100° C., preferably between 20° and 80° C.

It is particularly advantageous to carry out the reductive amination in the presence of a complex metal hydride such as lithium or sodium cyanoborohydride, preferably at a pH of 6 to 7, and at room temperature, or for preparation of a compound of the formula I wherein R₆ is hydrogen, in the presence of a hydrogenation catalyst, for example with hydrogen in the presence of palladium-on-charcoal at a hydrogen pressure of 5 bar. Optionally present benzyl groups are simultaneously split off by hydrogenation, and/or double bonds are hydrogenated.

Method D

For the preparation of a compound of the formula I wherein R₆ is hydrogen, alkenyl of 3 to 5 carbon atoms, alkyl of 1 to 3 carbon atoms or phenylalkyl with 1 to 3 carbon atoms in the alkyl moiety, and A is other than

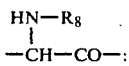

By reacting a compound of the formula

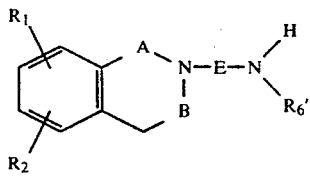

wherein A, B, E, R₁ and R₂ have the meanings previously defined, and R₆' is hydrogen, alkenyl of 3 to 5 carbon atoms, alkyl of 1 to 3 carbon atoms or phenylalkyl with 1 to 3 carbon atoms in the alkyl moiety, with a compound of the formula

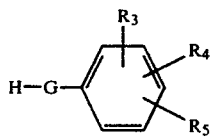

wherein G and R₃ and R₅ have the meanings previously defined, where, however, in the radical G two hydrogen atoms of a —CH₂— or CH₃-group are replaced by an oxygen atom, in the presence of a reducing agent.

The reaction is advantageously carried out in a suitabe solvent or mixture of solvents such as methanol, ethanol, ethanol/ethyl acetate or dioxane at temperatures between 0° and 100° C., preferably between 20° and 80° C. It is particularly advantageous to carry out the reductive amination in the presence of a complex metal hydride such as lithium or sodium cyanoborohydride, preferably at a pH of 6 to 7, and at room temperature, or for the preparation of a compond of the formula I wherein R₆ is hydrogen, in the presence of a hydrogenation catalyst, for example with hydrogen in the presence of palladium-on-charcoal at a hydrogen pressure of 5 bar. Optionally present benzyl groups are simultaneously split off by hydrogenation and/or double bonds are hydrogenated.

Method E

For the preparation of a compound of the formula I wherein A is —NH—CO—, E is n-alkylene of 2 to 4 carbon atoms optionally substituted by alkyl of 1 to 3 carbon atoms, and R₆ is other than hydrogen:

By reacting a compound of the formula

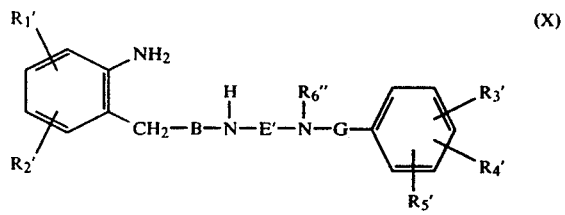

wherein B and G have the meanings previously defined, E' is n-alkylene of 2 to 4 carbon atoms optionally substituted by alkyl of 1 to 3 carbon atoms, R₁' and R₅' have the meanings as previously defined, and R₆'' has the meanings defined for R₆ with the exception of hydrogen or is a protective group for an amino group, with a carbonic acid derivative of the formula $$W-CO-W \qquad (XI)$$

wherein each W, which may be the same as or different from the other, is a nucleophilically exchangeable group such as a chlorine or bromine atom, an alkoxy group of 1 to 3 carbon atoms optionally substituted by halogen atoms or an imidazolyl-(2)-group, optionally followed by removal of the protective radical or radicals.

The reaction is advantageously carried out in a solvent or mixture of solvents such as methylene chloride, carbon tetrachloride, benzene, tetrahydrofuran, benzene/tetrahydrofuran, dioxane or acetonitrile, at temperatures betweeon 0° and 150° C., preferably at the boiling point of the solvent which is used, for instance at temperatures between 40° and 100° C., and optionally in the presence of an acidbinding agent such as potassium carbonate, sodium hydroxide, potassium hydroxide, pyridine or triethylamine, where the latter two may simultaneously serve as solvents. However, the reaction may also be carried out without a solvent. If in a compound of the formula XI at least one of the radicals W is an alkoxy group of 1 to 3 carbon atoms, the reaction is preferably carried out in an excess of the ester as the solvent medium.

The optional subsequent removal of the protective radical or radicals is preferably crrried out by hydrolysis in an aqueous solvent, for example in water, isopropanol/water, tetrahydrofuran/water or dioxane/- water, in the presence of an acid such as hydrochloric acid or sulfuric acid or in the presence of an alkali metal base such as sodium hydroxide or potassium hyroxide, at temperatures between 0° and 100° C., preferably at the boiling point of the reaction mixture. The removal of a protective benzyl radical, however, may also be carried out by hydrogenation, for instance with hydrogen in the presence of a catalyst such as palladium-on-charcoal, in a solvent such as methanol, ethanol, ethyl acetate or glacial acetic acid, optionally in the presence of an acid such as hydrochloric acid, at temperatures between 0° and 50° C., preferably at room temperature, and a hydrogen pressure of 1 to 7 bar, preferably 3 to 5 bar.

Method F

For the preparation of a compound of the formula I wherein A is —CH₂—CH₂—, B is methylene or carbonyl, R₁ and R₂ are other than benzyl, R₃ or R₄ is other than nitro, and R₆ is other than benzyl or alkenyl of 3 to 5 carbon atoms:

By hydrogenating a compound of the formula

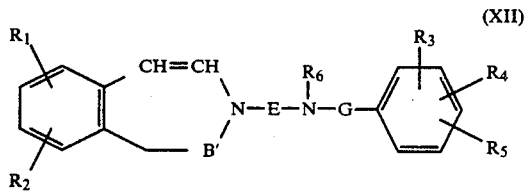

(XII)

wherein R₁ to R₆, E and G have the meanings previously defined, where R₃ and R₄ is other than nitro when R₅ is amino, and B' is methylene or carbonyl.

The hydrogenation is carried out in a solvent or mixture of solvents such as methanol, ethanol, ethyl acetate or glacial acetic acid with catalytically activated hydrogen, for instance with hydrogen in the presence of platinum or palladium-on-charcoal, at a hydrogen pressure of 1 to 7 bar, preferably 3 to 5 bar, and at temperatures between 0° and 75° C., preferably between 20° an 50° C. If in a compound of formula XII, R₆ is benzyl, this group is simultaneously replaced during the hydrogenation of a hydrogen atom, or if R₁ and/or R₂ are benzyloxy, these radicals are each converted into hyroxyl during the hydrogenation.

Method G

For the preparation of a compound of the formula I wherein A is —CH₂CH₂—, —CH=CH=,

—NH—CO—, —CH₂CO—, —N=CH—,
    5              5           5

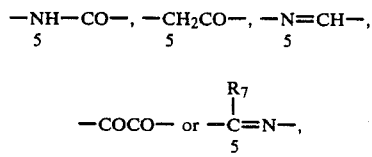

but at least one of the radicals R₁ to R₅ is alkoxy, alkylamino or dialkylamino, or R₆ is alkyl or alkenyl: By reacting a compound of the formula

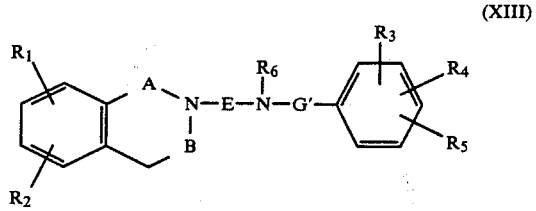

(XIII)

wherein R₁ to R₆, B and E have the meanings previously defined, but at least one of the radicals R₁ to R₅ must be hydroxyl or R₁ or R₄ is amino or alkylamino of 1 to 3 carbon atoms, or R₆ is hydrogen, A is —CH₂—CH₂—, —CH=CH—,

—NH—CO—, —CH₂CO—, —N=CH—,
    5           5

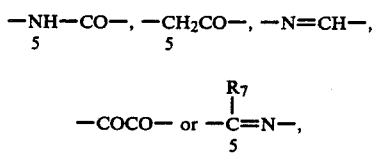

and G' is n-alkylene of 1 to 5 carbon atoms optionally substituted by an alkyl of 1 to 3 carbon atoms, where one methylene group of an n-alkylene of 2 to 5 carbon atoms can be replaced by a carbonyl group, with a compound of the formula

R₉ - X     (XIV)

wherein R₉ is alkyl of 1 to 3 carbon atoms, or also alkenyl of 3 to 5 carbon atoms when R₆ is hydrogen, or also alkyl of 1 to 3 carbon atoms substituted by phenyl when R₁ or R₂ is hydroxyl an/or R₆ is hydrogen, and X is a nucleophilically exchangeable group such as a halogen atom or a sulfonyloxy group, for instance chlorine, bromine, iodine, methanesulfonyloxy, p-toluenesulfonyloxy or methoxysulfonyloxy, or, when at least one of radicals R₁ to R₅ is hydroxyl, X together with a hydrogen atom in α-position of the radical R₉ is a diazo group, or also, when R₆ is hydrogen or R₅ is amino or alkylamino, represents an oxygen atom.

The reaction is advantageously carried out in a solvent or mixture of solvents such as diethyl ether, methanol, acetone, tetrahydrofuran, dioxane, acetonitrile, pyridine or dimethylformamide, optionally in the presence of a base such as potassium carbonate, potassium hyroxide, potassium tert. butylate or sodium hydride, at temperatures between 0° and 150° C., preferably between 20° and 120° C.

When X is a nucleophilically exchangeable group, the reaction is preferbly carried out with an alkylating agent such as methyl iodide, dimethyl sulfate, ethyl iodide, diethyl sulfate, propyl bromide, allyl bromide, benzyl chloride, phenylethyl bromide or p-toluenesulfonic acid isopropyl ester in the presence of an acid-binding agent at temperatures between 20° and 80° C. The reaction may, however, also be carried out without a solvent.

When X, together with the hydrogen atom in α-position of the redical R₉, forms a diazo group, in order to alkylate a hydroxyl group, the reaction is preferably carried out with diazomethane or diazoethane at temperatures between 0° and 30° C.; or when X is an oxygen atom, in order to alkylate the nitrogen atom, the reaction is carried out in the presence of a reducing agent at temperatures between 0° and 120° C., for example with formic acid at temperatres between 80° and 100° C. or with sodium cyanoborohydride at room temperatures and a pH of 6 to 7.

Method H

For the preparation of a comound of the formula I wherein A is other than —CH=CH—, $R_5$ is chlorine or bromine, and $R_4$ is amino ro alkylamino:

By halogenating a compound of the formula

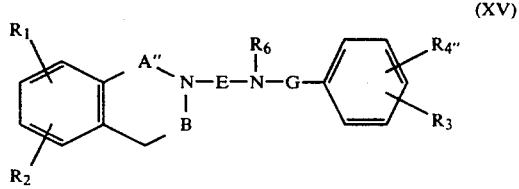

(XV)

wherein $R_1$, $R_2$, $R_3$, $R_5$, B, E and G have the meanings previously defined, A" has the meanings defined for A with the exception of —CH=CH—, and $R_4$" is amino or alkylamino of 1 to 3 carbon atoms.

The reaction is carried out with a halogenating agent, for example with chlorine, bromine, tribromophenol-bromine of phenyl iodide dichloride, preferably in a solvent or mixture of solvents, for instance in 50 to 100% acetic acid or in tetrahydrofuran in the presence of a tertiary organic base, optionally in the presence of a heavy metal compound such as mercuric oxide, and advantageously at temperatures between 0° and 50° C. Per mol of a compound of the formula XV, which may be used as the base or also as a slat such as the mono-, di- or trihydrochloride, 1 or 2 mols of the halogenating agent or a slight excess thereover are used. If a corresponding hydrogen halide salt is formed during the reaction, this salt may be directly isolated as such or, if desired, it may be further purified by way of the base.

Method I

For the preparation of a compound of the formula I wherein A is —CO—CO—, E is n-alkylene of 2 to 4 carbon atoms optionally substituted by alkyl of 1 to 3 carbon atoms, B is —CH$_2$—, and G' is n-alkylene of 1 to 5 carbon atoms optionally substituted by an alkyl of 1 to 3 carbon atoms, where one methylene of an n-alkylene of 2 to 5 carbon atoms may be replaced by a carbonyl group.

By oxidizing a compound of the formula

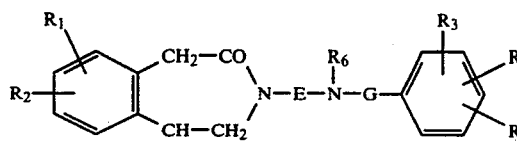

(XVI)

wherein $R_1$ to $R_6$, E and G have the meanings previously efined.

The oxidation is preferably carried out with an oxidizing agent such as potassium permanganate, selenium dioxide or sodium dichromate, in a suitable solvent or mixture of solvents such as water, water/dioxane, glacial acetic acid, water/acetic acid or acetic anhydride, and at temperatures between 0° and 100° C., preferably between 20° and 80° C.

Method K

For the preparation of a compound of the formula I wherein B is —CS, and G is n-alkylene of 1 to 5 carbon atoms optionally substituted by an alkyl group with 1 to 3 carbon atoms, or a methylene-n-hydroxy-alkylene group of 1 to 4 carbon atoms in the alkylene moiety:

By reacting a compound of the general formula

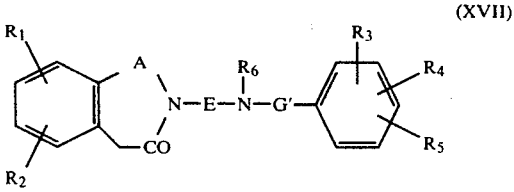

(XVII)

wherein $R_1$ to $R_6$, A and E have the meanings previously defined and G' is n-alkylene of 1 to 5 carbon atoms optionally substituted by alkyl of 1 to 3 carbon atoms, or methylene-n-hydroxyalkylene of 1 to 4 carbon atoms in the alkylene moiety, with a sulfur-introducing agent.

The reaction is carried out with a sulfur-introducing agent such as phosphorus pentasulfide or 2,4-bis(4-methoxyphenyl)-1,3-dithia-2,4-diphosphetane-2,4-disulfide, advantageously in a solvent such as toluene or xylene at temperatures of between 50° and 150° C., for instance at the boiling point of the reaction mixture.

Method L

For the preparation of a compound of the formula I wherein A is

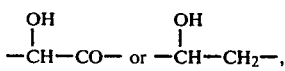

and G is n-alkylene of 1 to 5 carbon atoms optionally substituted by alkyl of 1 to 3 carbon atoms, or methylene-n-hydroxy-alkylene of 1 to 4 carbon atoms in the alkylene moiety:

By reducing a compound of the formula

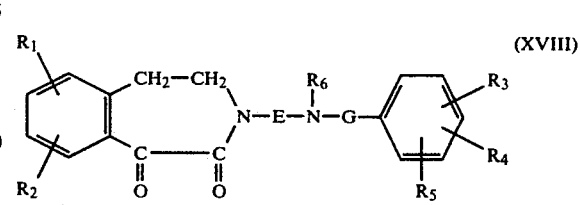

(XVIII)

wherein $R_1$ to $R_6$, E and G have the meanings previously defined.

The reaction is carried out in the presence of a suitable reducing agent such as metal hydride, for example sodium borohydride or lithium aluminum hydride, in a suitable solvent such as water/methanol, methanol/ether, tetrahydrofuran, dioxane or ether/tetrahydrofuran and at temperatures between 0° and 80° C., but preferably between 15° and 40° C. In the reaction, any —CO— group present in the G moiety is also reduced to the —CHOH— group.

Method M

For the preparation of a compound of formula I wherein A is

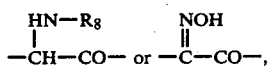

and G is n-alkylene of 1 to 5 carbon atoms optionally substituted by alkyl of 1 to 3 carbon atoms, or methylene-n-hydroxyalkylene of 1 to 4 carbon atoms in the alkylene moiety:

By reacting a compound of the formula

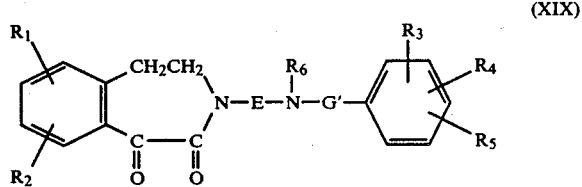

(XIX)

wherein $R_1$ to $R_6$ and E have the meanings previously defined, an G' is n-alkylene of 1 to 5 carbon atoms optionally substituted by alkyl of 1 to 3 carbon atoms, or methylene-n-hydroxyalkylene of 1 1 to 4 carbon atoms in the alkylene moiety, with a compound of the formula

(XX)

wherein $R_9$ is hydroxyl or has the meanings previously defined for $R_8$, optionally followed by reduction.

The reaction is advantageously effected in a solvent such as ethanol, dioxane of glycol or with the reactants in the molten state, at elevated temperatures, for instance at temperatures between 50° and 175° C. The optional subsequent reduction is effected with a reducing agent such as a complex metal hydride, for example lithium aluminum hydride, with catalytically activated hydrogen, for example with hydrogen in the presence of a hydrogenation catalyst such as platinum or pallladium-on-charcoal under a hydrogen pressure of 1 to 7 bar, but preferably 3 to 5 bar, or with hydrazine/Raney nickel in a suitabe solvent such as methanol, ethanol, ethyl acetate or glacial acetic acid, at temperatures between 0° and 100° C., preferably between 20° and 50° C.

Method N

For the preparation of a compond of the formula I wherein A is —N═CH— group and $R_6$ is alkyl of 1 to 3 carbon atoms or of 3 to 5 carbon atoms:

By reating a compound of the formula

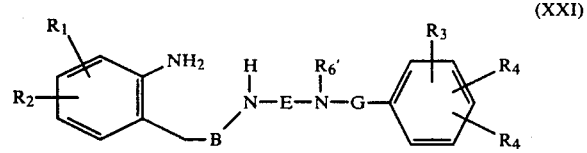

(XXI)

wherein $R_1$ to $R_5$, B, E and G have the meanings previously defined an $R_6'$ is alkyl of 1 to 3 carbon atoms or alkenyl of 3 to 5 carbon atoms, with an orthoformic acid ester.

The reaction is preferably carried out in a solvent such as ethanol, toluene or dimethoxyethane, or in an excess of the orthoester, at temperatures between 100° and 200° C.

It may also be advantageous for any —NH$_2$ or —NH— groups present to be protected by protective groups, such as acetyl, benzoyl, ethoxycarbonyl or benzyl, during the reaction.

The protective groups used during the reaction are subsequently split off again; for instance acyl groups are preferably removed by hydrolysis in the presence of an acid or base, while benzyl groups are preferably removed by hydrogenolysis, for example with hydrogen in the presence of a hydrogenation catalyst such as palladium-on-charcoal or platinum.

Method O

For the preparation of a compound of the formula I wherein A is other than —CO—CO—, and G is methylene-n-hydroxyalkylene:

By reducing a compound of the formula

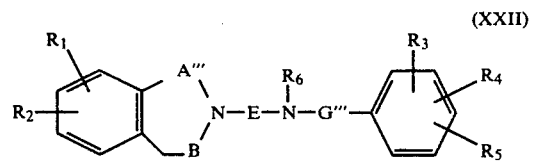

(XXII)

wherein $R_1$ to $R_6$, B and E have the meanings defined, A''' has the meanings previously defined for A except —CO—CO—, and G''' is methylene-n-alkylene, where the alkylene moiety contains 1 to 4 carbon atoms and a methylene group of the alkylene moiety is replaced by a carbonyl group.

The reduction is preferably carried out with a metal hydride such as sodium borohydride, in a suitable solvent such as ethanol, ethanol/water, methanol or isopropanol and at temperatures between 0° and 50° C., preferably between 10° and 25° C.

Method P

For the preparation of a compound of the formula I wherein $R_3$ is nitro, and $R_4$ is amino:

By hydrolysis of a compound of the formula

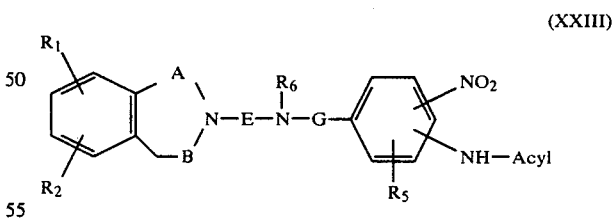

(XXIII)

wherein $R_1$, $R_2$, $R_5$, $R_6$, A, B, E and G have the meanings previously defined, and Acyl is carboxylic acyl such as acetyl, ethoxycarbonyl or benzoyl.

The acyl group is preferably split off by hydrolysis in an aqueous solvent, for instance in water, isopropanol/water, tetrahydrofuran/water or dioxane/water, in the presence of an acid such as hydrochloric or sulfuric acid, or in the presence of an alkali metal base such as sodium hydroxide or potassium hydroxide, at temperatures between 0° and 100° C., preferably at the boiling point of the reaction mixture. However, the reaction is preferably carried out in the presence of an alkanolic acid, for instance with methanolic or ethanolic hydrochloric acid.

Method Q

For the preparation of a compound of the formula I wherein A is —CH$_2$—CO—, and G is n-alkylene of 1 to 5 carbon atoms optionally substituted by alkyl of 1 to 3 carbon atoms wherein a methylene group may be replaced by a carbonyl group:

By oxidizing a benzapine of the formula

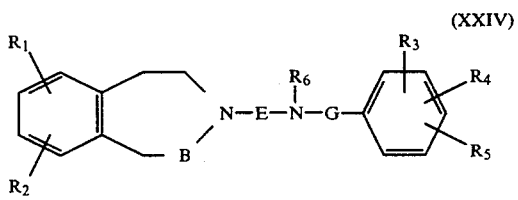

(XXIV)

wherein R$_1$ to R$_6$, B, E, and G have the meanings previously defined.

The oxidation is effected with ruthenium tetroxide in a suitable solvent or mixture of solvents such as chloroform/water, methylene chloride/water or carbon tetrachloride/water, and at temperatures between 0° and 100° C., preferably between 20° and 50° C. However, the reaction is preferably carried out in a two-phase system such as methylene chloride/water, chloroform/water or carbon tetrachloride/water with a catalytic quantity of ruthenium dioxide, and in the presence of a suitable oxidizing agent such as sodium periodate which produces ruthenium tetroxide in situ.

Method R

For the preparation of a compound of the formula I wherein R$_1$ is in the 7-position, A is —CH$_2$—CH$_2$—, and B is —CO—:

By cyclizing a compound of the formula

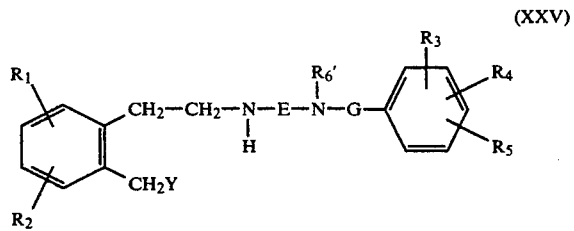

(XXV)

wherein R$_1$ to R$_5$, G and E have the meanings previously defined, R$_6'$ is alkyl of 1 to 3 carbon atoms or alkenyl of 3 to 5 carbon atoms, and Y is a group suitable for cyclization.

Y may, for example, be carboxyl or cyano, an ester group such as methoxycarbonyl, ethoxycarbonyl, n-propoxycarbonyl or benzyloxycarbonyl, a thioester group such as ethylthiocarbonyl, phenylthiocarbonyl or pyridylthiocarbonyl, an acyloxycarbonyl group such as acetoxycarbonyl or trifluoroacetylcarbonyl, or an amide group such as aminocarbonyl, methylaminocarbonyl, dimethylaminocarbonyl or phenylaminocarbonyl.

The reaction is optionally carried out in the presence of a suitable condensation agent and optionally in a pressure vessel, in a solvent such as xylene, dimethylglycol ether, tetralin or sulfolane at elevated temperatures, for instance at temperatures between 100° and 250° C., preferably between 140° and 180° C. However, the reaction may also be carried out without a solvent.

Suitable condensation agents include, for example N'-dicyclohexylcarbodiimide, thionyl chloride, phosphates, such as diethyl chlorophosphonate or bis(0-nitrophenyl)- phenylphosphonate, phosphoranes such as (2,2,2-trifluoroethoxy)-triphenylphosphorane, N-alkyl-pyridinium salts such as N-methyl-2-chloropyridinium iodide or N-methyl-2-fluoropyridiniumtosylate, N,N'-dicyclohexyl-carbodiimide/4-dimethylaminopyridine, chlorosulfonyl isocyanate or N,N'-carbonyldiimidazole.

It may also be advantageous for any HO, NH or NH$_2$ groups present to be protected by means of protective groups, such as acetyl, benzoyl, ethoxy-carbonyl or benzyl, during the reaction.

If Y in a compound of the formula XXV represents a cyano or amide group, the reaction is preferably effected so that a corresponding compound is converted by alkaline or acidic hydrolysis, for example by means of methanol/hydrochloric acid or ethanol/sodium hydroxide at the boiling point of the reaction mixture, into a corresponding carboxy compound which is subsequently cyclized.

Any protective groups used during the reaction are subsequently split off again; for instance, acyl groups are preferably removed by hydrolysis in the presence of an acid or base, while benzyl groups are preferably removed by hydrogenolysis, for example, with hydrogen in the presence of a hydrogenation catalyst such as palladium-on-charcoal or platinum.

If the end product of the above-described methods is a compound of the formula I wherein B is carbonyl, this compound can be converted by reduction into a corresponding compound of the formula I wherein B is methylene; and/or If the end product is a compound of the formula I wherein A is other than a —CH=CH— or $$\begin{array}{c} R_7 \\ | \\ -C=N- \end{array}$$

and R$_6$ is benzyl or 1-phenylethyl, this compound can be converted by catalytic hydrogenation into a corresponding compound of the formula I wherein R$_6$ is hydrogen; and/or If the end product is a compound of the formula I wherein R$_3$ or R$_4$ is nitro, this compound can be converted by reduction into a corresponding compound of the formula I wherein R$_5$ is amino; and/or If the end product is a compound of the formula I wherein R$_6$ is hydrogen and/or R$_5$ is amino, this compound can be converted by acylation into a corresponding compound of the formula I wherein R$_6$ is alkanoyl or alkoxycarbonyl and/or R$_5$ is alkanoylamino, alkoxycarbonylamino or bis-(alkoxycarbonyl)amino, where each alkyl moiety contains from 1 to 3 carbon atoms; and/or If the end product is a compound of the formula I wherein R$_5$ is alkanoylamino, this compound can be converted by hydrolysis into a corresponding compound of the formula I, wherein R$_5$ is amino; and/or If the end product is a compound of the formula I wherein R$_5$ is amino, R$_6$ is other than hydrogen, and R$_3$ and R$_4$ are other than cyano, this compound can be converted by way of a corresponding diazonium salt into a corresponding compound of the formula I wherein R₅ is hydrogen, a hydroxyl or alkoxy, or R₅ is a hydrogen and R₃ is halogen or cyano.

The aforementioned reduction is preferably carried out with a metal hydride such as lithium aluminum hydride or diborane, in a solvent such as diethyl ether, tetrahydrofuran or dioxane, and at temperatures between 0° and 100° C., preferably between 30° and 85° C.

The aforementioned reduction or catalytical hydrogenation is carried out in a solvent such as methanol, ethanol, ethyl acetate or glacial acetic acid with hydrogen in the presence of a catalyst such as platinum or palladium-on-charcoal, at a hydrogen pressure of 1 to 7 bar, preferably at 3 to 5 bar, and at temperatures between 0° and 75° C., preferably between 20° and 50° C. Any present nitro and cyano groups are simultaneously also reduced.

The aforementioned acylation is carried out, for example, with acetyl chloride, acetic anhydride, propionic acid anhydride or a corresponding chloroformate such as ethyl chloroformate, which simultaneously may serve as the solvent, optionally in a solvent such as water/tetrahydrofuran, diethyl ether, tetrahydrofuran or methylene chloride, optionally in the presence of a base such as triethylamine or pyridine, where a tertiary organic base simultaneously may serve as the solvent, at temperatures between 0° and 100° C., preferably at room temperature. The reaction may, however, also be carried out without a solvent.

The aforementioned reaction by way of a diazonium salt, such as the fluoroborate, the hydrosulfate in sulfuric acid, the hydrochloride or the hydroiodide, is carried out, if necessary, in the presence of copper or a corresponding copper-(I)-salt such as copper-(I)-chloride/hydrochloric acid, copper-(I)-bromide/hydrobromic acid or trisodiumcopper-(I)-tetracyanide at pH 7 at slightly elevated temperatures, for instance at temperatures between 15° C. and 100° C.; the subsequent reaction with hypophosphorous acid is preferably carried out at −5° C. to 0° C. The diazonium salt necessary for this reaction is prepared in a suitable solvent, for instance in water/hydrochloric acid, methanol/hydrochloric acid, ethanol/hydrochloric acid or dioxane/hydrochloric acid, by diazotization of a corresponding amino compound with a nitrite such as sodium nitrite or an ester of nitrous acid, at low temperatures, for example at temperatures between −10° and 5° C.

The compounds of the formula I are basic and therefore form acid addition salts with inorganic or organic acids. Examples of non-toxic, pharmacologically acceptable acid addition salts are those formed with hydrochloric acid, hydrobromic acid, sulfuric acid, phosphoric acid, acetic acid, lactic acid, citric acid, tartaric acid, succinic acid, maleic acid or fumaric acid.

The starting compounds of the formula II to XXV are either described in the literature or may be prepared by methods described in the literature.

Thus, for example, a starting compound of the formulas IV and VIII is obtained by reacting a corresponding benzazepine with a corresponding halogen compound, and optionally subsequently reacting the product with a corresponding amine. The benzazepine of the formula II necessary for this reaction is obtained, for example, by cyclization of a compound of the formula

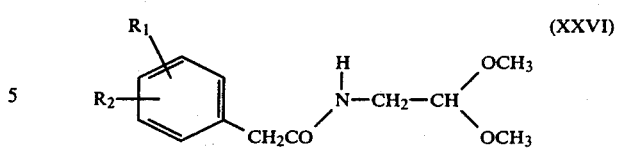

or of the formula

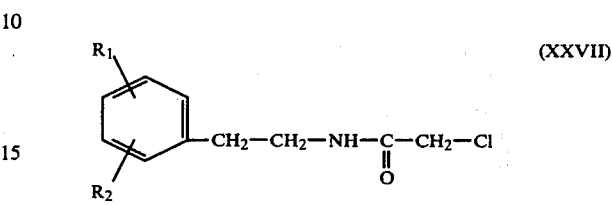

if R₁ and R₂ do not represent alkoxy groups, optionally followed by catalytic hydrogenation and/or reduction of the carbonyl group using sodium borohydride/glacial acetic acid, for example (see published European Application 0.007.070), and/or oxidation, for instance with selenium dioxide.

A starting compound of the formula VI is obtained, for example, by reacting a corresponding benzazepine with a corresponding haloacetal, followed by hydrolysis.

A starting compound of the formula X is obtained, for example, by reduction of a corresponding nitro compound.

A starting compound of the formulas XII, XIII, XV or XVI is obtained preferably by reaction of a corresponding halogen compound with a corresponding amine, and optional subsequent removal of protective radicals which are used for the protection of hydroxyl groups.

A starting compound of the formula XXI is obtained by reduction of a corresponding nitro compound which is in turn obtained by acylation or alkylation of a corresponding amine.

A starting compound of the formulas XVII to XIX and XXII to XXIV is preferably obtained by reacting a corresponding halogen compound with a corresponding amine, and optionally subsequently splitting off any protective groups used to protect the hydroxyl groups.

A starting compound of the formula XXV is obtained, for example, by chloromethylation of a compound of the formula

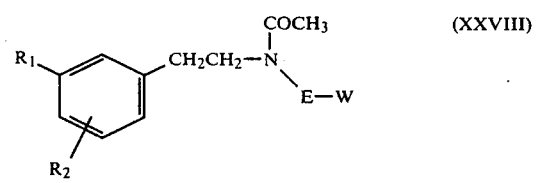

wherein R₁, R₂ and E have the meanings previously defined and W is a protected hydroxyl group, for example, acetoxy, benzoyloxy or 4-nitrobenzoyloxy, further reacting the product with an alkali metal cyanide, converting the group W into a suitable leaving group such as chlorine, bromine, iodine, methylsulfonyloxy or 4-methylphenylsulfonyloxy, and subsequently reacting the resulting compound with an amine of the formula

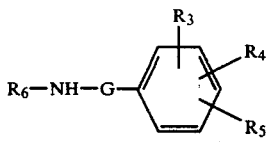
(XXIX)

wherein $R_3$ to $R_6$ and G have the meanings previously defined, optionally followed by hydrolysis and/or esterification or amidation.

The following examples illustrate the present invention and will enable others skilled in the art to understand it more completely. It should be understood, however, that the invention is not limited solely to the particular examples given below.

Preparation of the Starting Compounds

EXAMPLE A 7,8-Dimethoxy-1,3-dihydro-2H-3-benzazepin-2-one (a) 3,4-Dimethoxyphenyl-acetic acid chloride 600 ml of thionyl chloride were added dropwise to a suspension of 549.4 gm of 3,4-dimethoxyphenyl-acetic acid in 600 ml of methylene chloride, while stirring, over a period of 2 hours. After the evolution of gas had ceased (16 hours), the mixture was refluxed for an hour. After the volatile components had been removed, the residue was distilled in vacuo.

Yield: 486 gm (80.8% of theory).
B.p.: 134°–136° C./1.95 mbar.

(b) N-(2,2-dimethoxy-ethyl)-3,4-dimethoxyphenylacetamide

While cooling with ice, a solution of 485.2 gm of 3,4-dimethoxyphenyl-acetic acid chloride in 1.1 liters of methylene chloride at 15° C. to 20° C. was added dropwise to a solution of 246.2 ml of aminoacetaldehyde dimethyl acetal and 315 ml of triethylamine in 2.2 liters of methylene chloride, and the mixture was stirred for one hour at 16° to 18° C. Then, it was extracted with water several times, dried over magnesium sulfate and concentrated by evaporation. The oil thus obtained slowly crystallized.

Yield: 608 gm (95% of theory).
Melting point: 66°–69° C.

(c) 7,8-Dimethoxy-1,3-dihydro-2H-3-benzazepin-2-one

A solution of 600.6 gm of N-(2,2-dimethoxyethyl)-3,4-dimethoxyphenyl-acetamide in 3 liters of concentrated hydrochloric acid was mixed with 3 liters of glacial acetic acid. After standing for 17 hours at room temperature, the mixture was poured over ice. The crystals precipitated thereby were suction-filtered off, washed with water until neutral and dried.

Yield: 350 gm (75.4% of theory).
Melting point: 234°–237° C.

EXAMPLE B 7,8-Dimethoxy-1,3,4,5-tetrahydro-2H-3-benzazepin-2-one

A suspension of 21.9 gm (0.1 mol) of 7,8-dimethoxy-1,3-dihydro-2H-3-benzazepin-2-one and 1.5 gm of 10% palladium-on-charcoal in 200 ml of glacial acetic acid was hydrogenated at 50° C. and at a hydrogen pressure of 5 bar. After the catalyst had been filtered off, the solvent was evaporated in vacuo, and the residue was taken up in methylene chloride. After the solution had been extracted with an aqueous sodium bicarbonate solution and washed with water, it was dried over magnesium sulfate, evaporated and purified over silica gel with methylene chloride and then with increasing amounts of methanol (up to 10%).

Yield: 12.6 gm (57% of theory).
Melting point: 188°–191° C.

EXAMPLE C 7,8-Dimethoxy-2,3,4,5-tetrahydro-1H-3-benzazepine

A solution of 1.8 gm of glacial acetic acid in 10 ml of dioxane was added dropwise to a suspension of 1.3 gm (6 mmols) of 7,8-dimethoxy-1,3,4,5-tetrahydro-2H-3-benzazepin-2-one and 1.1 gm (3 mmols) of sodium borohydride in 20 ml of dioxane; the mixture was refluxed for 3 hours, concentrated by evaporation and mixed with water. The mixture was extracted twice by shaking with methylene chloride; the extract was concentrated by evaporation, and the residue was taken up in ether. After filtering, the ether was removed in vacuo.

Yield: 1.1 gm (92.7% of theory).
Melting point: 86°–89° C.

EXAMPLE D

N-{3-[N′-Methyl-N′-(2-(3,4-dimethoxy-phenyl)-ethyl)amino]-propyl}-2-(2-amino-4,5-dimethoxy-phenyl)acetamide 33.3 gm (0.07 mol) of N-{3-[N′-methyl-N′-(2-(3,4-dimethoxyphenyl)-ethyl)-amino]-propyl}-2-(2-nitro-4,5-dimethoxyphenyl)-acetamide, dissolved in 500 ml of methanol, were hydrogenated at 25° C. and at a hydrogen pressure of 5 bar for 8 hours in the presence of 10% palladium-on- charcoal. After removal of the catalyst, the solvent was distilled off in vacuo.

Yield: 31.5 gm (100% of theory), viscous oil.

EXAMPLE E 6,9-Dimethoxy-1,3-dihydro-2H-3-benzazepin-2-one 3 ml of polyphosphoric acid were poured on 2.0 gm (0.007 mol) of N-(2,2-dimethoxyethyl)-2,5-dimethoxyphenyl acetamide, and the mixture was stirred for 60 minutes at 90° C. Subsequently, the reaction mixture was mixed with ice water, and the precipitated product was suction-filtered and dried.

Yield: 0.98 gm (64% of theory).
Melting point: 188°–191° C.

EXAMPLE F 7,8-Dimethyl-1,3-dihydro-2H-3-benzazepin-2-one

This compound was prepared analogous to Example E from N-(2,2-dimethoxyethyl)-3,4-dimethylphenyl-acetamide and polyphosphoric acid.

Yield: 40.1% of theory.
Melting point: 220°–224° C.

EXAMPLE G 7,8-Dimethoxy-5-methyl-1,3-dihydro-3,4-benzodiazepin-2-one 19.5 gm (0.082 mol) of 2-acetyl-4,5-dimethoxyphenyl-acetic acid were suspended in 200 ml of ethanol, and the suspension was mixed with 8.2 ml of 98% hydrazine hydrate and refluxed for 6 hours. The reaction mixture was evaporated in vacuo and purified on a silicagel column with methylene chloride and 1% of ethanol as the eluant.

Yield: 9.6 gm (50% of theory).
IR-spectrum (methylene chloride): 3300 cm$^{-1}$ (NH), 2830 cm$^{-1}$ (OCH$_3$), 1650 cm$^{-1}$ (CO).

EXAMPLE H 7,8-Dimethoxy-1,3,4,5-tetrahydro-2H-3-benzazepine-2,4-dione (a)

7,8-Dimethoxy-2-amino-4-bromo-1H-3-benzazepinehydrobromide 3.7 gm (0.017 mol) of 3,4-dimethoxy-o-phenylenediacetonitrile were suspended in 10 ml of glacial acetic acid, and the suspension was mixed at 20° C. with 12 ml of 30% hydrobromic acid in glacial acetic acid. After stirring for 3 hours at room temperature, the obtained precipitate was suction-filtered off, washed with glacial acetic acid and then with acetone/ether, and dried.

Yield: 5.3 gm (82.8% of theory).
Melting Point: 210°–211° C. (decomp.).

(b)

7,8-Dimethoxy-1,3,4,5-tetrahydro-2H-3-benzazepin-2,4-dione 5.3 gm (0.014 mol) of 7,8-dimethoxy-2-amino-4-bromo-2H-3-benzazepine hydrobromide were dissolved in 100 ml of water at 85° C.; the solution was mixed with 1.3 gm of anhydrous sodium acetate, and the mixture was heated for one hour at 90° C. The reaction mixture was then cooled, suction-filtered, and the filter cake was washed with cold water and dried.

Yield: 2.9 gm (88% of theory).
Melting point: 235° C. (decomp.).

EXAMPLE I

N-[3-(7,8-Dimethoxy-1,3,4,5-tetrahydro-2H-3-benzazepin-2-one-3-yl)-propyl]-methylamine hydrochloride This compound was prepared analogous to Example B by catalytic hydrogenation of 1-[7,8-dimethoxy-1,3-dihydro-2H-3-benzazepin-2-on -3-yl]-3-(N-benzyl-methylamino)-propane.

Yield: 87% of theory.
Melting point: 110° C. (decomp.).

EXAMPLE J

1-Chloro-3-[N-methyl-N-(2-{3,4-dimethoxyphenyl}-ethyl)amino]-propane (a)

3-[N-Methyl-N-(2-{3,4-dimethoxy-phenyl}-ethyl-)amino]-propanol

A mixture of 2.1 gm (0.011 mol) of N-methyl-N-[2-(3,4-dimethoxy-phenyl)-ethyl]-amine and 0.9 gm (0.011 mol) of methyl acrylate was allowed to stand overnight at room temperature. The addition product thus obtained was dissolved in 40 ml of ether, and the solution was added dropwise, while stirring, over a period of 15 minutes to a suspension of 0.3 gm (0.008 mol) of lithium aluminum hydride in 20 ml of ether. After refluxing for 5 hours, the reaction mixture was cooled and subsequently 30 ml of saturated aqueous sodium sulfate solution were added dropwise thereto. The precipitate formed thereby was suction-filtered off over diatomaceous earth, and the filtrate was extracted with methylene chloride. The organic phase was dried over sodium sulfate and evaporated to dryness.

Yield: 3 gm (89.7% of theory).

IR-spectrum (methylene chloride): 366, 3230 cm$^{-1}$ (OH), m/e-253 (C$_{14}$H$_{23}$NO$_3$; 253.35).

(b)

1-Chloro-3-[N-methyl-N-(2-{3,4-dimethoxy-phenyl}-ethyl)-amino]-propane 275 gm of benzenesulfonic acid chloride were added to 4 gm of 3-[N-methyl-N-(2-{3,4-dimethoxy-phenyl}-ethyl)amino]-propanol. After standing for 30 minutes, the mixture was dissolved in methylene chloride, washed with an aqueous 30% sodium hydroxide solution and water, dried over sodium sulfate and evaporated in vacuo. After purifying the residue on a silica gel column (eluant: methylene chloride/ethanol) a colorless oil was obtained.

Yield: 1 gm (17% of theory).
C$_{14}$H$_{22}$ClNO$_2$ (271.8): Calc.: C-61.86%; H-8.15%; N-5.15%; Found: C-62.00%; H-8.00%; N-4.63%.

EXAMPLE K

N-Methyl-N-[2-(3,4-dimethoxy-phenyl)-ethyl]-acetidinium bromide 3 gm (0.011 mol) of 3-[N-methyl-N-(2-{3,4-dimethoxy-phenyl}-ethyl)-amino]-propanol were dissolved in 15 ml of methylene chloride, and at 0 to 5° C. a solution of 2 ml of phosphorus tribromide in 5 ml of methylene chloride was added dropwise thereto. After heating to room temperature, the reaction mixture was refluxed for 2 hours, evaporated to dryness; the residue was dissolved in methylene chloride, and the solution was washed with 2N sodium hydroxide and water. The organic phase was dried over sodium sulfate and evaporated to dryness. After purifying the crude product on a silica gel column (eluant: methylene chloride/ethanol=100:5), the residue obtained was heated for 40 minutes at 60–70° C.

Yield: 1.8 gm (48% of theory).
Melting point: 175–180° C.

EXAMPLE L 7,8-Dimethoxy-2,3-dihydro-1H-3-benzazepine

A boiling suspension of 0.8 gm of lithium aluminium hydride in 100 ml of absolute dioxane was mixed with 2.2 gm (0.01 mol) of 7,8-dimethoxy-1,3-dihydro-2H-3-benzazepin-2-one, and the mixture was refluxed for 3 hours. Ammonium chloride solution (10%) was added while cooling with ice water, and the precipitate formed thereby was suction-filtered off. The filtrate was evaporated in vacuo to a volume of about 20 ml, and the resulting white precipitate was suction-filtered off and washed with a little dioxane.

Yield: 0.9 gm (43.8% of theory).
Melting point: 162–163° C.

EXAMPLE M 1-(7,8-Dimethoxy-1,3,4,5-tetrahydro-2H-3-benzazepin-2-on-3-N-methyl-amino-propane-hydrochloride (a)

1-(7,8-Dimethoxy-1,3-dihydro-2H-3-benzazepin-2-on-3-yl)-3-N-methyl-N-benzyl-amino-propanehydrochloride This compound was prepared analogous to Example 111(b) by reacting 1-(7,8-dimethoxy-1,3-dimethoxy-1,3-dihydro-2H-3-benzazepin-2-on-3-yl)-3-chloro-propane with N-methyl-benzylamine.

Yield: 92.1% of theory.
Melting point: 208–209° C.

(b)

1-(7,8-Dimethoxy-1,3,4,5-tetrahydro-2H-3-benzazepin-2-on-3-yl)-3-N-methyl-amino-propanehydrochloride This compound was prepared analogous to Example 115 by catalytic hydrogenation of 1-(7,8-dimethoxy-1,3-dihydro-2H-3-benzazepin-2-on-3-yl)-3-N-methyl-N-benzylamino-propane.

Yield: 87% of theory.
Melting point: 110° C. (decomp.).

EXAMPLE N 1,3,4,5-Tetrahydro-2H-3-benzazepin-2-one (a) N-(2-Phenyl-ethyl)-1-chloro-acetamide 38.7 ml (0.3 mol) of 2-phenylethylamine and 45.9 ml (0.033 mol) of triethylamine were dissolved in 30 ml of methylene chloride, and the solution was mixed with a solution of 26.4 ml (0.33 mol) of chloroacetyl chloride in 150 ml of methylene chloride at 10° C. After one hour's stirring at room temperature, the reaction product was extracted with 1% acetic acid and with water, and the extract was dried over magnesium sulfate and concentrated by evaporation in vacuo.

Yield: 54.2 gm (91.4% of theory).
Melting point: 64–65° C.

(b) 1,3,4,5-Tetrahydro-2H-3-benzazepin-2-one 54.0 gm (0.373 mol) of N-(2-phenyl-ethyl)-1-chloroacetamide were mixed with 73.8 gm (0.55 ml) of aluminum chloride, and the mixture was stirred for 13 hours at 130–140° C. After the aluminum chloride had been destroyed with ice water, the product was extracted with methylene chloride, the extract was washed with water, dried over magnesium sulfate and concentrated by evaporation in vacuo, and the residue was purified by chromatography on silica gel, using methylene chloride plus 3% ethanol as the eluant.

Yield: 6.22 gm (14.1% of theory).
Melting point: 158–160° C.

EXAMPLE O 1-(7-Bromo-8-methoxy-1,3,4,5-tetrahydro-2H-3-benzazepin-2-on-3-yl)-3-chloropropane (a)
8-Methoxy-1,3,4,5-tetrahydro-2H-3-benzazepin-2-one 56.8 gm (0.3 mol) of 8-methoxy-1,3-dihydro-2H-benzazepin-2-one (melting point: 190–191° C.), dissolved in 600 ml of glacial acetic acid, were hydrogenated in the presence of 5 gm of 10% palladium-on-charcoal at a temperature of 80° C. under a hydrogen pressure of 5 bar for 12 hours. After filtering off the catalyst, the solvent was removed in vacuo. The residue was mixed with water and neutralized with potassium carbonate. The precipitate was suction-filtered off, washed with water and dried.

Yield: 51.1 gm (89.1% of theory).
Melting point: 160–161° C.

(b) 7-Bromo- and 9-Bromo-8-methoxy-1,3,4,5-tetrahydro-2H-3-benzazepin-2-one 64.5 gm 2.03 ml (0.04 mol) of bromine were added dropwise to a solution of 7.4 gm (0.04 mol) of 8-methoxy-1,3,4,5-tetrahydro-2H-3-benzazepin-2-one in 100 ml of 80% acetic acid at a temperature between 3° and 5° C., while stirring. After 15 minutes, the reaction mixture was poured into ice water, and the aqueous mixture was neutralized with potassium carbonate. The precipitate thus formed was suction-filtered off, washed with a little water and dried. The isomers were separated by means of chromatography on silica gel, using ethyl acetate as the eluant. Yield: 5.7 gm (52.8% of theory) of 9-bromo-isomer IR-spectrum (methylene chloride): 3,400 cm$^{-1}$ (NH), 1,660 cm$^{-1}$ (CO), 4.1 gm (38% of theory) of 7-bromo-isomer.

IR-spectrum (potassium bromide): 3,200 cm$^{-1}$ (NH), 1.665 cm$^{-1}$ (CO).

(c)
(7-Bromo-8-methoxy-1,3,4,5-tetrahydro-2H-3-benzazepin-2-on-3-yl)-3-chloro-propane 0.24 gm of a 55% sodium hydride dispersion in oil were added to a mixture of 1.35 gm (5 mol) of 7-bromo-8-methoxy-1,3,4,5-tetrahydro-2H-3-benzazepin-2-one in 15 ml of dimethylsulfoxide at room temperature. After stirring the mixture at room temperature for 30 minutes and at a temperature between 35° and 40° C. for 10 minutes, the obtained solution was added to 0.79 gm (5.5 mol) of 1-bromo-3-chloro-propane in 5 ml of dimethylsulfoxide. After stirring the mixture at room temperature for 2 hours, it was poured into ice water, and the aqueous mixture was extracted four times with methylene chloride. The methylene chloride extracts were washed with water, dried and evaporated in vacuo. The residue was purified by chromatography on silica gel, using ethyl acetate as the eluant.

Yield: 210 mg (12% of theory).
Melting point: 119°–120° C.

EXAMPLE P

7-Nitro-8-methoxy-1,3,4,5-tetrahydro-2H-3-benzazepin-2-one 765 mg (4 mmol) of 8-methoxy-1,3,4,5-tetrahydro-2H-3-benzazepin-2-one were added to a mixture of 15 ml of concentrated nitric acid and 1.5 ml of fuming nitric acid at a temperature between 3° and 5° C., while stirring. After stirring at this temperature for 30 minutes more, the mixture was poured into ice water, and the aqueous mixture was neutralized with potassium carbonate. The precipitate formed thereby was suction-filtered off, washed with water and dried. The yellow crystals were purified by chromatography on silica gel, using ethyl acetate as the eluant, to separate the corresponding 9-nitro- and 7,9-dinitro-isomers.

Yield: 400 mg (42.3% of theory). Melting point: 204°–205° C. (decomp.).

Preparation of End Products of the Formula I

EXAMPLE 1

1-[7,8-Dimethoxy-1,3-dihydro-2H-3-benzazepin-2-on-3-yl]-3-[N-methyl-N-(2-{3,4-dimethoxy-phenyl}ethyl)-amino]-propane hydrochloride (a) 1-(7,8-Dimethoxy-1,3-dihydro-2H-3-benzazepin-2-on-3-yl)-3-propane 131.5 gm (0.6 mol) of 7,8-dimethoxy-1,3-dihydro-2H-3-benzazepin-2-one were suspended in 900 ml of dimethyl-sulfoxide, and the suspension was mixed with 80.8 gm (0.72 mol) of potassium tert. butoxide, while stirring. After 20 minutes, the solution thus obtained was added dropwise, while cooling with ice water, to a solution of 77 ml (0.72 mol) of 1-bromo-3-chloro-propane in 300 ml of dimethyl-sulfoxide. After one hour, the mixture was poured into ice water. After a short time, the glutinous precipitate began to crystallize. The precipitate was suction-filtered off, dissolved in acetone, precipitated with water, then suction-filtered off and dried.

Yield: 155.5 gm (87.3% of theory).
Melting point: 101°–103° C.

(b)

1-[7,8-Dimethoxy-1,3-dihydro-2H-3-benzazepin-2-on-3-[N-methyl-N-(2-{3,4-dimethoxyphenyl}-ethyl)-amino]-propane hydrochloride A mixture of 5.9 gm (0.02 mol) of 1-(7,8-dimethoxy-1,3-dihydro-2H-3-benzazepin-2-on-3-yl) -3-chloro propane and 11.7 gm (0.0006 mol) of N-methyl-N-[2-(3,4-dimethoxy-phenyl)-ethyl]-amine was heated at 100° C. for 3 hours, then cooled and dissolved in ethyl acetate/water. The organic phase was removed, washed three times with 1% acetic acid and extracted by shaking twice with 2N hydrochloric acid. The hydrochloric acid extract was made alkaline with ammonia and extracted with methylene chloride. The solvent of the extract was removed in vacuo; the residue was dissolved in acetone, and the hydrochloride was precipitated with ethereal hydrochloric acid.

Yield: 6.9 gm (70.3% of theory).
Melting point: 190°–191° C. (decomp.).

EXAMPLE 2

1-[7,8-Dimethoxy-2,3,4,5-tetrahydro-1H-3,5-benzodiazepine-2,4-dione-3-yl]-3-[N-methyl-N-(2-{3,4-dimethoxy-phenyl}-ethyl)-amino]-propane hydrochloride 4.6 gm (0.01 mol) of N-[3-[N'-methyl-N'-(2-{3,4-dimethoxy-phenyl}-ethyl)-amino]-propyl]-2-(2-amino-4,5-dimethoxy-phenyl)-acetamide and 3.6 gm (0.022 mol) of N,N'-carbonyl-diimidazole were boiled in 100 ml of acetonitrile for 33 hours. The solvent was removed in vacuo, and the residue was purified on alumina (Woelm N, Act. III) with methylene chloride and 15% acetone as the eluant. The fractions were concentrated by evaporation in vacuo, the residue was dissolved in acetone, and the hydrochloride was precipitated with ethereal hydrochloric acid.

Yield: 1.1 gm (21.7% of theory).
Melting point: 125°–130° C.

EXAMPLE 3

1-[7,8-Dimethoxy-1,3,4,5-tetrahydro-2H-3-benzazepin-2-on-3-yl]-3-[N-methyl-N-(2-{2-amino-3,5-dichloro-phenyl}-ethyl-amino]-propane This compound was prepared analogous to Example 1(b) by reacting 1-(7,8-dimethoxy-1,3,4,5-tetrahydro-2H-3-benzazepin-2-on-3-yl)-3-chloro-propane with N-[2-(2-amino-3,5-dichloro-phenyl)-ethyl]-methylamine. Oil.

UV-spectrum (ethanol): λmax. 240 nm (0.34), 285 nm (0.14), 306 nm (0.10).

IR-Spectrum (dichloromethane): 2,810 cm$^{-1}$ (N-alkyl), 2,840 cm$^{-1}$ (O-OCH$_3$), 1,655 cm$^{-1}$ (C=O), 1,520 and 1,620 cm$^{-1}$ (C=C).

EXAMPLE 4

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane dihydrochloride 5.8 gm (0.0127 mol) of 1-[7,8dimethoxy-1,3-dihydro-2H-3-benzazepin-2-on-3-yl]-3-[N-methyl-N-(2-{3,4-dimethoxy-phenyl}-ethyl)-amino]-propane, dissolved in 60 ml of glacial acetic acid, were hydrogenated for 5 hours at room temperature and at a hydrogen pressure of 5 bar in the presence of 10% palladium-on-charcoal. The catalyst was filtered off; the filtrate was concentrated by evaporation in vacuo, and the residue taken up in methylene chloride/ semisaturated potassium carbonate solution. The organic phase was treated with activated charcoal/bleaching earth, filtered and evaporated in vacuo. Subsequently, the residue was dissolved in acetone, and the dihydrochloride was precipitated with ethereal hydrochloric acid.

Yield: 6.2 gm (92% of theory).
Melting point: 137° C. (decomp.).

When using the equimolar amount of ethanolic hydrochloric acid, the hydrochloride was obtained which had a melting point of 165°–168° C.

EXAMPLE 5

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane dihydrochloride (a)

1-(7,8-Dimethoxy-1,3,4,5-tetrahydro-2H-3-benzazepin-2-on-3-yl)-3-chloro-propane

This compound was prepared analogous to Example 1(a) by reacting 7,8-dimethoxy-1,3,4,5-tetrahydro-2H-3-benzazepin-2-one with 1-bromo-3-chloro-propane (yield: 50% of theory), or analogous to Example 4 by catalytic hydrogenation of 1-(7,8-dimethoxy-1,3-dihydro-2H-3-benzazepin-2-on-3-yl)-3-chloro-propane (yield: 88% of theory). Melting point: 84°–85° C.

(b)

1-[7,8-Dimethoxy-1,3,4,5-tetrahydro-2H-3-benzazepin-2-on-3-yl]-3-[N-methyl-N-(2-{3,4-dimethoxyphenyl}-ethyl)-amino]-propane dihydrochloride This compound was prepared analogous to Example 1(b) by reacting 1-(7,8-dimethoxy-1,3,4,5-tetrahydro-2H-benzazpein-2-on-3-yl)-3-chloro-propane with N-methyl-N-[2-(3,4-dimethoxy-phenyl)-ethyl]-amine.

Yield: 75.2% of theory.
Melting point: 135°–137° C. (decomp.).

EXAMPLE 6

1-[7,8-Dimethoxy-2,3,4,5-tetrahydro-1H-3-benzazepin-3-yl]-3-[N-methyl-N-(2-{3,4-dimethoxy-phenyl}ethyl)-amino]-propane dihydrochloride 2.7 gm (6 mmols) of 1-[7,8-dimethoxy-1,3,4,5-tetrahydro-2H-3-benzazepin-2-on-3-yl]-3-[N-methyl-N-(2-{3,4-dimethoxy-phenyl}ethyl)-amino]-propane were dissolved in 100 ml of absolute ether and 100 ml of absolute tetrahydrofuran; the solution was mixed with 0.25 gm of lithium aluminum hydride, and the mixture was refluxed for 3.5 hours. After cooling, a 10% ammonium chloride solution was added, while cooling was continued; then the mixture was suction-filtered, and the filtrate was concentrated by evaporation. The residue was purified on a silica gel column with methylene chloride.

EXAMPLE 7

1-[7,8-Dimethoxy-1,3-dihydro-2H-3-benzazepin-2-on-3-yl]-3-[N-methyl-N-(2-{4-methoxy-phenyl}-ethyl)-amino]-propane hydrochloride This compound was prepared analogous to Example 1(b) by reacting 1-(7,8-dimethoxy-1,3-dihydro-2H-3-benzazepin-2-on-3-yl)-3-chloropropane with N-methyl-N-[2-(4-methoxy-phenyl)-ethyl]-amine.

Yield: 76.2% of theory.
Melting point: 139°–142° C.

EXAMPLE 8

1-[7,8-Dimethoxy-1,3,4,5-tetrahydro-2H-3-benzazapin-2-on-3-yl]-3-[N-methyl-N-(2-{4-methoxy-phenyl}-ethyl)-amino]-propane hydrochloride This compound was prepared analogous to Example 4 by catalytic hydrogenation of 1-[7,8-dimethoxy-1,3-dihydro-2H-3-benzazepin-2-on-3-yl]-3- [N-methyl-N-(2-{4- methoxyphenyl}-ethyl)-amino]-propane.

Yield: 73.3% of theory.
Melting point: 175°–177° C.

EXAMPLE 9

1-[7,8-Methylenedioxy-1,3-dihydro-2H-3-benzazepin-2-on-3-yl]-3-[N-methyl-N-(2-{3,4-dimethoxy-phenyl}-ethyl)-amino]-propane hydrochloride (a)

1-(7,8-Methylenedioxy-1,3-dihydro-2H-benzazepin-2-on-3-yl)-3-chloro-propane

This compound was prepared analogous to Example 1(a) by reaction of 7,8-methylenedioxy-1,3-dihydro-2H-3-benzazepin-2-one [m.p.: 195° C. (decomp.)] with 1-bromo-3-chloro-propane.

Yield: 72.1% of theory.
Melting point: 75°–79° C.

(b)

1-[7,8-Methylenedioxy-1,3-dihydro-2H-3-benzazepin 2-on-3-yl]-3-[N-methyl-N-(2-{3,4-dimethoxy-phenyl}-ethyl)-amino]-propane hdyrochloride This compound was prepared analogous to Example 1(b) by reaction of 1-(7,8-methylenedioxy-1,3-dihydro-2H-benzazepin-2-on-3-yl) -3-chloro-propane with N-methyl-N-[2-(3,4-dimethoxy-phenyl)-ethyl]-amine.

Yield: 77.2% of theory.
Melting point: 185°–187° C.

EXAMPLE 10

1-[7,8-methylenedioxy-1,3,4,5-tetrahydro-2H-3-benzazepin-2-on-3-yl]-3-[N-methyl-N-(2-{3,4-dimethoxy-phenyl}-ethyl)-amino]-propane hydrochloride This compound was prepared analogous to Example 4 by catalytic hydrogenation of 1-[7,8-methylenedioxy-1,3-dihydro-2H-3-benzazepin-2-on-3-yl]-3-[N-methyl-N-(2-{3,4-dimethoxy-phenyl}-ethyl)-amino]-propane.

Yield: 77.3% of theory
Melting point: 210°–212° C.

EXAMPLE 11

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane 0.05 ml of glacial acetic acid were added to room temperature to a mixture of 0.22 gm (0.5 mmol) of 1-[7,8-dimethoxy-1,3,4,5-tetrahydro-2H-3-benzazepin-2-on-3-yl]-3-[N-(2-{3,4-dimethoxy-phenyl}-ethyl)-amino]-propane, 0.5 ml of 37% formalin solution, 2 ml of acetonitrile and 0.1 gm of sodium cyanoborohydride. After 2 hours, another 0.05 ml of glacial acetic acid was added, and the mixture was stirred for 30 minutes. The reaction mixture was worked up by evaporating, taking up in methylene chloride, and washing with 2N sodium hydroxide solution and water. The organic phase was dried over sodim sulfate, evaporated and purified on silica gel.

Yield: 104 mg (45.5% of theory), viscous oil.
IR-spectrum (methylene chloride): 1,654 cm$^{-1}$ (CO), 1,510 cm$^{-1}$ (aromatic C=C).
Melting point of the dihydrochloride: 137° C. (decomp.).

EXAMPLE 12

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]propane dihydrochloride 22 gm (0.075 mol) of N-[3-(7,8-dimethoxy-1,3,4,5-tetrahydro-2H-3-benzazepin-2-on-3-yl)-propyl]-methylamine were heated with 7.2 gm (0.036 mol) of 2-(3,4-dimethoxyphenyl)-ethyl-chloride for 20 hours at 140° C. After dissolving the reaction product in methylene chloride, the solution was washed twice with 2N sodium hydroxide and twice with water, dried over sodium sulfate and evaporated. The residue was purified by chromatography on silica gel (particle size: 0.063-0.2 mm; eluant; methylene chloride/methanol = 10:1). The product thus obtained was dissolved in acetone, and the dihydrocyloride was precipitated with ethereal hydrochloric acid.

Yield: 8.0 gm (45% theory).
Melting point: 135°–136° C. (decomp.).

EXAMPLE 13

1-[7,8-Dimethoxy-1,3,4,5-tetrahydro-2H-3-benzazepin-2-on-3-yl]-3-[N-methyl-N-(2-{4-acetylamino-3,5-dichloro-phenyl}-ethyl)-amino]-propane A solution of 3 gm (0.0063 mol) of 1-[7,8-dimethoxy-1,3,4,5,-tetrahydro-2H-3-benzazepin-2-on-3-yl]-3-[N-methyl-N-(2-{4amino-3,5-dichloro-phenyl}ethyl)-amino]-propane in 50 ml of chloroform and 0.7 gm (0.007 mol) of triethylamine was mixed at the boiling point in portions with altogether about 0.8 ml of acetyl chloride. After boiling it for several hours, the reaction mixture was cooled to room temperature and washed with water. The aqueous phase was made strongly alkaline with 2N sodium hydroxide and extracted with methylene chloride. The separated organic phase was dried over sodium sulfate and evaporated. The crude product thus obtained was purified by chromatography on silica gel (particle size: 0.063 to 0.2 mm, eluant: methylene chloride/methanol = 8:1).

Melting point: 144°–146° C.

EXAMPLE 14

1[7,8-Dimethoxy-1,3,4,5-tetrahydro-2H-3-benzazepin-2-on-3-yl]-3-[N-methyl-N-(2-{4-amino-3,5-dibromo-phenyl}ethyl)-amino]- propane 0.8 gm (0.005 mol) of bromine were added dropwise at room temperature, while stirring, to a solution of 1 gm (0.0025 mol) of 1-[7,8-dimethoxy-1,3,4,5-tetrahydro-2H-3-benzazepin-2-on-3-yl]-3-[N-methyl-N-(2-{4-amino-phenyl}-ethyl)-amino]-propane in 20 ml of 95% acetic acid. After about 60 minutes the solvent was removed in a rotary evaporator, and the residue was taken up in a mixture of 2N sodium hydroxide and methylene chloride. The methylene chloride phase was washed once with water, dried over sodium sulfate and evaporated in vacuo. The oily residue crystallized at room temperature and was recrystallized from absolute ethanol for further purification.

Melting point: 105°–110° C.

EXAMPLE 15

1-[7,8-Dimethoxy-1,3,4,5-tetrahydro-2H-3-benzazepin-2-on-3-yl]-3-[N-methyl-N-(2{3,4-dimethoxy-phenyl}-ethyl)amino]-propane 0.22 gm (0.5 mol) of 1-[7,8-dimethoxy-1,3,4,5-tetrahydro-2H-3-benzazepin-2-on-3-yl]-3-[N-(2-{3,4-dimethoxy-phenyl}-ethyl)-amino]-propane were heated with 0.2 ml of 37% formalin solution and 0.2 ml of 100% formic acid for 20 minutes at 90°–100° C. The reaction mixture was worked up analogous to Example 11. Viscous oil.

IR-spectrum (methylene chloride): 1,645 cm$^{-1}$ (CO), 1,510 cm$^{-1}$ (aromatic C=C)

Melting point of the dihydrochloride: 137° C. (decomp.).

EXAMPLE 16

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane 1.26 gm (20 mmols) of sodium cyanoborohydride were added to a solution of 3.29 gm (10.0 mmols) of N-[3-(7,8-dimethoxy-1,3,4,5-tetrahydro-2H-3-benzazepin-2-on-3-yl)-propyl]-methylamine hydrochloride and 1.8 gm (10.0 mmol) of 2-(3,4-dimethoxy-phenyl)-acetaldehyde in 40 ml of ethanol, while maintaining a pH of 6–7 by the addition of 2N hydrochloric acid, and stirring was continued for 48 hours at room temperature. After evaporating the solution in vacuo, the residue was taken up in dilute hydrochloric acid and extracted twice with ether. Subsequently, the aqueous phase was made alkaline and extracted three times with methylene chloride, and the organic phase was evaporated and purified on silica gel. Oil.

IR-spectrum (methylene chloride): 1,645 cm$^{-1}$ (CO) 1,510 cm$^{-1}$ (aromatic C=C)

Melting point of the dihydrochloride: 137° C. (decomp.).

EXAMPLE 17

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane 1.26 gm (20 mmols) of sodium cyanoboronhydride were added to a solution of 2.77 gm (10 mmols) of 3-(7.8-dimethoxyl-1,3,4,5-tetrahydro-2H-3-benzazepin-2-on-3-yl)-propionaldehyde and 1.95 gm (10 mmols) of N-methyl-N-[2-(3,4-dimethyoxy-phenyl)-ethyl]-amine in 40 ml of methanol, while maintaining a ph of 6–7 by addition of hydrochloric acid. At this pH the reaction mixture was stirred for 50 hours at room temperature. After evaporating the solution in vacuo, the residue was taken up in dilute hydrochloric acid, and the solution was extracted three times with ether. The aqueous phase ws made alkaline and extracted three times with methylene chloride, and the organic phase was evaporated and purified on silica gel. A light yellow, viscous oil was obtained.

IR-spectrum (methylene chloride): 1,645 cm$^{-1}$ (CO) 1,510 cm$^{-1}$ (aromatic C=C)

Melting point of the dihydrochloride: 137° C. (decomp.).

EXAMPLE 18

1-[8-Methoxy-1,3,4,5-tetrahydro-2H-3-benzazepin-2-on-3-yl]-3-[N-methyl-N-(2-{3,4-dimethoxy-phenyl}-ethyl)-amino]-propane dihydrochloride (a) 1-(8-Methoxy-1,3-dihydro-2H-3-benzazepin-2-on 3-yl)-3-chloro-propane This compound was prepared analogous to Example 1(a) by reacting 8-methoxy-1,3-dihydro-2H-3-benzazepin-2-one (melting point: 189°–190° C.) with 1-bromo-3-chloropropane.

Yield: 23% of theory.

IR-spectrum (methylene chloride): 1,655 cm$^{-1}$ (CO).

(b) 1-(8-Methoxy-1,3,4,5-tetrahydro-2H-3-benzazepin-2-on-3-yl)-3-chloropropane

This compound was prepared analogous to Example 4 by catalytic hydrogenation of 1-(8-methoxy-1,3-dihydro-2H-3-benzazepin-2-on-3-yl)-3-chloropropane.

Yield: 67% of theory.

IR-spectrum (methylene chloride): 1,645 cm$^{-1}$ (CO).

(c) 1-[8-Methoxy-1,3,4,5-tetrahydro-2H-3-benzazepin-2-on-3-yl]-3-[N-methyl-N-(2-{3,4-dimethoxy-phenyl}-ethyl)-amino]-propane dihydrochloride This compound was prepared analogous to Example 5(b) by reaction of 1-(8-methoxy-1,3,4,5-tetrahydro-2H-3-benzazepin-2-on-3-yl)-3-chloro-propane with N-methyl-N-[2-(3,4-dimethoxy-phenyl)-ethyl]-amine.

Yield: 14% of theory.

Melting point: 118°–121° C.

EXAMPLE 19

1-[7,8-Dimethoxy-1,3,4,5-tetrahydro-2H-3-benzazepin-2-on-3-yl]-3-[N-methyl-N-(2-{4-amino-3-chloro-phenyl}-ethyl)-amino]-propane This compound was prepared analogous to Example 12 from N-[3-(7,8-dimethoxy-1,3,4,5-tetrahydro-2H-3-benzazepin-2-on-3-yl)-propyl]-methylamine and 2-(4-amino-3-chlorophenyl)-ethyl bromide. Oil.

IR-spectrum (methylene chloride): 3,380, 3,480 cm$^{-1}$ (NH$_2$), 1,645 cm$^{-1}$ (CO).

UV-spectrum (ethanol): λmax: 238 nm (0.16), 280–290 nm (0.05).

EXAMPLE 20

1-[7,8-Dimethoxy-1,3,4,5-tetrahydro-2H-3-benzazepin-2-on-3-yl]-3-[N-ethyl-N-(2-{4-amino-3,5-dichloro-phenyl}-ethyl)-amino]-propane This compound was prepared analogous to Example 12 from N-[3-(4,8-dimethoxy-1,3,4,5-tetrahydro-2H-3-benzazepin-2-on-3-yl)-propyl]-ethylamine and 2-(4-amino-3,5-dichlorophenyl)-ethyl chloride. Oil.

IR-spectrum (methylene chloride): 3,390, 3,480 cm$^{-1}$ (NH$_2$), 1,650 cm$^{-2}$ (CO).

UV-spectrum (ethanol): λ max: 240 nm (0.13), 280–290 nm (0.05).

EXAMPLE 21

1-[7,8-Dimethoxy-1,3,4,5-tetrahydro-2H-3-benzazepin-2-on-3-yl]-3-[N-methyl-N-(2-{4-amino-3,5-dichloro-phenyl}-ethyl)-amino]-propane This compound was prepared analogous to Example 12 from N-[3-(7,8-dimethoxy-1,3,4,5-tetrahydro-2H-3-benzazepin-2-on-3-yl)-propyl]-methylamine and 2-(4-amino-3,5-dichlorophenyl)-ethyl chloride.

Melting point: 94°–104° C.

EXAMPLE 22

1-[7,8-Dimethoxy-1,3,4,5-tetrahydro-2H-3-benzazepin-2-on-3-yl]-3-[N-methyl-N-(2-{4-amino-3,5-dibromo-phenyl}-ethyl)-amino]-propane This compound was prepared analogous to Example 12 from N-[-3-(7,8-dimethoxy-1,3,4,5-tetrahydro-2H-3-benzazepin-2-on-3-yl)-propyl]-methylamine and 2-(4-amino-3,5-dibromophenyl)-ethyl chloride.

Melting point: 108°–112° C.

EXAMPLE 23

1-[7,8-Dimethoxy-1,3,4,5-tetrahydro-2H-3-benzazepin-2-on-3-yl]-3-[N-methyl-N-(2-{4-ethoxycarbonylamino-3,5-dichloro-phenyl}-ethyl)-amino]-propane This compound was prepared analogous to Example 13 from 1-[7,8-dimethoxy-1,3,4,5-tetrahydro-2H-3-benzazepin-2-on-3-yl]-3-[N-methyl-N-(2-{4-amino-3,5-dichloro-phenyl}-ethyl)-amino]-propane and ethyl chloroformate. Oil.

IR-spectrum (methylene chloride): 3,410 cm$^{-1}$ (NH), 1,650 cm$^{-1}$ (CO-N<), 1,735 cm$^{-1}$ (CO—O—), 1,800 cm$^{-1}$ (CO—O—).

UV-spectrum (ethanol): λ max: 240 nm (shoulder, 0.08), 280–290 nm (0.03).

EXAMPLE 24

1-[7,8-Dimethoxy-1,3,4,5-tetrahydro-2H-3-benzazepin-2-on-3-yl]-3-[N-methyl-N-(2-{4-bis-(ethoxycarbonyl)-amino-3,5-dichlorophenyl}-ethyl)-amino]-propane This compound was prepared analogous to Example 13 from 1-[7,8-dimethoxy-1,3,4,5-tetrahydro-2H-3-benzazepin-2-on-3-yl]-3-[N-methyl-N-(2-{4-amino-3,5-dichloro-phenyl}-ethyl)-amino]-propane and ethyl chloroformate. Oil.

IR-spectrum (methylene chloride): 1,650 cm$^{-1}$ (CO-N<), 1,730 cm$^{-1}$ (CO—O—), 1,760 cm$^{-1}$ (CO—O—), 1,800 cm$^{-1}$ (CO—O—).

UV-spectrum (ethanol): λ max: 228 nm (shoulder, 0.15), 282 nm (0.03).

EXAMPLE 25

1-[7,8-Dimethoxy-1,3,4,5-tetrahydro-2H-3-benzazepin-2-on-3-yl]-3-[N-methyl-N-(2-{4-ethoxycarbonylamino-3-cyano-5-fluoro-phenyl}-ethyl)-amino]-propane This compound was prepared analogous to Example 13 from 1-[7,8-dimethoxy-1,3,4,5-tetrahydro-2H-3-benzazepin-2-on-3-yl]-3-[N-methyl-N-(2-{4-amino-3-cyano-5-fluorophenyl}-ethyl)-amino]-propane and ethyl chloroformate in the presence of triethylamine.

IR-spectrum (methylene chloride): 3,400 cm$^{-1}$ (NH), 2,830 cm$^{-1}$ (OCH$_3$), 1,730, 1,650, 1,510 cm$^{-1}$ (CO).

EXAMPLE 26

1-[7,8-Dimethoxy-1,3,4,5-tetrahydro-2H-3-benzazepin-2-on-3-yl]-3-[N-methyl-N-(2-{4-dimethylamino-3,5-dichloro-phenyl}-ethyl)-amino]-propane This compound was prepared analogous to Example 11 from 1-[7,8-dimethoxy-1,3,4,5-tetrahydro-2H-3-benzazepin-2-one-3-yl]-3-[N-methyl-N-(2-{4-amino-3,5-dichloro-phenyl}-ethyl)-amino]-propane, paraformaldehyde and sodium cyanoborohydride in methaol. Oil.

IR-spectrum (methylene chloride): 1,650 cm$^{-1}$.

UV-spectrum (ethanol): λ max: 227 nm (shoulder, 0.16), 280 nm (0.12).

Example 27

1-[7,8-Dimethoxy-1,3-dihydro-2H-3-benzazepin-2-on-3-yl]-3-[N-methyl-N-(2-{4-amino-3,5-dichloro-phenyl}-ethyl)-amino]-propane This compound was prepared analogous to Example 1(b) from 1-(7,8-dimethoxy-1,3-dihydro-2H-3-benzazepin-2-on-3-yl)-3-chloro-propane and N-methyl-N-[2-(4-amino-3,5-dichloro-phenyl)-ethyl]-amine. Oil.

IR-spectrum (methylene chloride): 3,390, 3,480 cm$^{-1}$ (NH$_2$), 1,655 cm$^{-1}$ (CO).

UV-spectrum (ethanol): λ max: 238 nm (shoulder, 0.25), 280 nm (0.1), 303 nm (0.12).

EXAMPLE 28

1-[7,8-Dimethoxy-1,3,4,5-tetrahydro-2H-3-benzazepin-2-on-3-yl]-3-[N-methyl-N-(2-{4-amino-3,5-dichloro-phenyl}-ethyl)-amino]-propane This compound was prepared analogous to Example 4 from 1-[7,8-dimethoxy-1,3-dihydro-2H-3-benzazepin-2-on-3-yl]-3-[N-methyl-N-(2-{4-amino-3,5-dichloro-phenyl}-ethyl)-amino]-propane and hydrogen in the presence of palladium-on-charcoal in glacial acetic acid.

Melting point: 95°–104° C.

EXAMPLE 29

1-[7,8-Dimethoxy-1,3,4,5-tetrahydro-2H-3-benzazepin-2-on-3-yl]3-[N-ethyl-N-(2-{4-amino-3,5-dibromo-phenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-ethyl-N-[2-(4-amino-3,5-dibromo-phenyl)-ethyl]-amine. Oil.

IR-spectrum (methylene chloride): 3,380, 3,480 cm$^{-1}$ (NH$_2$), 1,645 cm$^{-1}$ (CO).

UV-spectrum (ethanol): λ max: 240 nm (shoulder, 0.13), 280–290 nm (0.04).

EXAMPLE 30

1-[7,8-Dimethoxy-1,3,4,5-tetrahydro-2H-3-benzazepin-2-on-3-yl]-3-[N-methyl-N-(2-{4-amino-3,5-dichlorophenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(4-amino-3,5-dichloro-phenyl)-ethyl]-amine.

Melting point: 94°–104° C.

EXAMPLE 31

1-[7,8-Dimethoxy-1,3,4,5-tetrahydro-2H-3-benzazepin-2-on-3-yl]-3-[N-isopropyl-N-(2-{4-amino-3,5-dichlorophenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-isopropyl-N-[2-(4-amino-3,5-dichloro-phenyl)-ethyl]-amine.

Melting point of the hydrochloride: <90° C. (sintering from 70° C.).

IR-spectrum (methylene chloride): 3,390, 3,480 cm$^{-1}$ (NH$_2$), 1,650 cm$^{-1}$ (CO).

UV-spectrum (ethanol): λ max: 238 nm (0.13), 280–290 nm (0.05).

EXAMPLE 32

1-[7,8-Dimethoxy-1,3,4,5-tetrahydro-2H-3-benzazepin-2-on-3-yl]-3[N-methyl-N-(1-methyl-2-{4-amino-3,5-dichlorophenyl}-ethyl)-amino]-propane hydrochloride This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(4-amino-3,5-dichloro-phenyl)-1-methyl-ethyl]-amine.

Melting point: 118°–128° C. (decomp.).

EXAMPLE 33

1-[7,8-Dimethoxy-1,3,4,5-tetrahydro-2H-3-benzazepin-2-on-3-yl]-3-[N-(2-{4-amino-3,5-dichloro-phenyl}-ethyl)-amino]-propane hydrochloride This compound was prepared analogous to Example 5(b) from 1-(7,8-dimethoxy-1,3,4,5-tetrahydro-2H-3-benzazepin-3-on-3-yl)-3-chloro propane and N-[2-(4-amino-3,5-dichloro-phenyl)-ethyl]-amine.

Melting point: 236°–241° C.

EXAMPLE 34

1-[7,8-Dimethoxy-1,3,4,5-tetrahydro-2H-3-benzazepin-2-on-3-yl]-3-[N-methyl-N-(2-{4-amino-3-chloro-5-methyl-phenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(4-amino-3-chloro-5-methyl-phenyl)-ethyl]-amine.

Melting point: 60° C. (sintering, melting at 73° C.).

IR-spectrum (methylene chloride): 3,390, 3,480 cm$^{-1}$ (NH$_2$), 1,650 cm$^{-1}$ (CO).

UV-spectrum (ethanol): λ max: 237 nm (0.14), 280–290 nm (0.05).

EXAMPLE 35

1-[7,8-Dimethoxy-1,3,4,5-tetrahydro-2H-3-benzazepin-2-on-3-yl]-3-[N-methyl-N-(2-{3,5-dichloro-4-hydroxyphenyl}-ethyl)-amino]-propane hydrochloride This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(3,5-dichloro-4-hydroxy-phenyl)-ethyl-amine.

Melting point: 225° C.

EXAMPLE 36

1-[7,8-Dimethoxy-1,3,4,5-tetrahydro-2H-3-benzazepin-2-on-3-yl]-3-[N-methyl-N-(2-{3-chloro-5-fluoro-4-β,β,β-trifluoro-ethylamino-phenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(3-chloro-5-fluoro-4-β,β,β-trifluoroethylaminophenyl)-ethyl]-amine.

m/e=545/547, (C$_{26}$H$_{32}$ClF$_4$N$_3$O$_3$; 546.03).

EXAMPLE 37

1-[7,8-Dimethoxy-1,3,4,5-tetrahydro-2H-3-benzazepin-2-on-3-yl]-3-[N-methyl-N-(2-{4-amino-3-chloro-5-fluorophenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(4-amino-3-chloro-5-fluoro-phenyl)-ethyl]-amine.

m/e=463/465, (C$_{24}$H$_{31}$ClFN$_3$O$_3$; 463.99).

EXAMPLE 38

1-[7,8-Dimethoxy-1,3,4,5-tetrahydro-2H-3-benzazepin-2-on-3-yl]-3-[N-methyl-N-(2-{4-amino-3-chloro-5-trifluoromethyl-phenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(4-amino-3-chloro-5-trifluoromethyl-phenyl)-ethyl]-amine. Oil.

IR-spectrum (methylene chloride): 3,410, 3,510 cm$^{-1}$ (NH$_2$), 1,650 cm$^{-1}$ (CO), 1,610, 1,520 cm$^{-1}$ (C=C), 2,800 cm$^{-1}$ (N-alkyl), 2,830 cm$^{-1}$ (OCH$_3$).

UV-spectrum (ethanol): λ max: 241 nm (0.33), 285 nm (0.10), 310 nm (0.08).

EXAMPLE 39

1-[7,8-Dimethoxy-1,3,4,5-tetrahydro-2H-3-benzazepin-2-on-3-yl]-3-[N-methyl-N-(2-{4-amino-3-cyano-5-fluorophenyl}-ethyl)-amino]-propane This compound was prepared analogous to Example 5(b) from 1-(7,8-dimethoxy-1,3,4,5-tetrahydro-2H-3-benzazepin-2-on-3-yl)-3-chloro-propane and N-methyl-N-[2-(4-amino-3-cyano-5-fluoro-phenyl)-ethyl]-amine.

IR-spectrum (methylene chloride): 3,400, 3,490 cm$^{-1}$ (NH$_2$), 2,830 cm$^{-1}$ (OCH$_3$), 2,220 cm$^{-1}$ (CN), 1,650 cm$^{-1}$ (CO).

EXAMPLE 40

1-[7,8-Dimethoxy-1,3-dihydro-2H-3-benzazepin-2-on-3-yl]-3-[N-benzyl-N-(2-{3,4-dimethoxy-phenyl}-ethyl)amino]-propane hydrochloride This compound was prepared analogous to Example 1(b) from 1-(7,8-dimethoxy-1,3-dihydro-2H-3-benzazepin-2-on-3-yl)-3-chloro-propane and N-benzyl-N-[2-(3,5-dimethoxyphenyl)-ethyl]-amine.
Yield: 51% of theory.
Melting point: 102° C. (decomp.).

EXAMPLE 41

1-[7,8-Dimethoxy-1,3-dihydro-2-H-3-benzazepin-2-on-3-yl]-3-[N-methyl-N-(2-{3,4-methylenedioxy-phenyl)}-ethyl)-amino]-propane hydrochloride This compound was prepared analogous to Example 1(b) from 1-(7,8-dimethoxy-1,3-dihydro-2H-3-benzazepin-2-on-3-yl)-3-chloro-propane and N-methyl-N-[2-(3,5-methylenedioxy-phenyl)-ethyl]-amine.
Yield: 48% of theory.
Melting point: 160°–162° C.

EXAMPLE 42

1-[7,9-dimethoxy-1,3-dihydro-2-H-3-benzazepin-2-on-3-yl]-3-(N-benzyl-methylamino)-propane hydrochloride This compound was prepared analogous to Example 1(b) from 1-(7,8-dimethoxy-1,3-dihydro-2H-3-benzazepin-2-on-3-yl)-3-chloropropane and N-methyl-benzylamine.
Yield: 92% of theory.
Melting point: 208°–209° C.

EXAMPLE 43

1-[7,8-Dimethoxy-1,3-dihydro-2H-3-benzazepin-3-on-3-yl]-4-[N-methyl-N-(2-{3,4-dimethoxy-phenyl}-ethyl)-amino]-butane hydrochloride This compound was prepared analogous to Example 1(b) from 1-(7,8-dimethoxy-1,3-dihydro-2H-3-benzazepin-2-on-3-yl)-4-chloro-butane and N-methyl-N-[2-(3,4-dimethoxyphenyl)-ethyl]-amine.
Yield: 85% of theory.
Melting point: 162°–164° C.

EXAMPLE 44

1-[8-Propoxy-1,3-dihydro-2H-3-benzazepin-2-on-3-yl]-2-[N-methyl-N-(2-{3,4-dimethoxy-phenyl}-ethyl)-amino]-ethane hydrochloride This compound was prepared analogous to Example 1(b) from 1-(8-propoxy-1,3-dihydro-2H-3-benzazepin-2-on-3-yl)-2-chloro-ethane and N-methyl-N-[2-(3,4-dimethoxyphenyl)-ethyl]-amine.
Yield: 31% of theory.
Melting point: 155°–157° C.

EXAMPLE 45

1-[7,8-Dimethoxy-1,3,4,5-tetrahydro-2H-3-benzazepin-2-on-3-yl]-4-[N-methyl-N-(2-{3,4-dimethoxy-phenyl}-ethyl)-amino]-butane hydrochloride This compound was prepared analogous to Example 4 by catalytic hydrogenation of 1-[7,8-dimethoxy-1,3-dihydro-2H-3-benzazepin-2-on-3-yl]-4-[N-methyl-4-(2-{3,4-dimethoxyphenyl}-ethyl)-amino]-butane.
Melting point: 192°–194° C.

EXAMPLE 46

1-[7,8-Dimethoxy-1,3,4,5-tetrahydro-2H-3-benzazepin-2-on-3-yl]-3-[N-methyl-N-(2-{3,4-methylenedioxy-phenyl}-ethyl)-amino]-propane hydrochloride This compound was prepared analogous to Example 4 by catalytic hydrogenation of 1-[7,8-dimethoxy-1,3-dihydro-2H-3-benzazepin-2-on-3-yl]-3-[N-methyl-N-(2-{3,4-methylenedioxy-phenyl}-ethyl)-amino]-propane.
Yield: 72% of theory.
Melting point: 191°–193° C.

EXAMPLE 47

1-[7,8-Dimethoxy-1,3,4,5-tetrahydro-2H-3-benzazepin-3-on-3-yl]-3-[N-(2-{3,4-dimethoxy-phenyl}-ethyl)-amino]-propane hydrochloride This compound was prepared analogous to Example 4 by catalytic hydrogenation of 1-[7,8-diemthoxy-1,3-dihydro-2H-3-benzazepin-2-on-3-yl]-3-[N-benzyl-N-(2-{3,4-dimethoxy-phenyl}-ethyl)-amino]propane.
Yield: 81% of theory.
Melting point: 152°–154° C.

EXAMPLE 48

1-[7,8-Dimethoxy-1,3,4,5-tetrahydro-2H-3-benzazepin-2-on-3-yl]-3-[N-allyl-N-(2-{3,4-dimethoxy-phenyl}-ethyl)-amino]-propane hydrochloride 3.1 gm (0.007 mol) of 1-[7,8-dimethoxy-1,3,4,5-tetrahydro-2H-3-benzazepin-2-on-3-yl]-3-[N-(2-{3,4-dimethoxy-phenyl}-ethyl)-amino]-propane were refluxed for 21 hours with 1.0 gm (0.007 mol) of potassium carbonate and 0.6 ml (0.007 mol) of allyl bromide in 100 ml of chloroform. Subsequently, the organic phase was extracted with water, dried, evaporated in vacuo, and the residue was purified on an aluminum oxide column (300 gm neutral, activity III) with methylene chloride containing 2% of acetone as the eluant. Subsequently the hydrochloride was precipitated.
Yield: 40% of theory.
Melting point: 153°–155° C.

EXAMPLE 49

1-[7,8-Dimethoxy-1,3,4,5-tetrahydro-2H-3-benzazepin-2-on-3-yl]-3-[N-propyl-N-(2-{3,4-dimethoxy-phenyl}-ethyl)-amino]-propane hydrochloride This compound was prepared analogous to Example 48 from 1-[7,8-dimethoxy-1,3,4,5-tetrahydro-2H-3-benzazepin-2-on-3-yl]-3-[N-(2-{3,4-dimethoxy-phenyl}-ethyl)-amino]-propane and 1-bromo-propane.
Yield: 53% of theory.
Melting point: 80° C. (decomp.).

EXAMPLE 50

Mixture of isomers of 1-[7,8-dimethoxy-1,3-dihydro-2H-3-benzazepin-2-on-3-yl]-3-[N-methyl-N-(2-{2- and 4-nitro-phenyl}-ethyl)-amino]-propane The isomeric mixture was prepared analogous to Example 1(b) from 1-(7,8-dimethoxy-1,3-dihydro-2H-3-benzazepin-2-on-3-yl)-3-chloro-propane and N-methyl-2-(4- and 2-nitro-phenyl)-ethylamine.
Yield: 70% of theory.
IR-spectrum (methylene chloride): 1,655 cm$^{-1}$ (CO), 1,510 and 1,345 cm$^{-1}$ ($NO_2$).
NMR-spectrum ($CDCl_3/D_2O$): δ=8.10 ppm, d(J=9 Hz), 2H (aromatic) (4-nitro compound), δ=7.83 ppm, d(J=7 Hz), 2H (aromatic) (2-nitro compound).

EXAMPLE 51

Mixture of isomers of
1-[7,8-dimethoxy-1,3-dihydro-2H-3-benzazepin-2-on-3-yl]-3-[N-methyl-N-(2-{2-amino- and 4-amino-phenyl}-ethyl)-amino]-propane hydrochloride This isomeric mixture was prepared analogous to Example 4 by catalytic reduction of an isomeric mixture of 1-[7,8-dimethoxy-1,3-dihydro-2H-3-benzazepin-2-on-3-yl-]-3-[N-methyl-N-(2-{2- and 4-nitro-phenyl}-ethyl)-amino]-propane.

Yield: 34% of theory.
Melting point: 100° C. (decomp.).
IR-spectrum-(methylene chloride): 1,660 cm$^{-1}$ (CO).
$C_{24}H_{31}N_3O_3 \times HCl$, (446.0): Calc.: C-64.34%; H-7.65%; N-9.38%; Cl-7.91%; Found: C-63.60%; H-7.20%; N-9.28%; Cl-7.94%.

EXAMPLE 52

1-[7,8-Dimethoxy-1,3-dihydro-2H-3-benzazepin-2-on-3-yl]-3-[N-methyl-N-(2-{4-acetylamino-phenyl}-ethyl)-amino]-propane and 1-[7,8-Dimethoxy-1,3-dihydro-2H-3-benzazepin-2-on-3-yl]-3-[N-methyl-N-(2-{2-acetylamino-phenyl}-ethyl)-amino]-propane 1.8 gm (0.004 mol) of an isomeric mixture of 1-[7,8-dimethoxy-1,3-dihydro-2H-3-benzazepin-2-on-3-yl]-3-[N-methyl-N-(2-{2- and 4-amino-phenyl}-ethyl)-amino]-propane were stirred at room temperature for one hour in a mixture of 10 ml of glacial acetic acid and 10 ml of acetic anhydride. Subsequently, water was added, and the reaction mixture was neutralized with sodium bicarbonate and extracted with methylene chloride. The organic phase was dried and evaporated in vacuo, and the residue was chromatographed on aluminum oxide (200 gm, neutral, activity IV) (eluant: methylene chloride +1% methanol).

Yield of 2-acetylamino compound: 0.24 gm (14$ of theory), Melting point: 62°–66° C.

Yield of 4-acetylamino compound: 0.5 gm (28% of theory), Melting point: 69°–72° C.

EXAMPLE 53

1-[7,8-Dimethoxy-1,3,4,5-tetrahydro-2H-1,3-benzodiazepin-2-on-3-yl]-3-[N-methyl-N-(2-{3,4-dimethoxy-phenyl}-ethyl)-amino]-propane (a)

N-[3,-[N'Methyl-N'-(2-{3,4-dimethoxy-phenyl}-ethyl)-amino]-propyl]-2-(2-amino-4,5-dimethoxy-phenyl)-ethylamine 4.5 gm (0.01 mol) of N-[3-[N'-methyl-N'-(2-{3,4-dimethoxy-phenyl}-ethyl)-amino]-propyl]-2-(2-amino-4,5-dimethoxy-phenyl)-acetamide were dissolved in 100 ml of tetrahydrofuran and reacted in a nitrogen atmosphere with 60 ml of a 1-molar diborane solution in tetrahydrofuran. The clear solution was allowed to stand for 2 days at rooom temperature and was then mixed with 20 ml of semi-concentrated hydrochloric acid, while cooling. The tetrahydrofuran was distilled off in vacuo, and the acid residue was made alkaline with concentrated sodium hydroxide, while cooling. The precipitated oil was taken up in methylene chloride, and the organic phase was separated, dried and evaporated in vacuo. The oily residue was purified on silica gel with methylene chloride and 1% of methanol.

Yield: b 2.9 gm (67.2% of theory).
IR-spectrum (methylene chloride): 2,830 cm$^{-1}$ ($OCH_3$), 2,800 cm$^{-1}$ (N-alkyl).

(b)

1-[7,8-Dimethoxy-1,3,4,5-tetrahydro-2H-1,3-benzodiazepin-2-on-3-yl]-3-[N-methyl-(2-{3,4-dimethoxy-phenyl}-ethyl)-amino]-propane This compound was prepared analogous to Example 2 by reacting N-[3-[N'methyl-N'-(2-{3,4-dimethoxy-phenyl}- ethyl)-amino]-propyl]-N-[2-(2-amino-4,5-dimethoxy-phenyl)-ethyl]-amine with N,N'-carbonyl-diimidazole.

Yield: 0.9 gm (61.6% of theory).
Melting point: 116°–117° C.

EXAMPLE 54

1-[7,8-Dimethoxy-5-methyl-1,3-dihydro-2H-3,4-benzodiazepin-2-on-3-yl]-3-[N-methyl-N-(2-{3,4-dimethoxy-phenyl}-ethyl)-amino]-propane dihydrochloride This compound was prepared analogous to Example 1(b) by reaction of 1-(7,8-dimethoxy-5-methyl-1,3-dihydro-2H-3,4-benzodiazepin-2-on-3-yl)-3-chloro-propane with N-methyl-2-(3,4-dimethoxy-phenyl)-ethyl-amine.

Yield: 24.2% of theory.
Melting point: 106° C.

EXAMPLE 55

1-[7,8-Dimethoxy-1,3-dihydro-2H-3-benzazepin-2-on-3-yl]-2-hydroxy-3-[N-methyl-N-(2-{3,4-dimethoxy-phenyl}-ethyl)-amino]-propane (a)

1-(7,8-Dimethoxy-1,3-dihydro-2H-3-benzazepin-2-on-3-yl)-2,3-epoxy-propane

This compound was prepared analogous to Example 1(a) by reacting 7,8-dimethoxy-1,3-dihydro-2H-3-benzazepin-2-one with epichlorohydrin.

Yield: 94.5% of theory.
IR-spectrum (methylene chloride): 2,830 cm$^{-1}$ ($OCH_3$), 1,660 cm$^{-1}$ (CO).

(b)

1-[7,8-Dimethoxy-1,3-dihydro-2H-3-benzazepin-2-on-3-yl]-2-hydroxy-2-[N-methyl-N-(2-{3,4-dimethoxy-phenyl}-ethyl)-amino]-propane 8.25 gm (0.03 mol) of 1-(7,8-dimethoxy-1,3-dihydro-2H-3-benzazepin-2-on-3-yl)-2,3-epoxy-propane were dissolved in 100 ml of methanol, 5.85 gm (0.03 mol) of N-methyl-N-[2-(3,4-dimethoxy-phenyl)-ethyl]-amine were added, and the mixture was refluxed for 3 hours. The methanol was distilled off in vacuo, and the residue was purified on a silica gel column with methylene chloride +1% of ethanol.

Yield: 7.8 gm (55.2% of theory).
IR-spectrum (methylene chloride): 3,600 cm$^{-1}$ (OH), 1,650 cm$^{-1}$ (CO).
$C_{26}H_{34}N_2O_6$, (470.6): Calc.: C-66.36%; H-7.28%; N-5.95%; Found: C-66.16%; H-7.26%; N-5.80%.

EXAMPLE 56

1-[7,8-Dimethoxy-1,3,4,5-tetrahydro-2H-3-benzazepine-1,2-dione-3-yl]-3-[N-methyl-N-(2-{3,4-dimethoxyphenyl}-ethyl)-amino]-propane hydrochloride 3.5 gm of selenium dioxide were added to a mixture of 150 ml of diozane and 6 ml of water at 70° C.; the mixture was stirred for 15 minutes and then admixed with 3 gm of diatomaceous earth and 14.8 gm (0.03 mol) of 1-[7,8-dimethoxy-1,3,4,5-tetrahydro-2H-3-benzazepin-2-on-3-yl]-3-[N-methyl-N-(2-{3,4-dimethoxyphenyl}-ethyl)-amino]-propane hydrochloride. The mixture was refluxed for 6 hours, cooled and filtered. The filtrate was evaporated in vacuo and the residue was purified on a silica gel column with methylene chloride +1% of ethanol as the eluant. The fractions were evaporated in vacuo; the residue was dissolved in acetone, and the hydrochloride was precipitated with ethereal hydrochloric acid.

Yield: 13.8 gm (90.7% of theory).
Melting point: 196°–197° C.

EXAMPLE 57

1-[7,8-Dimethoxy-1,3,4,5-tetrahydro-2H-3-benzazepin-2-on-3-yl]-2-hydroxy-3-[N-methyl-N-(2-{3,4-dimethoxy-phenyl}-ethyl)-amino]-propane This compound was prepared analogous to Example 4 by catalytic hydrogention of 1-[7,8-dimethoxy-1,3-dihydro-2H-3-benzazepin-2-on-3-yl]-2-hydroxy-3-[N-methyl-N-(2-{3,4-dimethoxy-phenyl}-ethyl)-amino]-propane, but in ethanol at 50 bar and 70° C. with platinum oxide as the catalyst.

Yield: 37.5% of theory.
IR-spectrum (methylene chloride): 3,470 cm$^{-1}$ (OH), 1,635 cm$^{-1}$ (CO).
$C_{26}H_{36}N_2O_6$, (472.6): Calc.: C-66.08%; H-7.68%; N-5.93%, Found: C-66.22%; H-7.57%; N-5.85%.

EXAMPLE 58

1-[7,8-Dimethoxy-1,3,4,5-tetrahydro-2H-3-benzazepin-2-on-3-yl]-3-[N-methyl-N-(2-{4-nitro-phenyl}-ethyl)-amino]-propane hydrochloride This compound was prepared analogous to Example 5 (b) by reaction of 1-[7,8-dimethoxy-1,3,4,5-tetrahydro-2H-3-benzazepin-2-on-3-yl]-3-chloro-propane with N-methyl-N-[2-(4-nitro-phenyl)-ethyl]-amine.

Yield: 56.5% of theory.
Melting point: 182° C.

EXAMPLE 59

1-[7,8-Dimethoxy-1,3,4-5-tetrahydro-2H-3-benzazepin-2-on-3-yl]-3-[N-methyl-N-(2-{3-nitro-4-acetylamino-phenyl}-ethyl)-amino]-propane dihydrochloride 0.3 gm (1.18 mmols) of N-[3-7,8-dimethoxy-1,3,4,5-tetrahydro-2H-3-benzazepin-2-on-3-yl)-propyl]-methylamine and 0.34 gm (1.3 mmols) of 2-(3-nitro-3-acetylamino-phenyl)-ethyl bromide were refluxed for one hour in 5 ml of chloro-benzene and 0.1 ml of pyridine. The reaction mixture was then cooled, and the precipitated pyridine hydrobromide was suction-filtered off. The filtrate was evaporated in vacuo, and the residue was purified on aluminum oxide (neutral, activity II) with methylene chloride and 0.5% of ethanol as the eluant. The oil thus obtained was dissolved in acetone, and the dihydrochloride was precipitated with ethereal hydrochloric acid.

Yield: 230 mg (57.7% of theory).
Melting point: 170° C.

EXAMPLE 60

1-[7,8-Dimethoxy-1,3,4,5-tetrahydro-2H-3-benzazepin-2-on-3-yl]-3-[N-methyl-N-(2-{4-fluoro-phenyl}-ethyl)-amino]-propane dihydrochloride This compound was prepared analogous to Example 5(b) by reacting 1-(7,8-dimethoxy-1,3,4,5-tetrahydro-2H-3-benzazepin-2-on-3-yl)-3-chloro-propane with N-methyl-N-[2-(4-fluoro-phenyl)-ethyl]-amine.

Yield: 68.7% of theory.
Melting point: 203° C.

EXAMPLE 61

1[7,8-Dimethoxy-1,3,4,5-tetrahydro-2H-3-benzazepin-2-on-3-yl]-3-[N-acetyl-N-(2-{3,4-dimethoxy-phenyl}-ethyl)-amino]-propane 2 gm (0.0045 mol) of 1-[7,8-dimethoxy-1,3,4,5-tetrahydro-2H-3-benzazepin-2-on-3-yl]-3-[N-(2-{3,4-dimethoxy-phenyl}-ethyl)-amino]-propane were admixed with 15 ml of acetic acid anhydride, and the mixture was stirred for 30 minutes at room temperature. The mixture was then poured into ice water, and the aqueous mixture was naturalized with sodium bicarbonate and subsequently extracted with methylene chloride. The organic extract was dried over magnesium sulfate, filtered, and evaporated in vacuo. The residue was purified on aluminum oxide (neutral, activity II) with methylene chloride as the eluant.

Yield: 1.5 gm (68.5% of theory).
IR-spectrum (methylene chloride: 2,830 cm$^{-1}$ (OCH$_3$), 1,640 cm$^{-1}$ (CO).
$C_{27}H_{36}N_2O_6$, (484.6): Calc.: C-66.92%; H-7.49%; N-5.78%, Found: C-66.75%; H-7.44%; N-5.80%.

EXAMPLE 62

1-[7,8-Dimethoxy-1,3,4,5-tetrahydro-2H-3-benzazepin-2-on-3-yl]-3-[N-ethoxycarbonyl-N-(2-{3,4-dimethoxyphenyl}-ethyl)-amino]-propane 2.5 gm (0.00565 mol) of 1-[7,8-dimethoxy-1,3,4,5-tetrahydro-2H-3-benzazepin-2-on-3-yl]-3-[N-(2-{3,4-dimethoxy-phenyl}-ethyl)-amino]-propane and 2.45 gm (0.024 mol) of triethylamine were dissolved in 20 ml of methylene chloride. After addition of 2.6 gm (0.024 mol) of ethyl chloroformate, the mixture was stirred for 30 minutes at room temperature, and the solution was washed twice with water, dried over magnesium sulfate and evaporated in vacuo. The residue was purified on aluminum oxide (neutral, activity II) with methylene chloride as the eluant.

Yield: 1.5 gm (51.6% of theory).
IR-spectrum (methylene chloride): 1,690, 1,650 cm$^{-1}$ (CO).
$C_{28}H_{38}N_2O_7$, (514.6): Calc.: C-65.30%; H-7.44%; N-5.44%, Found: C-64.19%; H-7.14%; N-5.27%.

EXAMPLE 63

1-[7,8-Dimethoxy-1,3,4,5-tetrahydro-2H-3-benzazepin-2-on-3-yl]-3-[N-methyl-N-(2-{2,6-dichloro-phenyl}-ethyl)-amino]-propane dihydrochloride This compound was prepared analogous to Example 5(b) by reacting 1-(7,8-dimethoxy-1,3,4,5-tetrahydro-2H-3-benzazepin-2-on-3-yl)-3-chloro-propane with N-methyl-N-[2-(2,6-dichloro-phenyl)-ethyl]-amine.

Yield: 70.5% of theory.

Melting point: 147° C.

EXAMPLE 64

1-[7,8-Dimethoxy-1,3,4,5-tetrahydro-2H-3-benzazepin-2-on-3-yl]-3-[N-methyl-N-(2-{3,4-dichloro-phenyl}-ethyl)-aminol]-propane dihydrochloride This compound was prepared analogous to Example 5(b) by reacting 1-(7,8-dimethoxy-1,3,4,5-tetrahydro-2H-3-benzazepin-2-on-3-yl)-3-chloro-propane with N-methyl-N-[2-(3,4-dichloro-phenyl)-ethyl]-amine.

Yield: 57.6% of theory.
Melting point: 161° C.

EXAMPLE 65

1-[7,8-Dimethoxy-1,3-dihydro-2H-3-benzazepin-2-on-3-yl]-2-[N-methyl-N-(2-{3,4-dimethoxy-phenyl}-ethyl)-amino]-ethane (a)

1-(7,8-Dimethoxy-1,3-dihydro-2H-3-benzazepin-2-on-3-yl)-2-chloro-ethane

This compound was prepared analogous to Example 1(a) by reacting 7,8-dimethoxy-1,3-dihydro-2H-3-benzazepin-2-one with 1-chloro-2-bromo-ethane.

Yield: 20% of theory.
Melting point: 114° C.

(b)

1-[7,8-Dimethoxy-1,3-dihydro-2H-3-benzazepin-2-on-3-yl]-2-[N-methyl-N-(2-{3,4-dimethoxy-phenyl}-ethyl)-amino]-ethane This compound was prepared analogour to Example 1(b) by reacting 1-(7,8-dimethoxy-1,3-dihydro-2H-3-benzazepin-2-on-3-yl)-2-chloro-ethane with N-methyl-N-[2-(3,4-dimethoxy-phenyl)-ethyl]-amine.

Yield: 72% of theory.

IR-spectrum (methylene chloride): 2,830 $cm^{-1}$ ($OCH_3$), 2,790 $cm^{-1}$ (N-alkyl), 1,655 $cm^{-1}$ (CO).

NMR-spectrum ($CDCl_3$): δ=2.3 ppm, s, 3H ($NCH_3$); 3.85 ppm, s, 12H ($OCH_3$); 6.15 ppm, d(J=8 Hz), 1H (olefin.); 6.35, d(J=8 Hz), 1H (olefin.).

EXAMPLE 66

1-[7,8-Dimethoxy-1,3,4,5-tetrahydro-2H-3-benzazepin-2-on-3-yl]-2-[N-methyl-N-(2-{,4-dimethoxy-phenyl}-ethyl)-amino]-ethane hydrochloride This compound was prepared analogous to Example 4 by catalytic hydrogenation of 1-[7,8-dimethoxy-1,3-dihydro-2H-3-benzazepin-2-on-3-yl]-2-[N-methyl-N-(2-{3,4-dimethoxy-phenyl}-ethyl)-amino]-ethane.

Yield: 59% of theory.
Melting point: 188°-189° C.

EXAMPLE 67

1-[7,8-Dimethoxy-1,3,4,5-tetrahydro-2H-3-benzazepine-2,4-dione-3-yl]3-[N-methyl-N-(2-{3,4-dimethoxy-phenyl}-ethyl)-amino]-propane hydrochloride (a)

1-(7,8-Dimethoxy-1,3,4,5-tetrahydro-2H-3-benzazepine-2,4-dione-3-yl)-3-chloro-propane This compound was prepared analogous to Example 1(a) by reacting 7,8-dimethoxy-1,3,4,5-tetrahydro-2H-3-benzazepine-2,4-dione [m.p.: 235° C. (decomp.)] with 1-bromo-3-chloro-propane.

Yield: 26% of theory.
IR-spectrum (KBr): 1660 $cm^{-1}$ (CO).

(b)

1-[7,8-Dimethoxy-1,3,4,5-tetrahydro-2H-3-benzazepine-2,4-dione-3-yl]-3-[N-methyl-N-(2-{3,4-dimethoxy-phenyl}-ethyl)-amino]-propane hydrochloride This compound was prepared analogous to Example 5(b) by reacting 1-(7,8-dimethoxy-1,3,4,5-tetrahydro-2H-3-benzazepine-2,4-dione-3-yl)-3-chloro-propane with N-methyl-N[2-(3,4-dimethoxy-phenyl)-ethyl]-amine.

Yield: 35% of theory.
Melting point: 163°-164° C.

EXAMPLE 68

1-[7-Benzyloxy-8-hydroxy-1,3,4,5-tetrahydro-2H-3-benzazepin-2-on-3-yl]-3-[N-methyl-N-(2-{3,4-dimethoxy-phenyl}-ethyl)-amino]-propane (a)

1-(7,8-Dihydroxy-1,3,4,5-tetrahydro-2H-3-benzazepin-2-on-3-yl)-3-chloro-propane 8.9 gm (0.03 mol) of 1-(7,8-dimethoxy-1,3,4,5-tetrahydro-2H-3-benzazepin-2-on-3-yl)-3-chloro-propane were dissolved in 100 ml of methylene chloride; the solution was admixed at −60° C. with 2.1 ml of boron tribromide. After removing the cooling bath the reaction temperature rose to 20° C. and at this temperature the reaction mixture was stirred for 10 hours. The resulting resinous precipitate was made to crystallize by addition of 100 ml of water and subsequent stirring for one hour. The crystalline precipitate was suction-filtered off and washed with water and methylene chloride. For purification the crystalline product was stirred with acetone and suction-filtered off.

Yield: 7.3 gm (90.2% of theory).
Melting point: 177°-178° C.

(b)

1-[7-Hydroxy-8-benzyloxy-1,3,4,5-tetrahydro-2H-3-benezazepin-2-on-3-yl]-3-chloro-propane and 1-(7-Benzyloxy-8-hydroxy-1,3,4,5-tetrahydro-2H-3-benzazepin-2-on-3-yl)-3-chloro-propane A solution of 19 gm (0.07 mol) of 1-(7,8-dihydroxy-1,3,4,5-tetrahydro-2H-3-benzazepin-2-on-3-yl)-3-chloro-propane and 10.6 gm of potassium carbonate in 250 ml of dimethyl sulfoxide was admixed with 19.5 gm (0.154 mol) of benzyl chloride. The mixture was stirred for 2 days at room temperature, then poured into ice water, and the aqueous mixture was extracted several times with ethyl acetate. The combined organic extracts were washed three times with water, dried over magnesium sulfate and evaporated in vacuo. The isomer separation was carried out on silica gel with methylene chloride and 3% of acetone as the eluant.

Yield of 7-hyroxy compound: 6 gm (23.8% of theory), M.p.: 163°-165° C.

Yield of 8-hydroxy compound: 4.5 gm (17.9% of theory), M.p.: 185°-165° C.

(c)

1-[7-Benzyloxy-8-hydroxy-1,3,4,5-tetrahydro-2H-3-benzazepin-2-on-3-yl]-3-[N-methyl-N-(2-{3,4-dimethoxy-phenyl}-ethyl)-amino]-propane This compound was prepared analogous to Example 5(b) by reacting 1-(7-benzyloxy-8-hydroxy-1,3,4,5-tetrahydro-2H-3-benzazepin-2-on-3-yl)-3-chloro-propane with N-methyl-N-[2-(3,4-dimethoxy-phenyl)-ethyl]-amine.
Yield: 75.4% of theory.
Melting point: 128°–129° C.

EXAMPLE 69

1-[7-Hydroxy-8-benzyloxy-1,3,4,5-tetrahydro-2H-3-benzazepin-2-on-3-yl]-3-[N-methyl-N-(2-{3,4-dimethyoxyphenyl}-ethyl)-amino]-propane This compound was prepared analogous to Example 5(b) by reacting 1-(7-hydroxy-8-benzyloxy-1,3,4,5-tetrahydro-2-H-3-benzazepin-2-on-3-yl)-3-chloro-propane with N-methyl-N-[2-(3,4-dimethoxy-phenyl)-ethyl]-amine.
Yield: 47.2% of theory.
Melting point: 157°–158° C.

EXAMPLE 70

1-[7,8-Dihydroxy-1,3,4,5-tetrahydro-2H-3-benzazepin-2-on-3-yl]-3-[N-methyl-N-(2-{3,4-dimethyoxy-phenyl}-ethyl)-amino]-propane 0.52 gm (0.001 mol) of 1-[7-hydroxy-8-benzyloxy-1,3,4,5-tetrahydro-2H-3-benzazepin-2-on-3-yl]-3-[N-methyl-N-(2-{3,4-dimethoxy-phenyl}-ethyl-amino]-propane were hydrogenated for 5 hours at 20° C. and 5 bar in 100 ml of methanol and in the presence of 0.2 gm of palladium-on-charcoal (10%). The catalyst was suction-filtered off; the filtrate was evaporated in vacuo, an the residue was purified on silica gel with methylene chloride+1% of ethanol as the eluant.
Yield: 0.2 gm (43.9% of theory).
IR-spectrum (methylene chloride): 3,520 cm$^{-1}$ (OH), 1,640 cm$^{-1}$ (CO).
$C_{24}H_{32}N_2O_5 \times \frac{1}{2}H_2O$, (455.5): Calc.: C-63.28%; H-7.74%; N-6.15%, Found: C-63.44%; H-7.77%; N-6.13%.

EXAMPLE 71

1-[7-Benzyloxy-8-methoxy-1,3,4,5-tetrahydro-2H-3-benzazepin-2-on-3-yl]-3-[N-methyl-N-(2-{3,4-dimethoxyphenyl}-ethyl)-amino]-propane dihydrochloride 0.52 gm (0.001 mol) of 1-[7-benzyloxy-8-hydroxy-1,3,4,5-tetrahydro-2H-3-benzazepin-2-on-3-yl]-3-[N-methyl-N-(2-{4-dimethyoxy-phenyl}-ethyl)-amino]-propane were dissolved in 30 ml of dimethyl formamide, and the solution was admixed with 50 mg of a 50% sodium hydride dispersion (in oil). The mixture was warmed for 30 minutes at 60° C., mixed with 0.1 ml of dimethyl sulfate and warmed for another 2 hours at 60° C. The dimethyl formamide was distilled off in vacuo; the residue was taken up in methylene chloride, and the organic phase was washed with water, dried and evaporated in vacuo. The resinous residue was purified on aluminum oxide (neutral, activity II) with methylene chloride as the eluant. The oil obtained was dissolved in acetone, and the dihydrochloride was precipitated by addition of ethereal hydrochloric acid.
Yield: 250 gm (41% of theory).
Melting point: 117°–120° C.

EXAMPLE 72

1-[7-Methoxy-8-benzyloxy-1,3,4,5-tetrahydro-2H-3-benzazepin-2-on-3-yl]-3-[N-methyl-N-(2-{3,4-dimethoxyphenyl}-ethyl)-amino]-propane This compound was prepared analogous to Example 71 by reacting 1-[7-hydroxy-8-benzyloxy-1,3,4,5-tetrahydro-2H-3-benzazepin-2-on-3-yl]-3-[N-methyl-N-(2-{3,4-dimethoxyphenyl}-ethyl)-amino]-propane with dimethyl sulfate.
Yield: 70% of theory.
IR-spectrum (methylene chloride): 1,655 cm$^{-1}$.
NMR-spectrum (CDCl$_3$/D$_2$O): δ=2.3 ppm, s, 3 H (NCH$_3$); 5.1 ppm, s, 2 H (benzyl.); 6.5–6.8 ppm, m, 5 H (aromat.); 7.4 ppm, s, 5 H (aromat.).

EXAMPLE 73

1-[7-Hydroxy-8-methoxy-1,3,4,5-tetrahydro-2H-3-benzazepin-2-on-3-yl]-3-[N-methyl-N-(2-{3,4-dimethoxyphenyl}-ethyl)-amino]-propane hydrochloride This compound was prepared analogous to Example 70 from 1-[7-benzyloxy-8-methoxy-1,3,4,5-tetrahydro-2H-3-benzazepin-2-on-3-yl]-3-[N-methyl-N-(2-{3,4-dimethoxyphenyl}-ethyl)-amino]-propane hydrochloride by catalytic debenzylation.
yield: 45.2% of theory.
IR-spectrum (methylene chloride): 3,530 cm$^{-1}$ (OH), 2,830 cm$^{-1}$ (OCH$_3$), 1,650 cm$^{-1}$ (CO).
$C_{25}H_{34}N_2O_5 \times HCl$, (479.0): Calc.: C-62.69%; H-7.36%; N-5.85%; Found: C-63.15%; H-7.57%; N-5.64%.

EXAMPLE 74

1-[7-Methyl-8-hydroxy-1,3,4,5-tetrahydro-2H-3-benzazepin-2-on-3-yl]-3-[N-methyl-N-(2-{3,4-dimethoxyphenyl}-ethyl)-amino]-propane This compound was prepared analogous to Example 70 from 1-[7-methoxy-8-benzyloxy-1,3,4,5-tetrahydro-2H-3-benzazepin-2-on-3-yl]-3-[N-methyl-N-(2-{3,4-dimethoxy-phenyl}-ethyl)-amino]-propane by catalytic debenzylation.
Yield: 29.4% of theory.
IR-spectrum (methylene chloride): 1,640 cm$^{-1}$ (CO).
$C_{25}H_{34}N_2O_5$, (442.56): Calc. C-67.85% H-7.74% N-6.33% ; Found: C-67.50% H-7.97% N-6.18%

EXAMPLE 75

1-[7,8-Dimethoxy-1,3,4,5-tetrahydro-2H-3-benzazepin-2-on-3-yl]-3-[N-methyl-N-(2-{3,4-dimethyl-phenyl}-ethyl)amino]-propane dihydrochloride This compound was prepared analogous to Example 5(b) by reaction of 1-(7,8-dimethoxy-1,3,4,5-tetrahydro-2H-3-benzazepin-2-on-3-yl)-3-chloro-propane with N-methyl-N-[2-(3,4-dimethyl-phenyl)-ethyl]-amine.
Yield: 54.3% of theory. Melting point: 170°–172° C.

EXAMPLE 76

1-7,8-Dimethoxy-1,3,4,5-tetrahydro-2H-3-benzazepin-2-on-3-yl]-3-[N-methyl-N-(2-{4-tert.butyl-phenyl}-ethyl)-amino]-propane dihydrochloride This compound was prepared analogous to Example 5(b) by reacting 1-(7-8-dimethoxy-1,3,4,5-tetrahydro-2H-3-benzazepin-2-on-3-yl)-3-chloro-propane with N-methyl-N-[2-(4-tert. butyl-phenyl)-ethyl]-amine.
Yield: 49.4% of theory.
Melting point: 146°–149° C.

EXAMPLE 77

1-[7,8-Dimethoxy-1,3,4,5-tetrahydro-2H-3-benzazepin-2-on-3-yl]-3-[N-methyl-N-(2-{4-n-butoxy-phenyl}-ethyl)amino]-propane This compound was prepared analogous to Example 5(b) by reaction of 1-(7,8-dimethoxy-1,3,4,5-tetrahydro- 2H-3-benzazepin-2-on-3-yl)-3-chloro-propane with N-methyl-N-[2-(4-n-butoxy-phenyl)-ethyl]-amine.
Yield: 55.3% of theory.
Melting point: 67°-69° C.

EXAMPLE 78

1-[7,8-Dimethoxy-1,3,4,5-tetrahydro-2H-3-benzazepin-2-on-3-yl]-3-[N-methyl-N-(2-{2,4,6-trimethoxyphenyl}-ethyl)-amino]-propane This compound was prepared analogous to Example 5(b) by reacting 1-(7,8-dimethoxy-1,3,4,5-tetrahydro-2H-3-benzazepin-2on-3-yl)-3-chloro-propane with [N-methyl-N-2-l -(2,4,6-trimethoxy-phenyl)-ethyl]-amine.
Yield: 57.8% of theory.
IR-spectrum (methylene chloride): 1,650 cm$^{-1}$ (CO), 1,520 cm$^{-1}$ (aromat. C=C).
$C_{27}H_{38}N_2O_6$ x HCl, (523.2): Calc.: C-62.00%; H-7.51%; N-5.35%, Cl-6.77%, Found: C-61.75%; H-7.52%; N-5.18%; Cl-7.34%.

EXAMPLE 79

1-[7,8-Dimethyl-1,3-dihydro-2H-3-benzazepin-2-on-3-yl]-3-[N-methyl-N-(2-{3,4-dimethoxy-phenyl}-ethyl)-amino]propane hydrochloride (a)
1-(7,8-Dimethyl-1,3-dihydro-2H-3-benzazepin-2-on-3-yl)-3-chloro-propane This compound was prepared analogous to Example 1(a) by reacting 7,8-dimethyl-1,3-dihydro-2H-3-benzazepin-2-one (m.p. 220°-224° C.) with 1-bromo-3-chloro-propane.
Yield: 99% of theory.
Melting point: 62°-64° C.

(b)
1-[7,8-Dimethyl-1,3-dihydro-2H-3-benzazepin-2-on-3-yl]-3-[N-methyl-N-(2-{3,4-dimethoxy-phenyl}ethyl)-amino]-propane hydrochloride This compound was prepared analogous to Example 1(b) by reacting 1-(7,8-dimethyl-1,3-dihydro-2H-3-benzazepin-2-on-3-yl)-3-chloro-propane with N-methyl-N-[2-(3,4-dimethoxy-phenyl)-ethyl]-amine.
Yield: 79.9% of theory.
Melting point: 105°-107° C.

EXAMPLE 80

1-[7,8-Dimethyl-1,3,4,5-tetrahydro-2H-3-benzazepin-2-on-3-yl]-3-[N-methyl-N-(2-{3,4-dimethoxy-phenyl}-ethyl)amino]-propane dihydrochloride This compound was prepared analogous to Example 4 by catalytic hydrogenation of 1-[7,8-dimethyl-1,3-dihydro-2H-3-benzazepin-2-on3-yl]-3-[N-methyl-N-(2-{3,4-dimethoxyphenyl}-ethyl)-amino]-propane.
Yield: 83.8% of theory.
Melting point: 154°-157° C.

EXAMPLE 81

1-[7,8-Dimethoxy-1,3,-dihydro-2H-3-benzazepin-2-on-3-yl]-2-methyl-3-[N-methyl-N-(2-{3,4-dimethoxyphenyl}-ethyl)-amino]-propane (a)
1-(7,8-Dimethoxy-1,3-dihydro-2H-3-benzazepin-2-on-3-yl)-2-methyl-3-chloro-propane This compound was prepared analogous to Example 1(a) by reacting 7,8-dimethoxy-1,3-dihydro-2H-3-benzazepin-2-one with 1-bromo-2-methyl-3-chloro-propane.
Yield: 97.5% of theory.
Melting point: 45°-47° C.

(b)
1-[7,8-Dimethoxy-1,3-dihydro-2H-3-benzazepin-2-on-3-yl]-2-methyl-2-[N-methyl-N-(2-{3,4-dimethoxyphenyl}-ethyl)-amino]-propane This compound was prepared analogous to Example 1(b) by reacting 1-(7,8-dimethoxy-1,3-dihydro-2H-3-benzazepin-2-on-3-yl)-2-methyl-3-chloro-propane with N-methyl-N-[2-(3,4-dimethoxy-phenyl)-ethyl]-amine.
Yield: 36% of theory.
Melting point: 30°-32° C.

EXAMPLE 82

1-[7,8-Dimethoxy-1,3,4-tetrahydro-2H-3-benzazepin-2-on-3-yl]-2-methyl-3-[N-methyl-N-(2-{3,4-dimethoxyphenyl}-ethyl)-amino]-propane hydrochloride This compound was prepared analogous to Example 4 by catalytic hydrogenation of 1-[7,8-dimethoxy-1,3-dihydro-2H-3-benzazepin-2-on-3-yl]-2-methyl-3-[N-methyl-N-(2-{3,4-dimethoxy-phenyl}-ethyl)-amino]-propane.
Yield: 73.7% of theory.
Melting point 99°-101° C.

EXAMPLE 83

1-[7,8-Dimethoxy-1,3,4,5-tetrahydro-2H-3-benazaepine-1,2-dione-3-yl]-3-[N-methyl-N-(2-{3,4-dimethoxyphenyl}-ethyl)-amino]-propane hydrochloride 3 gm of sodium dichromate x 2 H$_2$O were added to 2.45 gm (0.005 mol) of 1-[7,8-dimethoxy-1,3,4,5-tetrahydro-2H-3-benzazepin-2-on-3-yl]-3-[N-methyl-N-(2-{3,4-dimethoxyphenyl}-ethyl)-amino]-propane hydrochloride in 50 ml of glacial acetic acid. The mixture was stirred for 2 hours at room temperature, poured into ice water, and the aquoeus mixture was neutralized with potassium carbonate and extracted several times with methylene chloride. The organic extracts were dried over magnesium sulfate and evaporated in vacuo. The residue was purified on a silica gel column with methylene chloride +1% of ethanol as the eluant. The product thus obtained was dissolved in acetone, and the hydrochloride was precipitated with ethereal hydrochloric acid.
Yield: 1.3 gm (51.3% of theory).
Melting point: 197°-187° C.

EXAMPLE 84

1-[7,8-Dimethoxy-1,3,4,5-tetrahydro-2-H-3-benzazepine-1,2-dione-3-yl]-3-[N-methyl-N-(2-{3,4-dimethoxyphenyl]-ethyl)-amino]-propane hydrochloride 1.98 gm (4.0 mmols) of 1-[7,8-dimethoxy-1,3,4,5-tetrahydro-2H-3-benzazepin-2-on-3-yl]-3-[N-methyl-N-(2-{3,4-dimethoxy-phenyl}-ethyl)-amino]-propane hydrochloride were suspended in 50 ml of acetic anhydride; the suspension was mixed with 2.5 gm of potassium permanganate, and the mixture was stirred for 20 minutes at 20° C. The reaction mixture was poured into ice water and made alkaline with concentrated ammonia. The precipitated manganese dioxide was suction-filtered off, and the filtrate was extracted several times with methylene chloride. The extract was dried over magnesium sulfate, evaporated in vacuo, and the residue was purified on a silica gel column with methylene chloride +1% of ethanol as the eluant. The product thus obtained was dissolved in acetone, and the hydrochloride was precipitated with ethereal hydrochloric acid.

Yield: 0.7 gm (34.5% of theory).
Melting point: 196°–197° C.

EXAMPLE 85

1-[6,9-Dimethoxy-1,3-dihydro-2H-3-benzazepin-2-on-3-yl]-3-[N-methyl-N-(2-{3,4-dimethoxy-phenyl}-ethyl)-amino]-propane (a)

1-(6,9-Dimethoxy-1,3-dihydro-2H-3-benzazepin-2-on-3-yl)-3-chloro-propane

This compound was prepared analogous to Example 1(a) by reacting 6,9-dimethoxy-1,3-dihydro-2H-3-benzazepin-2-one (m.p. 188°–191° C.) with 1-bromo-3-chloro-propane.

Yield: 27% of theory.
Melting point: 97°–99° C.

(b)

1-[6,9-Dimethoxy-1,3-dihydro-2H-3-benzazepin-2-on-3-yl]-3-[N-methyl-N-(2-{3,4-dimethoxyphenyl}-ethyl)-amino]-propane This compound was prepared analogous to Example 1(b) by reacting 1-(6,9-dimethoxy-1,3-dihydro-2H-3-benzazepin-2-on-3-yl)-3-chloro-propane with N-methyl-N-[2-(3,4-dimethoxy-phenyl)-ethyl]-amine.

Yield: 90% of theory.
IR spectrum (methylene chloride): 1658 cm$^{-1}$ (CO).
NMR-spectrum (CDCl$_3$/D$_2$O): $\delta = 2.2$ ppm, s, 3H (NCH$_3$); 3.7–3.8 ppm, 4s, 12 H (OCH$_3$); 6.25 ppm, d (J=9 Hz), 1H (olefin.).

EXAMPLE 86

1-[6,9-Dimethoxy-1,3,4,5-tetrahydro-2H-benzazepin-2-on-3-yl]-3-[N-methyl-N-(2-{3,4-dimethoxy-phenyl}-ethyl)-amino]-propane hydrochloride This compound was prepared analogous to Example 4 by catalytic hydrogenation of 1-[6,9-dimethoxy-1,3-dihydro-2H-3-benzazepin-2-on-3-yl]-3-[N-methyl-N-(2-{3,4-dimethoxy-phenyl}-ethyl)-amino]-propane.
yield: 85% of theory.
Melting Point: 73°–76° C.

EXAMPLE 87

1-[8,9-Dimethoxy-1,3-dihydro-2H-3-benzazepin-2-on-3-yl]-3-[N-methyl-N-(2-{3,4-dimethoxy-phenyl}-ethyl)-amino]propane hydrochloride (a)

1-(8,9-Dimethoxy-1,3-dihydro-2H-3-benzazepin-2-on-3-yl)-3-chloro-propane

This compound was prepared analogous to Example 1(a) by reacting 8,9-dimethoxy-1,3-dihydro-2H-3-benzazepin-2-one (m.p.: 165°–168° C.) with 1-bromo-3-chloro-propane.

Yield: 45% of theory.
Melting point: 67°–71° C.

(b)

1-[8,9-Dimethoxy-1,3-dihydro-2H-3-benzazepin-2-on-3yl]-3-[N-methyl-N-(2{3,4dimethoxy-phenyl}-ethyl)-amino]-propane hydrochloride This compound was prepared analogous to Example 1(b) by reacting 1-(8,9-dimethoxy-1,3-dihydro-2H-3-benzazepin-2on-3yl)-3-chloro-propane with N-methyl-N-[2-(3,4-dimethoxy-phenyl)-ethyl]-amine.

Yield: 64% of theory.
Melting point: 64°–68° C.

EXAMPLE 88

1-[8,9-Dimethoxy-1,3,4,5-tetrahydro-2H-3-benzazepin-2-on-3-yl]-3-[N-methyl-N-(2-{3,4-dimethoxy-phenyl}-ethyl)amino]-propane hydrochloride This compound was prepared analogous to Example 4 by catalytic hydrogenation of 1-[8,9-dimethoxy-1,3-dihydro-2H-3-benzazepin-2-on-3-yl]-3-[N-methyl-N-(2-{3,4-dimethoxyphenyl}-ethyl)-amino]-propane.

Yield: 75% of theory.
Melting point: 131°–133° C.

EXAMPLE 89

1[7,8-Dimethoxy-1,3,4,5-tetrahydro-2H-3-benzazepin-2-on-3-yl]-3-[N-methyl-N-(2-{3,4,5-trimethoxy-phenyl}-ethyl)-amino]-propane hydrochloride This compound was prepared analogous to Example 5(b) by reacting 1-(7,8-dimethoxy-1,3,4,5-tetrahydro-2H-3-benzazepin-2-on-3-yl)-chloro-propane with N-methyl-N-[2-(3,4,5-trimethoxy-phenyl)-ethyl]-amine.

Yield: 44% of theory.
Melting point: 131° (decomp.).

EXAMPLE 90

Isomeric mixture of
1-[7,8-Dimethoxy-1,3,4,5-tetrahydro-2H-3-benzazepin-2-on-3-yl]-3-[N-methyl-N-(2-{2- and 4-nitro-phenyl}-ethyl)-amino]-propane This mixture was prepared analogous to Example 1(b) from 1-[7,8-dimethoxy-1,3,4,5-tetrahydro-2H-3-benzazepin-2-on-3-yl]-3-chloro-propane and N-methyl-N-[2-(2- and 4-nitro-phenyl)-ethyl]-amine.

Yield: 72% of theory.
IR-spectrum (methylene chloride): 1,650 cm$^{-1}$ (CO).

EXAMPLE 91

Isomeric mixture of
1-[7,8-Dimethoxy-1,3,4,5-tetrahydro-2H-3-benzazepin-2-on-3-yl]-3-[N-methyl-N-(2-{2- and 4-amino-phenyl}-ethyl)-amino]-propane This mixture was prepared analogous to Example 4 by catalytic hydrogenation of an isomeric mixture of 1-[7,8-dimethoxy-1,3,4,5-tetrahydro-2H-benzazepin-2-on-3-yl]-3-[N-methyl-N-(2-{2- and 4-nitro-phenyl}-ethyl)-amino]-propane.

Yield: 81% of theory.
IR-spectrum (methylene chloride): 1,645 cm$^{-1}$ (CO).

EXAMPLE 92

1-[7,8-Dimethoxy-1,3,4,5-tetrahydro-2H-3-benzazepin-2- on-3-yl]-3-8 N methyl-N-(2-{2-acetylamino-phenyl}-ethyl-amino]-propane hydrochloride and 1-[7,8-Dimethoxy-1,3,4,5-tetrahydro-2H-3-benzazepin-2-on-3-yl]-3-[N-methyl-N-(2-{4-acetylamino phenyl}-ethyl)-amino]-propane hydrochloride These compounds were prepared analogous to Example 52 by reacting an isomeric mixture of 1-[7,8-dimethoxy-1,3,4,5-tetrahydro-2H-3-benzazepin-2-on-3-yl]-3-[N-methyl-N-(2-{2- and 4-amino-phenyl}-ethyl)-amino]propane with glacial acetic acid and acetic acid anhydride.

Yield of 2-acetylamino compound: 26% of theory, M.p.: 102°–105° C. (decomp.).

Yield of 4-acetylamino compound: 49% of theory. M.p.: 89°–93° C.

EXAMPLE 93

1-[7,8-Dimethoxy-1,3,4,5-tetrahydro-2H-3-benzazepin-2-on-3-yl]-3-[N-methyl-N-(2-{4-amino-phenyl}-ethyl)-amino]-propane 4.85 gm (0.0107 mol) of 1-[7,8-dimethoxy-1,3,4,5-tetrahydro-2H-3-benzazepin-2-on-3-yl]-3-[N-methyl-N-(2-{4-acetylamino-phenyl}-ethyl)-amino]-propane were stirred for 34 hours at 40° C. with 80 ml of methanolic hydrochloric acid. After evaporating the solution, the residue was dissolved in methylene chloride, extracted with aqueous sodium bicarbonate, and washed with water. The organic phase was dried and evaporated in vacuo, and the residual oil was dried at 50° C. in vacuo.

Yield: 88% of theory.

IR-spectrum (methylene chloride): 1,645 cm$^{-1}$ (CO) NMR-spectrum (CDCl$_3$/D$_2$O): 67 =2.25 ppm, s, 3H (NCH$_3$); 3.8 ppm, s, 12H (OCH$_3$); 6.9 ppm, d (J=7Hz) 2H (aromat.).

EXAMPLE 94

1-[7,8-Dimethoxy-1,3,4,5-tetrahydro-2-H-3-benzazepin-2-on-3-yl]-3-[N-methyl-N-(2-{4-chloro-phenyl}-ethyl)amino]-propane dihydrochloride 1.01 gm (0.00245 mol) of 1-[7,8-dimethoxy-1,3,4,5-tetrahydro-2H-3-benzazepin-2-on-3-yl]-3-[N-methyl-N-(2{4-amino-phenyl}-ethyl)-amino]-propane were dissolved in 5 ml of semi-concentrated hydrochloric acid, and the solution was diazotized with 0.17 gm (0.00245 of sodium nitrite. Subsequently, the solution was stirred at 55° C. until no more nitrogen escaped. The solution was made weakly alkline and extracted with methylene chloride. After drying and evaporating in vacuo, the residueal oil was purified on aluminum oxide (200 gm, neutral, activity II; eluant: methylene chloride +2% of ethanol) and the dihydrochloride was precipitated from acetone with ethereal hydrochloric acid.

Yield: 21% of theory.

Melting point: 148°–151° C.

EXAMPLE 95

1-[7,8-Dimethoxy-2,3-dihydro-1H-3-benzazepin-3-yl]-3-[N-methyl-N-(2-{3,4-dimethoxy-phenyl}-ethyl)-amino]-propane 2.3 gm (0.005 mol) of 1-[7,8-dimethoxy-1,3-dihydro-2H-3-benzazepin-2-on-3yl]-3-[N-methyl-N-(2-{3,4-dimethoxy-phenyl}-ethyl)-amino]-propane were dissolved in 150 ml of absolute ether; the solution was mixed with 0.6 gm of lithium aluminum hydride, and the mixture was stirred for 2 hours at room temperature. While cooling with ice, a 10% ammonium chloride solution was added; the precipitate formed was suction-filtered off, and the solvent was removed from the filtrate in vacuo. The oily residue was purified on aluminum oxide (neutral, activity II) with methylene chloride as the eluant.

Yield: 1.6 gm (72.7% of theory).

IR-spectrum (methylene chloride): 2,830 cm$^{-1}$ (OCH$_3$), 2,790 cm$^{-1}$ (N-alkyl).

C$_{26}$H$_{36}$N$_2$O$_4$, (440.6); Calc,: C-70.88%; H-8.24%; N-6.35%; Found: C-70.50%; H-8.80%; N-6.22%.

EXAMPLE 96

1-[7,8-Dimethoxy-1,3,4,5-tetrahydro-2H-3-benzazepin-2-on-3yl]-3-[N-methyl-N-(2-{4-hydroxy-phenyl}ethyl)-amino]-propane hydrochloride 1.1 gm (2.67 mmols) of 1-[7,8-dimethoxy-1,3,4,5-tetrahydro-2H-3-benzazepin-2on-3-yl]-3-[N-methyl-N-(2-{4-amino-phenyl}-ethyl)-amino]-propane were dissolved in 10 ml of semi-concentrated sulfuric acid, and the solution was diazotized at 0° C. with 0.18 gm (2.67 mmols) of sodium nitrite. The solution was heated on a steam bath for 20 minutes, diluted with water, made weakly alkaline with sodium hydroxide and extracted with methylene chloride. After drying and evaporating the organic extract in vacuo, the residual oil was purified on 100 gm of aluminum oxide (neutral, activity II) with methylene chloride +2% of ethanol as the eluant. The hydrochloride was precipitated from acetone with ethereal hydrochloric acid.

Yield: 0.17 gm (15% of theory).

Melting point: 109°–112° C. (decomp.).

EXAMPLE 97

1-[7,8-Dimethoxy-1,3,4,5-tetrahydro-2H-3-benzazepin-2-on-3-yl]-3-[N-methyl-N-(2-{4-dimethylamino-phenyl}ethyl)-amino]-propane dihydrochloride This compound was prepared analogous to Example 11 by reacting 1-[7,8-dimethoxy-1,3,4,5-tetrahydro-2H-3-benzazepin-2-on-3-yl]-3-[N-methyl-N-(2-{4-amino-phenyl}-ethyl)-amino]-propane with 37% formalin solution and sodium cyanoborohydride.

Yield: 40% of theory.

Melting point: 193°–196° C.

EXAMPLE 98

1-[7,8-Dimethoxy-1,3,4,5-tetrahydro-2H-1,3-benzodiazepin-2-on-3-yl]-3-[N-methyl-N-(2-{4-amino-3,5-dichloro-phenyl}-ethyl)-amino]-propane (a)

N-[3-[N'-Methyl-N'-(2-{4-amino-3,5-dichloro-phenyl}-ethyl)-amino]-propyl]-N-[2-(2-amino-4,5-dimethoxy-phenyl)-ethylamine]hydrochloride This compound was prepared analogous to Example 53(a) from N-[3-[N'-methyl-N'-(2-{4-amino-3,5-dichloro-phenyl}-ethyl)-amino]-propyl]-2-(2-amino-4,5-dimethoxy-phenyl)-acetamide and lithium aluminum hydride.

Melting point: 182°–188° C. (decomp.).

(b)

1-[7,8-Dimethoxy-1,3,4,5-tetrahydro-2H-1,3-benzodiazepin-2-on-3yl]-3-[N-methyl-N-(2-{4-amino-3,5-dichloro-phenyl}-ethyl)-amino]-propane This compound was prepared analogous to Example 53(b) from N-[3-[N'-methyl-N'-(2-{4-amino-3,5-dichloro-phenyl}-ethyl)-amino]-propyl]-N-[2-(2-amino- 4,5-dimethoxy-phenyl)-ethyl]-amine hydrochloride and N,N'-carbonyl-diimidazole.

Melting point: 163°-166° C.

EXAMPLE 99

1-[7,8-Dimethoxy-1,3,4,5-tetrahydro-2H-3-benzazepin-1,2-dione-3-yl]-3-[N-methyl-N-(2-{4-amino-3,5-dichloro-phenyl}-ethyl)-amino]-propane This compound was prepared analogous to Example 5(b) from 1-[7,8dimethoxy-1,3,4,5-tetrahydro-2H-3-benzazepin- 2-on-3-yl]-3-[N-methyl-N-(2-{4-amino-3,5-dichloro-phenyl}-ethyl)-amino]-propane and selenium dioxide.

Melting point: 118°-130° C. m/e=493/495 ($C_{24}H_{29}Cl_2N_3O_4$: 494.43).

EXAMPLE 100

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane-dihydrochloride 1.1 gm (5.0 mmols) of 7,8-dimethoxy-1,3,4,5-tetrahydro-2H-3-benzazepin-2-one were suspended in 20 ml of dimethyl sulfoxide, and the suspension was mixed with 0.6 gm (5.3 mmols) of potassium tert. butylate while stirring. After 10 minutes, the solution was mixed with 2.0 gm (7.4 mmols) of 1-chloro-3-[N-methyl-N-(2-{3,4-dimethoxy-phenyl}-ethyl)-amino]-propane; the mixture was stirred for one hour at 50° C. and then poured into water; the aqueous mixture was extracted with ethyl acetate, and the organic phase was evaporated in vacuo. The residue was purified on silica gel with methylene chloride +10% of methanol as the eluant, and the dihydrochloride was precipitated from acetone with ethereal hydrochloric acid.

Melting point: 136°-137° C.

EXAMPLE 101

1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane dihydrochloride.

This compound was prepared analogous to Example 100 from 7,8-dimethoxy-1,3,4,5-tetrahydro-2H-3-benzazepin- -2-one and N-methyl-N-(2-{3,4- dimethoxy-phenyl}-ethyl)-azetidinium bromide.

Melting point: 137° C.

EXAMPLE 102

1-[7,8-Dimethoxy-1,3,4,5-tetrahydro-2H-3-benzazepin-2-on-3-yl]-3-[N-methyl-N-(2-{3-amino-4-chloro-phenyl}-ethyl)-amino]-propane This compound was prepared analogous to Example 12 by reacting N-[3-(7,8-dimethoxy-1,3,4,5-tetrahydro-2H-3-benzazepin-2-on-3-yl)-propyl]-methylamine with 2-(3-amino-4-chloro-phenyl)-ethyl chloride. Oil.

UV-spectrum (ethanol): λ max: 238 nm (0.26), 285 nm (0.19), 304 nm (0.06).

IR-spectrum (dichloromethane): 3,390 and 3,480 cm$^{-1}$ (NH$_2$), 1,650 cm$^{-1}$ (CO), 2,830 cm$^{-1}$ (OCH$_3$), 2,795 cm$^{-1}$ (CH3-N<), 1,520 and 1,620 cm$^{-1}$ (C=C).

EXAMPLE 103

1-[7,8-Dimethoxy-1,3,4,5-tetrahydro-2H-3-benzazepin-2-on-3-yl]-3-[N-allyl-N-(2-{4-amino-3,5-dichloro-phenyl}-ethyl)-amino]-propane This compound was prepared analogous to Example 12 from N-[3-(7,8-dimethoxy-1,3,4,5-tetrahydro-2H-3-benzazepin-2-on-3-yl)-propyl]-allylamine and 2-(4-amino-3,5-dichloro-phenyl)-ethyl chloride. Oil.

IR-spectrum (methylene chloride): 3,400 3,495 cm$^{-1}$ (NH$_2$), 1,655 cm$^{-1}$ (CO).

EXAMPLE 104

1-[7,8-Dimethoxy-1,3,4,5-tetrahydro-2H-3-benzazepin-2-on-3-yl]-3-[N-methyl-N-(2{3,5-dichloro-4-formylamino-phenyl}-ethyl)-amino]-propane This compound was prepared analogous to Example 14 from 1-[7,8-dimethoxy-1,3,4,5-tetrahydro-2H-3-benzazepin-2-on-3-yl]-3-[N-methyl-N-(2-{4-amino-3,5-dichloro-phenyl}-ethyl)-amino]-propane and formic acid/formaldehyde.

IR-spectrum (methylene chloride): 3,410 cm$^{-1}$ (NH), 1,710 cm$^{-1}$ (NH-CO), 1,655 cm$^{-1}$ (CO).

UV-spectrum (ethanol): λ max: 240 nm (shoulder, 0.13) 275-285 nm (0.6).

EXAMPLE 105

1-[7,8-Dimethoxy-1,3,4,5-tetrahydro-2H-3-benzazepin-2-on-3-yl]-3-[N-methyl-N-(2-{4-amino-3-bromo-5-cyano-phenyl}-ethyl)-amino]-propane This compound was prepared analogous to Example 5(b) from 1-[7,8-dimethoxy-1,3,4,5-tetrahydro-2H-3-benzazepin-2-on-3-yl]-3-chloro-propane and 2-(4-amino-3-bromo-5-cyano-phenyl)-N-methyl-ethylamine.

Melting point: 75-85° C.

EXAMPLE 106

1-[7,8-Dimethoxy-1,3,4,5-tetrahydro-2H-3-benzazepin-2-on-3-yl]-3-[N-propyl-N-(2-{4-amino-3,5-dichloro-phenyl}-ethyl)-amino]-propane This compound was prepared analogous to Example 5(b) from 1-[7,8-dimethoxy-1,3,4,5-tetrahydro-2H-3-benzazepin-2-on-3-yl]-3-chloropropane and 2-(4-amino-3,5-dichloro-phenyl)-N-propyl-ethylamine. Oil.

IR-spectrum (methylene chloride): 3,380, 3,495 cm$^{-1}$ ($NH_2$), 1,650 cm$^{-1}$ (CO).

UV-spectrum (ethanol): λ max: 240 nm (shoulder, 0.13), 280-290 nm (0.05).

EXAMPLE 107

1-[7,8-Dimethoxy-1,3,4,5-tetrahydro-2H-3-benzazepin-2-on-3-yl]-3-[N-methyl-N-(2-{4-amino-3-chloro-5-cyano-phenyl}-ethyl)-amino]-propane This compound was prepared analogous to Example 5(b) from 1-[7,8-dimethoxy-1,3,4,5-tetrahydro-2H-3-benzazepin-2-on-3-yl]-3-chloro-propane and 2-(4-amino-3-chloro-5-cyano-phenyl)-N-methyl-ethylamine.

Melting point: 75°-90° C.

EXAMPLE 108

1-[7,8-Dimethoxy-1,3,4,5-tetrahydro-2H-3-benzazepin-2-on-3-yl]-3-[N-methyl-N-(2-{4-amino-3-cyano-phenyl}-ethyl)-amino]-propane This compound was prepared analogous to Example 5(b) from 1-[7,8-dimethoxy-1,3,4,5-tetrahydro-2H-3-benzazepin-2-on-3-yl]-3-chloro-propane and 2-(4-amino-3-cyano-phenyl)-N-methyl-ethylamine.

Melting point: Commencing at 80° C.

IR-spectrum (methylene chloride): 2,210 cm$^{-1}$ (CN), 1,635 cm$^{-1}$ (CO).

UV-spectrum (ethanol): λ max: 248 nm (shoulder, 0.1), 283 nm (0.04), 320 nm (0.04).

EXAMPLE 109

1-[7,8-Dimethoxy-1,3,4,5-tetrahydro-2H-3-benzazepin-2-on-3-yl]-3-[N-methyl-N-(2-phenyl-ethyl)-amino]-propane dihydrochloride This compound was prepared analogous to Example 5(b) by reacting 1-[7,8-dimethoxy-1,3,4,5-tetrahydro-2H-3-benzazepin-2-on-3-yl]-3-chloropropane with N-methyl-2-phenyl-ethylamine.

Yield: 43.2% of theory.
Melting point: 165° C. (decomp.).

EXAMPLE 110

1-[7,8-Dimethoxy-1,3,4,5-tetrahydro-2H-3-benzazepin-2-on-3-yl]-3-[N-methyl-N-(2-{4-amino-3-nitro-phenyl}-ethyl)-amino]-propane hydrochloride 1.0 gm (1.75 mmols) of 1-[7,8-dimethoxy-1,3,4,5-tetrahydro-2H-3-benzazepin-2-on-3-yl]-3-[N-methyl-N-(2-{4-acetamino-3-nitro-phenyl}-ethyl)-amino]-propane was heated in 50 ml of methanolic hydrochloric acid for two hours at 45°–50° C. The reaction solution was then evaporated; the residue was dissolved in methylene chloride; the solution was washed with a saturated aqueous sodium bicarbonate solution and dried over magnesium sulfate, and the solvent was distilled off in vacuo. After purification of the residue on silica gel with methylene chloride and 5% ethanol as the eluant, the hydrochloride was precipitated from acetone by addition of ethereal hydrochloric acid.

Yield: 0.4 gm (43.1% of theory).
Melting point: 207°–208° C. (decomp.).

EXAMPLE 111

1-[7,8-Dimethoxy-1,3,4,5-tetrahydro-2H-3-benzazepin-2-on-3-yl]-3-[N-methyl-N-(3-{3,4-dimethoxy-phenyl}-propyl)-amino]-propane hydrochloride (a)
1-[7,8-Dimethoxy-1,3,4,5-tetrahydro-2H-3-benzazepin-2-on-3-yl]-3-chloro-propane 1.1 gm (0.005 mol) of 7,8-dimethoxy-1,3,4,5-tetrahydro-2H-3-benzazepin-2-one were suspended in 15 ml of absolute dimethylsulfoxide, and the suspension was mixed with 0.67 gm (0.006 mol) of potassium tert. butoxide, while stirring. After 10 minutes, the suspension thus obtained was added dropwise to 0.64 ml (0.006 mol) of 1-bromo-3-chloro-propane in 10 ml of dimethylsulfoxide, while cooling with ice water. After one hour the mixture was poured into water. After a short time the viscous precipitate began to crystallize. The precipitate was suction-filtered off, dissolved in acetone, precipitated again with water, and then suction-filtered off and dried Yield: 0.75 gm (50.0% of theory).
Melting point: 84°–85° C.

(b)
1-[7,8-Dimethoxy-1,3,4,5-tetrahydro-2H-3-benzazepin-2-on-3-yl]-3-[N-methyl-N-(3-{3,4-dimethoxy-phenyl}-propyl)-amino]-propane hydrochloride A mixture of 5.55 gm (0.0186 mol) of 1-[7,8-dimethoxy-1,3,4,5-tetrahydro-2H-3-benzazepin-2-on-3-yl]-3-chloro-propane, 2.6 ml (0.0886 mol) of triethylamine and 3.9 gm (0.0186 mol) of N-methyl-3-(3,4-dimethoxyphenyl) propylamine was heated at 85° C. for 4 hours, then cooled and dissolved in methylene chloride/water. The organic phase was separated, extracted with water, dried over magnesium sulfate, concentrated by evaporation in vacuo, and the residue was purified on silica gel, using methylene chloride plus 3% ethanol as the eluant. The oily free base product thus obtained was dissolved in acetone, and the hydrochloride was precipitated with ethereal hydrochloric acid.

Yield: 3.45 gm (36.6% of theory).
Melting point: 220–221° C.

EXAMPLE 112

1-[7,8-Dimethoxy-1,3,4,5-tetrahydro-2H-3-benzazepin-2on-yl]-3-[N-methyl-N-(2-phenyl-ethyl)-amino] propane dihydrochloride This compound was prepared analogous to Example 111(b) by reacting 1-[7,8-dimethoxy-1,3,4,5-tetrahydro-2H-3-benzazepin-2-on-3-yl]-3chloro-propane with N-methyl-2-phenyl-ethylamine.

Yield: 43.2% of theory.
Melting point: 165° C. (decomp.).

EXAMPLE 113

1-[1,3,4,5-Tetrahydro-2H-3-benzazepin-2-on-3-yl]-3-[N-methyl-N-(2-{3,4-dimethoxy-phenyl{-ethyl) amino}-propane hydrochloride (a)
1-[1,3,4,5-Tetrahydro-2H-3-benzazepin-2-on-3-yl]-3-chloro-propane This compound was prepared analogous to Example 111(a) by reacting 1,3,4,5-tetrahydro-2H-3-benzazepin-2-one with 1-bromo-3-chloro-propane.

Yield: 13.4% of theory.
IR-spectrum (methylene chloride): 1,660 cm$^{-1}$ (CO).

(b)
1-[1,3,4,5-Tetrahydro-2H-3-benzazepin-2-on-3-yl]-3-[N-methyl-N-(2-{3,4-dimethoxy-phenyl}-ethyl)-amino-propane hydrochloride This compound was prepared analogous to Example 111(b) by reacting 1-[1,3,4,5-tetrahydro-2H-3-benzazepin-2-on-3-yl]-3-chloro-propane with N-methyl-N-(2-[3,4-dimethoxy-phenyl]-ethyl)-amine.

Yield: 29.2% of theory.
Melting point: 160–162° C.

EXAMPLE 114

1-[7,8-Dimethoxy-1,3-dihydro-2H-3-benzazepin-2-on-3-yl]-3-[N-methyl-N-(5-{3,5-dimethoxy-phenyl}-pentyl)-amino]-propane hydrochloride (a)
1-[7,8-Dimethoxy-1,3-dihydro-2H-3-benzazepin-2-on-3-yl]-3-chloro-propane This compound was prepared analogous to Example 111(a) by reacting 7,8-dimethoxy-1,3-dihydro-2H-3-benzazepin-2-one with 1-bromo-3-chloro-propane.

Yield: 87.3% of theory.
Melting point: 101°–103° C.

(b)
1-[7,8-Dimethoxy-1,3-dihydro-2H-benzazepin-2-on-3-yl]-3[N-methyl-N-(5-{3,4-dimethoxy-phenyl}-pentyl)-amino]-propane hydrochloride This compound was prepared analogous to Example 111(b) by reacting 1-[7,8-dimethoxy-1,3-dihydro-2H-3-benzazepin-2-on-3-yl]-3-chloro-propane with N-methyl-N-(5-[3,4-dimethoxy-phenyl]-pentyl)-amine.

Yield: 67.3% of theory.

Melting point: 158°–160° C.

EXAMPLE 115

1-[7,8-Dimethoxy-1,3,4,5-tetrahydro-2H-3-benzazepin-2-on-3-yl]-3-[N-methyl-N-(5-{3,4-dimethoxy-phenyl}-pentyl)-amino]-propane hydrochloride A solution of 3.23 gm (0.0065 mol) of 1-[7,8-dimethoxy-1,3-dihydro-2H-3-benzazepin-2-on-3-yl]-3-[N-methyl-N-(5-{3,4-dimethoxy-phenyl}-pentyl)-amino]-propane in 30 ml of acetic acid was hydrogenated at room temperature under a hydrogen pressure of 5 bar in the presence of 10% palladium-on-charcoal for 3.5 hours. The catalyst was then filtered off; the filtrate was concentrated by evaporation in vacuo, and the residue was taken up in methylene chloride/15% potassium carbonate solution. The organic phase was separated, dried over magnesium sulfate, and concentrated in vacuo, in a rotary evaporator and the residue was purified on silica gel using methylene chloride plus 4% ethanol as the eluant. The free base product thus obtained was dissolved in acetone, and the hydrochloride was precipitated with ethereal hydrochloric acid.

Yield: 2.1 gm (60.3% of theory).
Melting point: 165°–166° C.

EXAMPLE 116

1-[7,8-Dimethoxy-1,3,4,5-tetrahydro-2H-3-benzazepin-2-thion-3-yl]-3-[N-methyl-N-(2-{3,4-dimethoxyphenyl} ethyl)-amino]-propane 2.28 gm (0.005 mol) of 1-[7,8-dimethoxy-1,3,4,5-tetrahydro-2H-3-benzazepin-2-on-3-yl]-3-[N-methyl-N-(2-{3,4-dimethoxy-phenyl}-ethyl)-amino]-propane were dissolved in 10 ml of absolute toluene, and the solution was refluxed for 50 minutes with 1.0 gm (0.0025 mol) of 2,4-bis-(4-methoxy-phenyl)-1,3-dithia-2,4-diphosphetane-2,4-disulfide. After the solvent had been removed in vacuo in a rotary evaporator, the residue was purified on aluminium oxide with methylene chloride plus 2% ethanol as the eluant.

Yield: 1.45 gm (61.4% of theory).
$C_{26}H_{36}N_2O_4S$, (472.6): Calculated: C-66.07%; H-7.68%; N-5.93%; S-6.78%; Found: C-66.10%; H-7.71%; N-5.56%; S-6.76%;

EXAMPLE 117

1-[7,8-Dimethoxy-1,3,4,5-tetrahydro-2H-3-benzazepin-2-on-3-yl]-3-[N-methyl-N-(3,4-dimethoxy-benzoyl-methyl)-amino]-propane hydrochloride This compound was prepared analogous to Example 111(b) by reacting 1-[7,8-dimethoxy-1,3,4,5-tetrahydro-2H-3-benzazepin-2-on-3-yl]-3-N-methyl-amino-propane with α-bromo-3,4-dimethoxy-acetophenone.

Yield: 1.29 gm (77.0% of theory).
Melting point: 190° C.

EXAMPLE 118

1-[7,8-Dimethoxy-1,3,4,5-tetrahydro-2H-3-benzazepin-2-on-3-yl]-3-[N-methyl-N-(2-hydroxy-2-{3,4-dimethoxy-phenyl}-ethyl)-amino]-propane 0.92 gm (0.002 mol) of 1-[7,8-dimethoxy-1,3,4,5-tetrahydro-2H-3-benzazepin-2-on-3-yl]-3-[N-methyl-N-(3,4-dimethoxy-benzoyl-methyl)-amino]-propane were dissolved in 6 ml of ethanol; the solution was mixed with 0.38 gm (0.01 mol) of sodium borohydride, and the mixture was stirred for 2 hours at 25° C. After the solvent had been evaporated in vacuo, the residue was dissolved in methylene chloride, and the solution was extracted with water, dried over magnesium sulfate and concentrated by evaporation in vacuo. The residue was purified on aluminium oxide, using methylene chloride plus 1% ethanol as the eluant.

Yield: 0.5 gm (54% of theory).
IR-spectrum (methylene chloride): 1,655 cm$^{-1}$ (CO).
$C_{26}H_{36}N_2O_6$, (472.6): Calculated: C-66.08%; H-7.68%; N-5.93%, Found: C-66.01%; H-7.62%; N-5.80%.

EXAMPLE 119

1-[7,8-Dimethoxy-1-(2-{3,4-dimethoxy-phenyl}-ethylamino)-1,3,4,5-tetrahydro-2H-3-benzazepin-2-on-3-yl]-3-[N-methyl-N-(2-{3,4-dimethoxy-phenyl}-ethyl)-amino]-propane dihydrochloride A mixture of 2.45 gm (5 mmols) of 1-[7,8-dimethoxy-1,3,4,5-tetrahydro-2H-3-benzazepin-1,2-dion-3-yl]-3-[N-methyl-N-(2-{3,4-dimethoxy-phenyl}-ethyl-amino]-propane and 2 gm of 2-(3,4-dimethoxy-phenyl)-ethylamine was heated at 150° C. for 3 hours. The reaction mixture was purified on aluminum oxide N (activity II), using methylene chloride and 5% acetone as the eluant. The fractions were concentrated by evaporation; the residue was dissolved in 100 ml of methanol, and the solution was hydrogenated for 6 hours at 50° C. under a hydrogen pressure of 5 bar in the presence of 0.5 gm of 10% palladium-on-charcoal. After the absorption of hydrogen had ended, the catalyst was removed by suction-filtration; the filtrate was concentrated by evaporation, and the residue was purified on silica gel, using methylene chloride and 5% ethanol as the eluant. The free base product thus obtained was dissolved in acetone, and the dihydrochloride was precipitated with ethereal hydrochloric acid.

Yield: 0.6 gm (53.6% of theory).
Melting point: 222°–224° C. (decomposition).

EXAMPLE 120

1-[1-Hydoroxy-7,8-dimethoxy-1,3,4,5-tetrahydro-2H-3-benzazepin-2-on-3-yl]-3-[N-methyl-N-(2-{3,4-dimethoxyphenyl}-ethyl)-amino]-propane 2.35 gm (5 mmol) of 1-[7,8-dimethoxy-1,3,4,5-tetrahydro-2H-3-benzazepin-1,2-dion-3-yl]-3-[N-methyl-N-(2-{3,4-dimethoxy-phenyl}-ethyl)-amino]-propane were dissolved in a mixture of 100 ml of methanol and 5 ml of water, and then 0.2 gm of sodium borohydride were added in batches to the solution, while stirring. After it had all been added, the mixture was stirred for 15 minutes more; 10 ml of 2 N hyrochloric acid were then added, and the mixture was made alkaline with methanolic ammonia, decolorized with Fuller's earth, filtered and concentrated by evaporation in vacuo. The residue was dissolved in methylene chloride; any undissolved salts were filtered off, and the filtrate was concentrated by evaporation.

Yield: 1.65 gm (69.9% of theory), viscous oil.
IR-spectrum (methylene chloride): 3,400 cm$^{-1}$ (OH), 2,840 cm$^{-1}$ (methoxy), 2,800 cm$^{-1}$ (N-alkyl), 1,660 cm$^{-1}$ (CO).
$C_{26}H_{36}N_2O_6$, (472.59): Calculated: C-66.08%; H-7.68%; N-5.93%; Found: C-65.87%; H-7.75%; N-5.73%.

EXAMPLE 121

1-[7,8-Dimethoxy-1,3-dihydro-2H-3,5-benzodiazepin-3-yl]-3-[N-methyl-N-(2-{3,4-dimethoxy-phenyl}-ethyl)-amino]-propane dihydrochloride 4.3 gm (10 mmols) of N-[2-(2-amino-4,5-dimethoxy-phenyl)-ethyl]-N'-methyl-N'-[2-(3,4-dimethoxy-phenyl)ethyl]-1,3-diamino-propane were refluxed for 18 hours in 30 ml of triethylorthoformate; the reaction solution was then concentrated by evaporation in vacuo, and the residue was purified on silica gel, with methylene chloride plus 3% methanol as the eluant. The free base product thus obtained was dissolved in acetone and the dihydrochloride was precipitated by the addition of ethereal hydrochloric acid.

Yield: 1.6 gm (31.1% of theory).
Melting point: 232°–234° C.

EXAMPLE 122

1-[7,8-Dimethoxy-1,3,4,5-tetrahydro-2H-3-benzazepin-2-on-3-yl]-3-[N-methyl-N-(2-{4-amino-3-nitro-phenyl}-ethyl)-amino]-propane hydrochloride 1.0 gm (1.75 mmols) of 1-[7,8-dimethoxy-1,3,4,5-tetrahydro-2H-3-benzazepin-2-on-3-yl]-3-[N-methyl-N-(2-{4-acetamino-3-nitro-phenyl}-ethyl)-amino]-propane was heated in 50 ml of methanolic hydrochloric acid for 2 hours at 45° to 50° C. The reaction solution was then concentrated by evaporation; the residue was dissolved in methylene chloride; the solution was washed with saturated aqueous sodium bicarbonate and dried over magnesium sulfate, and the solvent was distilled off in vacuo. After the residue had been purified on silica gel with methylene chloride and 5% ethanol as the eluant, the hydrochloride was precipitated from acetone by the addition of ethereal hydrochloric acid.

Yield: 0.4 gm (43.1% of theory).
Melting point: 207°–208° C. (decomp.).

EXAMPLE 123

1-[1-Oximino-7,8-dimethoxy-1,3,4,5-tetrahydro-2H-3-benzazepin-2-on-3-yl]-3-[N-methyl-N-(2-{3,4-dimethoxyphenyl}-ethyl)-amino]-propane hydrochloride A mixture of 3.6 gm of (6.8 mmols) of 1-[7,8-dimethoxy-1,3,4,5-tetrahydro-2H-3-benzazepin-1,2-dion-3-yl]-3-[N-methyl-N-(2-{3,4-dimethoxy-phenyl}-ethyl)-amino]-propane, 0.57 gm of hydroxylamine hydrochloride and 0.87 gm of sodium carbonate was refluxed for 8 hours in 100 ml of ethanol. The solvent was then distilled off in vacuo; the residue was dissolved in water/methylene chloride, and the organic phase was separated, dried over magnesium sulfate and concentrated by evaporation. The residue was purified on silica gel, using methylene chloride and 5% ethanol as the eluant. The free base product thus obtained was dissolved in acetone, and the hydrochloride was precipitated by the addition of ethereal hydrochloric acid.

Yield: 2.4 gm (67.6% of theory).
Melting point: 156°–158° C.

EXAMPLE 124

1-[1-Amino-7,8-dimethoxy-1,3,4,5-tetrahydro-2H-3-benzazepin-2-on-3-yl]-3-[N-methyl-N-(2-{3,4-dimethoxyphenyl}-ethyl)-amino]-propane dihydrochloride 1.6 gm (3.3 mmols) of 1-[1-oximino-7,8-dimethoxy-1,3,4,5-tetrahydro-2H-3-benzazepin-2-on-3-yl]-3-[methyl-N-(2-{3,4-dimethoxy-phenyl}-ethyl)-amino]-propane were added to 150 ml of ethanol; 1.5 ml of 98% hydrazine hydrate and 1 gm of Raney nickel were added, and the mixture was refluxed for 7 hours. In order to complete the reaction, an additional 1.5 ml of 98% hydrazine hydrate and 1 gm of Raney nickel were aded, and the mixture was refluxed for 3 hours more. The catalyst was removed by suction-filtration; the solvent was distilled off in vacuo, and the residue was purified on silica gel with methylene chloride and 10% methanol. The dihydrochloride was precipitated from an acetone solution of the free base by the addition of ethereal hydrochloric acid.

Yield: 0.8 gm (44.6% of theory).
Melting point: 232°–234° C. m/e=471.

EXAMPLE 125

1-[7,8-Dimethoxy-1,3,4,5-tetrahydro-2H-3-benzazepin-2-on-3-yl]-3-[N-methyl-N-(3-{4-dimethylamino-phenyl}-propyl)-amino]-propane dihydrochloride A mixture of 5.7 gm (19.4 mmols) of 1-[7,8-dimethoxy-phenyl-1,3,4,5-tetrahydro-2H-3-benzazepin-2-on-3-yl]-3-N-methyl-amino-propane and 4.7 gm (19.4 mmols) of 3-(4-dimethylamino-phenyl)-propyl bromide was heated at 130° C. for 1¼ hours after the addition of 3.3 ml of ethyldiisopropylamine. The reaction was dissolved in a mixture of chloroform and 25% sodium hydroxide, and the organic phase was separated, washed with water, dried over magnesium sulfate and concentrated by evaporation. After the residue thus obtained had been purified on silica gel with methylene chloride and 5% methanol as the eluant, the dihydrochloride was precipitated from acetone with ethereal hydrochloric acid.

Yield: 0.6 gm (5.9% of theory).
Melting point: 191°–192° C. (decomp.).

EXAMPLE 126

1-[7,8-Dimethoxy-1,3,4,5-tetrahydro-2H-3-benzazepin-2-on-3-yl]-3-[N-methyl-N-(4-dimethylamino-phenyl)-butyl)-amino]-propane hydrobromide This compound was prepared analogous to Example 125 from 1-[7,8 -dimethoxy-phenyl-1,3,4,5-tetrahydro-2H-3-benzazepin-2-on-3-yl]-3-N-methyl-amino-propane and 4-(4-dimethylamino-phenyl)-butyl bromide.

Yield: 10.3% of theory.
Melting point: 116°–118° C.

EXAMPLE 127

1-[1-Hydroxy-7,8-dimethoxy-2,3,4,5-tetrahydro-1H-3-benzazepin-3-yl]-3-[-methyl-N-(2-{3,4-dimethoxyphenyl}-ethyl)-amino]-propane dihydrochloride 2.45 gm (5 mmols) of 1-[7,8-dimethoxy-1,3,4,5-tetrahydro-2H-3-benzazepin-1,2-dion-3-yl]-3-[N-methyl-N-(2-{3,4-dimethoxy-phenyl}-ethyl)-amino]-propane were dissolved in a mixture of 100 ml of ether and 50 ml of tetrahydrofuran, and then 0.76 gm of lithium aluminum hydride were added in batches, while stirring. The resulting mixture was refluxed for one hour, cooled with ice water and mixed with 15% ammonium chloride solution. The hydroxide precipitate was suction-filtered off and washed with ether, and the filtrate was concentrated by evaporation. After the free base product thus obtained had been dissolved in acetone, the dihydrochloride was precipitated with methanolic hydrochloric acid.

Yield: 2.2 gm (82.7% of theory).
Melting point: 210°–212° C.

EXAMPLE 128

1-[7,8-Dimethoxy-1,3,4,5-tetrahydro-2H-3-benzazepin-2-on-3-yl]-3-N-methyl-N-(4-{4-amino-3,5-dibromo-phenyl}-butyl)-amino]-propane hydrobromide A mixture of 1.1 gm (3.6 mmols) of 1-[7,8-dimethoxyphenyl-1,3,4,5-tetrahydro-2H-3-benzazepin-2-on-3-yl]-3-N-methyl-amino-propane and 1.4 gm (3.6 mmols) of 4-(4-amino-3,5-dibromo-phenyl)-butyl bromide was heated at 130° C. for 2 hours in 3 ml of ethyl-diisorpopyl-amine. Then, the excess amine was distilled off in vacuo, and the residue was purified on silica gel, using methylene chloride and 2% ethanol as the eluant. The fractions were combined and evaporated in vacuo; the residue was triturated with acetone, and the precipitate formed thereby was suction-filtered off.

Yield: 0.6 gm (27.9% of theory).
Melting point: 159°-161° C.

EXAMPLE 129

1-[7,8-Dimethoxy-1,3,4,5-tetrahydro-2H-3-benzazepin-2-on-3-yl]-3-[N-methyl-N-(3-{3,4-dimethoxy-phenyl}-propyl)-amino]-propane hydrochloride 2.6 gm (5 mmols) of the sodium salt of N-[3-[N-methyl-N'-(3-{3,4-dimethoxy-phenyl}-propyl)-amino]-propyl]-2-(2-carboxymethyl-4,5-dimethoxy-phenyl)-ethylamine were heated at 200° C. in 30 ml of sulfolane for 2 hours. After cooling, the mixture was diluted with 3 ml of water, and the solution was extracted three times with methylene chloride. The combined organic extracts were washed twice with water, dried over magnesium sulfate, and the solvent was removed by evaporation in vacuo. The residue was dissolved in acetone, and the hydrochloride was precipitated by the addition of methanolic hydrochloric acid.

Yield: 1.8 gm (71% of theory).
Melting point: 220°-221° C.

EXAMPLE 130

1-[7,8-Dimethoxy-1,3,4,5-tetrahydro-2H-3-benzazepin-1,2-dion-3-yl]-3-[N-methyl-N-(3-{3,4-dimethoxy-phenyl}-propyl)-amino]-propane hydrochloride 1.7 gm (0.0154 mmols) of selenium dioxide were added at 70° C. to 70 ml of 1,4-dioxane and 2.8 ml of water. After 15 minutes, 1.4 gm of diatomaceous earth and 6.9 gm (0.0147 mmols) of 1-[7,8-dimethoxy-1,3,4,5-tetrahydro-2H-3-benzazepin-2-on-3-yl]-3-[N-methyl-N-(3-{3,4-dimethoxyphenyl}-propyl)-amino]-propane were added, and the resulting mixture was refluxed for 40 hours. After cooling, the undissolved components were removed by suction-filtration, the filtrate evaporated, and the residue was purified on silica gel with methylene chloride+4% ethanol as the eluant. The free base product was dissolved in acetone, and the hydrochloride was precipitated with ethereal hydrochloric acid.

Yield: 2.36 gm (29.2% of theory).
Melting point: 189°-192° C.

EXAMPLE 131

1-[7,8-Dimethoxy-1,3,4,5-tetrahydro-2H-3-benzazepin-2-on-3-yl]-3-[N-methyl-N-(2-{4-amino-3,5-dichloro-phenyl}-2-hydroxy-ethyl)-amino]-propane This compound was prepared from 1-[7,8-dimethoxy-1,3,4,5-tetrahydro-2H-3-benzazepin-2-on-3-yl]-3-[N-methyl-N-(4-amino-3,5-dichloro-benzoyl-methyl)-amino]-propane and sodium borohydride analogous to Example 118.

Yield: 71.6% of theory.
IR-spectrum (methylene chloride): 3,400 cm$^{-1}$, 3,495 cm$^{-1}$ (NH$_2$), 1,650 cm$^{-1}$ (CO).
UV-spectrum (ethanol): 240 nm (0.14), 290 nm (0.06), 314 nm (shoulder, 0.02).

EXAMPLE 132

1-[7,8-Dimethoxy-1,3,4,5-tetrahydro-2H-3-benzazepin-2-on-3-yl]-3-[N-methyl-N-(2-{2-amino-3,5-dichloro-phenyl}-2-hydroxy-ethyl)-amino]-propane This compound was prepared from 1-[7,8-dimethoxy-1,3,4,5-tetrahydro-2H-3-benzazepin-2-on-3-yl]-3-[N-methyl-N-(2-amino-3,5-dichloro-benzoylmethyl)-amino]-propane and sodium borohydride analogous to Example 118.

Yield: 45% of theory, resin.
IR-spectrum (methylene chloride): 3,360 cm$^{-1}$, 3,450 cm$^{-1}$ (NH$_2$), 1,650 cm$^{-1}$ (lactam-CO).
UV-spectrum (ethanol) 240 nm (0.13), 280-290 nm (0.045), 310 nm (shoulder, 0.03).

EXAMPLE 133

1-[7,8-Dimethoxy-1,3,4,5-tetrahydro-2H-3-benzazepin-2-on-3-yl]-3-[N-methyl-N-(2-{3-amino-4-chloro-phenyl}-2-hydroxy-ethyl)-amino]-propane This compound was prepared from 1-[7,8-dimethoxy-1,3,4,5-tetrahydro-2H-3-benzazepin-2-on-3-yl]-3-[N-methyl-N-(3-amino-4-chloro-benzoyl-methyl)-amino]-propane and sodium borohydride analogous to Example 118.

Yield: 55% of theory, resin.
IR-spectrum (methylene chloride): 3,380 cm$^{-1}$, 3,470 cm$^{-1}$ (NH$_2$), 1,650 cm$^{-1}$ (lactam-CO).
UV-spectrum (ethanol): 236 nm (0.13), 282-292 nm (0.055), 310 nm (shoulder, 0.02).

EXAMPLE 134

1-[7,8-Dimethoxy-1,3,4,5-tetrahydro-2H-3-benzazepin-2-on-3-yl]-3-[N-methyl-N-(2-{4-amino-3-chloro-5-fluorophenyl}-2-hydroxy-ethyl)-amino]-propane This compound was prepared from 1-[7,8-dimethoxy-1,3,4,5-tetrahydro-2H-3-benzazepin-2-on-3-yl]-3-[N-methyl-N-(4-amino-3-chloro-5-fluoro-benzoyl-methyl)-amino]-propane and sodium borohydride analogous to Example 118.

Yield: 48% of theory, foam.
IR-spectrum (methylene chloride): 3,390 cm$^{-1}$, 3,480 cm$^{-1}$ (NH$_2$), 1,645 cm$^{-1}$ (lactam-CO).
UV-spectrum (ethanol): 238 nm (0.18) 282-292 nm (0.07).

EXAMPLE 135

1-[7,8-Dimethoxy-1,3,4,5-tetrahydro-2H-3-benzazepin-2-on-3-yl]-3-[N-methyl-N-(2-{4-amino-3-chloro-5-methylphenyl}-2-hyroxy-ethyl)-amino]-propane This compound was prepared from 1-[7,8-dimethoxy-1,3,4,5-tetrahydro-2H-3-benzazepin-2-on-3-yl]-3-[N-methyl-N-(4-amino-3-chloro-5-methyl-benzoyl-methyl)-amino]-propane and sodium borohydride analogous to Example 118.

Yield: 25% of theory, foam.
IR-spectrum (methylene chloride): 3,380 cm$^{-1}$, 3,470 cm$^{-1}$ (NH$_2$), 1,650 cm$^{-1}$ (lactam-CO).

UV-spectrum (ethanol): 239 nm (0.15), 280–290 nm (0.05), 305 nm (shoulder, 0.01).

The following compounds were prepared by procedures analogous to those described in the preceding examples:

1-[7-Methoxy-1,3,4,5-tetrahyro-2H-3-benzazepin-2-on-3-yl]-3-[N-methyl-N-(3-{3,4-dimethoxy-phenyl}-propyl)-amino]-propane hydrochloride
Melting point: 172°–175° C.

1-[7-Methoxy-1,3,4,5-tetrahydro-2H-3-benzazepin-2-on-3-yl]-3-[N-methyl-N-(3-{4-amino-3,5-dichlorophenyl}-propyl)-amino]-propane;

1-[7-Trifluoromethyl-1,3,4,5-tetrahydro-2H-3-benzazepin-2-on-3-yl]-3-[N-methyl-N-(2-{3,4-dimethoxyphenyl}-ethyl)-amino]-propane, 1-[7-Trifluoromethyl-1,3,4,5-tetrahydro-2H-3-benzazepin-2-on-3-yl]-3-[N-methyl-N-(3-{3,4-dimethoxyphenyl}-propyl)-amino]-propane, 1-[7-Trifluoromethyl-1,3,4,5-tetrahydro-2H-3-benzazepin-2-on-3-yl]-3-[N-methyl-N-(3-{4-amino-3,5-dichlorophenyl}-propyl)-amino]-propane;

1-[7-Methylamino-1,3,4,5-tetrahydro-2H-3-benzazepin-2-on-3-yl]-3-[N-methyl-N-(2-{3,4-dimethoxyphenyl}-ethyl)-amino]-propane, 1-[7-Methylamino-1,3,4,5-tetrahydro-2H-3-benzazepin-2-on-3-yl]-3-[N-methyl-N-(3-{3,4-dimethoxyphenyl}-propyl)-amino]-propane, 1-[7-Methylamino-1,3,4,5-tetrahydro-2H-3-benzazepin-2-on-3-yl]-3-[N-methyl-N-(3-{4-amino-3,5-dichlorophenyl}-propyl)-amino]-propane, 1-[7-Dimethylamino-1,3,4,5-tetrahydro-2H-3-benzazepin-2-on-3-yl]-3-[N-methyl-N-(2-{3,4-dimethoxyphenyl}-ethyl)-amino]-propane,
IR-spectrum (methylene chlorie): 1660 cm$^{-1}$ (CO).

1-[7-Dimethylamino-1,3,4,5-tetrahydro-2H-3-benzazepin-2-on-3-yl]-3-[N-methyl-N-(3-{3,4-dimethoxyphenyl}-propyl)-amino]-propane, 1-[7-Dimethylamino-1,3,4,5-tetrahydro-2H-3-benzazepin-2-on-3-yl]-3-[N-methyl-N-(3-{4-amino-3,5-dichloro-phenyl}-propyl)-amino]-propane, 1-[7,8-Dichloro-1,3,4,5-tetrahydro-2H-3-benzazepin-2-on-3-yl]-3-[N-methyl-N-(2-{3,4-dimethoxyphenyl}-ethyl)-amino]-propane;

1-[7,8-Dichloro-1,3,4,5-tetrahydro-2H-3-benzazepin-2-on-3-yl]-3-[N-methyl-N-(3-{3,4-dimethoxyphenyl}-propyl)-amino]-propane;

1-[7,8-Dichloro-1,3,4,5-tetrahydro-2H-3-benzazepin-2-on-3-yl]-3-[N-methyl-N-(3-{4-amino-3,5-dichlorophenyl}-propyl)-amino]-propane;

1-[7,8-Dimethoxy-1,3,4,5-tetrahydro-2H-3-benzazepin-2-on-3-yl]-3-[N-methyl-N-(2-hydroxy-3-{3,4-dimethoxy-phenyl}-propyl)-amino]-propane, oil, $C_{27}H_{38}N_2O_6$, (486.6); Calc: C-66.64%; H-7.87%; N-5.76%; Found: C-66.61%; H-7.95%; N-5.74%.

1-[7,8-Dimethoxy-1,3,4,5-tetrahydro-2H-3-benzazepin-2-on-3-yl]-3-[N-methyl-(2-hydroxy-3-{4-amino-3,5-dichloro-phenyl}-propyl)-amino]-propane;

1-[7,8-Dimethoxy-1,3,4,5-tetrahydro-2H-3-benzazepin-2-on-3-yl]-3-[N-methyl-(3-hydroxy-3-{4-amino-3,5-dichloro-phenyl}-propyl)-amino]-propane;

1-[7,8-Dimethoxy-1,3,4,5-tetrahydro-2H-3-benzazepin-2-on-3-yl]-3-[N-methyl-(3-hydroxy-3-{3,4-dimethoxy-phenyl}-propyl)-amino]-propane;

1-[7,8-Dimethoxy-1,3,4,5-tetrahydro-2H-3-benzazepin-2-on-3-yl]-3-[N-methyl-(3-{4-amino-3,5-dichloro-phenyl}-propyl)-amino]-propane,
Melting point: 92°–93° C.

1-[1-Hydroxy-7,8-dimethoxy-1,3,4,5-tetrahydro-2H-3-benzazepin-2-on-3-yl]-3-[N-methyl-N-(3-{3,4-dimethoxy-phenyl}-propyl)-amino]-propane;

1-[7-Dimethylamino-8-methoxy-1,3,4,5-tetrahydro-2H-3-benzazepin-2-on-3-yl]-3-[N-methyl-N-(3-{3,4-dimethoxy-phenyl}-propyl)-amino]-propane, 1-[7-Dimethylamino-8-methoxy-1,3,4,5-tetrahydro-2H-3-benzazepin-2-on-3-yl]-3-[N-methyl-N-(2-{3,4-dimethoxy-phenyl}-ethyl)-amino]-propane,
IR-spectrum (methylene chloride): 1650 cm$^{-1}$ (C=O).

1-[7-Bromo-8-methoxy-1,3,4,5-tetrahydro-2H-3-benzazepin-2-on-3-yl]-3-[N-methyl-N-(3-{3,4-dimethoxy-phenyl}-propyl)-amino]-propane, hydrochloride.
Melting point: 198°–199° C. (decomp.).

1-[7-Bromo-8-methoxy-1,3,4,5-tetrahydro-2H-3-benzazepin-2-on-3-yl]-3-[N-methyl-N-(2-{3,4-dimethoxy-phenyl}-ethyl)-amino]-propane,
NMR-spectrum (CDCl$_3$): 7,2 ppm (1H, s, aromat.) 6,6 ppm (1H, s, aromt.), 2,3 ppm (3H, s, N—CH$_3$).

1-[7-Chloro-8-methoxy-1,3,4,5-tetrahydro-2H-3-benzazepin-2-on-3-yl]-3-[N-methyl-N-(3-{3,4-dimethoxy-phenyl}-propyl)-amino]-propane;

1-[7-Chloro-8-methoxy-1,3,4,5-tetrahydro-2H-3-benzazepin-2-on-3-yl]-3-[N-methyl-N-(3-{3,4-dimethoxy-phenyl}-propyl)-amino]-propane;

1-[7,8-Dimethoxy-1,3,4,5-tetrahydro-2H-3-benzazepin-2-on-3-yl]-3-[N-(3-{3,4-dimethoxy-phenyl}-propyl)-amino]-propane,
IR-spectrum (methylene chloride): 1645 cm$^{-1}$ (C=O).

1-[7,8-Dimethoxy-1,3,4,5-tetrahydro-2H-3-benzazepin-2-on-3-yl]-3-[N-(3-{4-amino-3,5-dichloro-phenyl}-propyl)-amino]-propane; and 1-[7,8-Dimethoxy-1,3,4,5-tetrahydro-2H-3-benzazepin-2-on-3-yl]-3-[N-(2-hydroxy-3-{3,4-dimethoxy-phenyl}-propyl)-amino]-propane.

The compounds of the present invention, that is, thos embraced by formula I above and their non-toxic, pharmacologically acceptable acid addition salts, have useful pharmacodynamic properties. More particularly, they exhibit long-lasting bradycardiac activity and reduce the oxygen requirement of the heat, with only slight side effects such as antimuscarinic activity.

The above pharmacological properties were ascertained by the test methods described below, and the results of these tests for a few representative species of the genus and the prior art compound (U) are shown in the tables, where:

A = 1-[7,8-Dimethoxy-1,3,4,5-tetrahydro-2H-3-benzazepin-2-on-3-yl]-3-[N-methyl-N-(2-{3,4-dimethoxy-phenyl}-ethyl)-amino]-propane dihydrochloride, B = 1-[7,8-Dimethoxy-1,3-dihydro-2H-3-benzazepin-2-on-3-yl]-3-[N-methyl-N-(2-{3,4-dimethoxy-phenyl}-ethyl)-amino]-propane hydrochloride, C = 1-[7,8-Dimethoxy-1,3,4,5-tetrahydro-2H-3-benzazepine-1,2-dion-3-yl]-3-[N-methyl-(2-}3,4-dimethoxy-phenyl}-ethyl)-amino]-propane hydrochloride, D = 1-[7,8-Dimethoxy-1,3,4,5-tetrahydro-2H-1,3-benzodiazepin-2-on-3-yl]-3-[N-methyl-(2-{3,4-dimethoxy-phenyl}-ethyl)-amino]-propane, E = 1-[7,8-Dimethoxy-1,3,4,5-tetrahydro-2H-3-benzazepin-2-on-3-yl]-3-[N-(2-{3,4-dimethoxy-phenyl}-ethyl)-amino]-propane hydrochloride, F=1-[7,8-Dimethoxy-1,3,4,5-tetrahydro-2H-3-benzazepin-2-on-3-yl]-3-[N-methyl-N-(2-{4-amino-3,5-dichloro-phenyl}-ethyl)-amino]-propane, G=1-[7,8-Dimethoxy-1,3-dihydro-2H-3-benzazepin-2-on-3-yl]-3-[N-methyl-N-(2-{4-methoxy-phenyl}-ethyl)-amino]-propane hydrochloride, H=1-[7,8-Dimethoxy-1,3,4,5-tetrahydro-2H-3-benzazepin-2-on-3-yl]-3-[N-methyl-N-(2-{4-methoxy-phenyl}-ethyl)-amino]-propane hydrochloride, I=1-[7,8-Methylenedioxy-1,3,4,5-tetrahydro-2H-3-benzazepin-2-on-3-yl]-3-[N-methyl-N-(2-{3,4-dimethoxy-phenyl}-ethyl)]aino]-propane hydrochloride, J=1-[7,8-Dimethoxy-1,3,4,5-tetrahydro-2H-3-benzazepin-2-on-3-yl]-3-[N-allyl-N-(2-{3,4-dimethoxy-phenyl}-ethyl)-amino]-propane hydrochloride, K=1-[7,8-Dimethoxy-1,3-dihydro-2H-3-benzazepin-2-on-3-yl]-3-[N-methyl-N-(2-{3,4-methylenedioxy-phenyl}-ethyl)-amino]-propane hydrochloride, L=1-[7,8-Dimethoxy-1,3,4,5-tetrahydro-2H-3-benzazepin-2-on-3-yl]-3-[N-methyl-N-(3-{3,4-dimethoxy-phenyl}-propyl)-amino]-propane hydrochloride, M=1-[7,8-Dimethoxy-1,3,4,5-tetrahydro-2H-3-benzazepin-2-thion-3-yl]-N-[N-methyl-N-(2-{3,4-dimethoxy-phenyl}-ethyl)-amino]-propane, N=1-[7,8-Dimethoxy-1,3,4,5-tetrahydro-2H-3-benzazepin-2-on-3-yl]-3-[N-methyl-N-(2-hydroxy-2-{3,4-dimethoxyphenyl}-ethyl)-amino]-propane, O=1-[1-Hydroxy-7,8-dimethoxy-1,3,4,5-tetrahydro-2H-3-benzazepin-2-on-3-yl]-3-N-methyl-N-(2-{3,4-dimethoxyphenyl}-ethyl)-amino]-propane, P=1-[7,8-Dimethoxy-1,3,4,5-tetrahydro-2H-3-benzazepin-2-on-3-yl]-3-[N-methyl-N-(2-{4-aino-3-nitrophenyl}-ethyl)-amino]-propane hydrochloride, Q=1-[7,8-Dimethoxy-1,3,4,5-tatrahydro-2H-3-benzazepin-2-on-3-yl]-3-N-methyl-N-(4-{4-dimethylainophenyl}butyl)-amino]-propane hydrobromide, R=1-[7,8-Dimethoxy-1,3,4,5-tetrahydro-2H-3-benzazepin-2-on-3-yl]-3-[N-methyl-N-(2-phenyl-ethyl)-amino]-propane dihydrochloride, S=1-[7,8-Dimethoxy-1,3,4,5-tetrahydro-2H-3-benzazepin-2-on-3-yl]-3-[N-methyl-N-(5-{3,5-dimethoxyphenyl}-pentyl)-amino]-propane, T=1-[7,8-Dimethoxy-1,3,4,5-tetrahydro-2H-3-benzazepin-2-on-3-yl]-3-[N-methyl-N-(3-{4-amino-3,5-dichlorophenyl}-propyl)-amino]-propane, and U=1-[7,8-Dimethoxy-1,3,4,5-tetrahydro-5H-2-benzazepin-1-on-2-yl]-3-[N-methyl-N-(2-{3,4-dimethoxyphenyl}-ethyl)-amino]-propane hydrochloride.

1. Effect on heart rate in cats

The effect of the test compounds on the heart rate was investigated for each dose on seven cats of both sexes with an average weight of 2.5 to 3.5 kg. The cats were anesthetized with Nembutal (30 mg/kg i.p.) and chloralose urethane (40 mg/ml of chloralose+200 mg/ml of urethane, as required). The compound to be tested was injected in aqueous solution into the vena saphena or into the duodenum.

The heart rate was recorded before and after the admiministration of the substance by means of a Grass tachograph from the electrocardiagram (taken from and chest wall) on a Grass polygraph.

The following table shows the results obtained:

TABLE I

| Compound | Dose mg/kg | Reduction in Heart Rate | Half-life (minutes) |
|---|---|---|---|
| A | 1.0 i.v. | −55% | 120 |
| B | 1.0 i.v. | −45% | 120 |
| C | 1.0 i.v. | −44% | 90 |
| D | 1.0 i.v. | −41% | 80 |
| E | 1.0 i.v. | −45% | 90 |
| F | 1.0 i.v. | −51% | 120 |
| U | 1.0 i.v. | −8.2% | 13 |

2. Effect on heart rate in rats

The effect of the test substances on heart rate was investigated in two rats with an average weight of 250 to 300 gm for each dose. The rats were anesthetized with pentobarbital (50 mg/kg i.p. and 20 mg/kg s.c.). The test substances were injected in aqueous solution into the jugular vein (0.1 ml/100 gm).

The blood pressure was measured using a cannula inserted in a carotid artery and the heart rate was recorded from an ECG (IInd or IIIrd reading) obtained using needle electrodes. The heart rate of the animals in the control period was between 350 and 400 beats per minute (b/min).

The following table contains the values found:

TABLE II

| Compound | Dose [mg/kg] | Reduction in Heart Rate (20 Minutes) After Application of the Compound [Beats/Minutes] |
|---|---|---|
| L | 5.0 i.v. | −183 |
|   | 2.5 i.v. | −85 |
|   | 1.0 i.v. | −51 |
| M | 5.0 i.v. | −255 |
|   | 2.5 i.v. | −134 |
|   | 1.0 i.v. | −73 |
| N | 5.0 i.v. | −173 |
|   | 2.5 i.v. | −137 |
| O | 5.0 i.v. | −117 |
|   | 2.5 i.v. | −73 |
|   | 1.0 i.v. | −83 |
| P | 5.0 i.v. | −130 |
| Q | 5.0 i.v. | −123 |
|   | 2.5 i.v. | −91 |
|   | 1.0 i.v. | −94 |
| R | 5.0 i.v. | −135 |
|   | 2.5 i.v. | −110 |
|   | 1.0 i.v. | −80 |
| S | 5.0 i.v. | −18 |
| T | 5.0 i.v. | −175 |
| U | 5.0 i.v. | −18 |

3. Effect on heart rate in guinea pig auricles

Isolated, spontaneously beating auricles from guinea pigs of both sexes, with a body weight of 300 to 400 gm, were tested in tyrode solution in a organ bath. The nutrient solution was supplied with Carbogen (95% $O_2$+5% $CO_2$) and kept at a constant temperature of 30° C. The contractions were recorded isometrically by means of a wire strain gauge on a Grass polygraph. The compounds to be tested were added to the organ bath in various concentrations.

From the maximum dose-activity, curves were prepared, and from them the concentration was determined which reduced the heart rate by 30% (=$EC_{60_{30}}$).

The following table shows the results obtained:

TABLE III

| Substance | EC.$60_{30}$ [g/ml] |
|---|---|
| A | 0.30 |
| C | 0.97 |
| D | 0.58 |
| E | 0.066 |
| F | 0.014 |
| G | 0.014 |
| H | 0.0079 |
| I | 0.063 |
| J | 0.050 |
| K | 0.14 |

4. Acute toxicity:

The acute toxicity of the test compound was determined in mice (observation period: 14 days) after intravenous and peroral administration:

TABLE IV

| Substance | Toxicity (LD$_{50}$) |
|---|---|
| A | 89 mg/kg i.v. |
|   | 1,350 mg/kg p.o. |

The other compounds B to R show no toxic side effects in mice up to a dosage unit of 20 mg/kg i.v.

In view of their pharmacological properties, the compounds of the invention are useful for the treatment of sinus tachycardia of various origins and for the prophylaxis and therapy of ischaemic cardiac disease.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.03 to 0.4 mgm/kg body weight, preferably 0.07 to 0.25 mgm/kg body weight.

The following examples illustrate a few pharmaceutical dosage unit compositions comprising a compound of the present invention as an active ingredient and represent the best modes contemplated of using the invention. The parts are parts by weight unless otherwise specified.

EXAMPLE 136

Tablets containing 10 mg of
1-[7,8-dimethoxy-1,3,4,5-tetrahydro-2H-3-benzazepin-2-on-yl]-3-[N-methyl-N-(2-{3,4-dimethoxy-phenyl}-ethyl)-amino]-propane hydrochloride The tablet composition was compounded from the following ingredients:

| | |
|---|---|
| Actice ingredient | 10.0 parts |
| Corn starch | 57.0 parts |
| Lactose | 48.0 parts |
| Polyvinyl pyrrolidone | 4.0 parts |
| Magnesium stearate | 1.0 parts |
| | 120.0 parts |

Method of preparation

The active ingredient, corn starch, lactose and polyvinyl pyrrolidone were mixed together and moistened with water. The moist mixture was granulated through a screen with a mesh size of 1.5 mm and then dried at about 45° C. The dry granulate was passed through a screen with a mesh size of 1.0 mm and then mixed with magnesium stearate. The finished mixture was compressed in a tablet press into 120 mg-tablets.

EXAMPLE 137

Coated tablets containing 5 mg of
1-[7,8-dimethoxy-1,3,4,5-tetrahydro-2H-3-benzazepin-2-on-yl]-3-[N-methyl-N-(2-{3,4,dimethoxh-phenyl}-ethyl)-amino]-propane hydrochloride The tablet core composition was compounded from the following ingredients:

| | |
|---|---|
| Active ingredient | 5.0 parts |
| Corn starch | 41.5 parts |
| Lactose | 30.0 parts |
| Polyvinyl pyrrolidone | 3.0 parts |
| Magnesium stearate | 0.5 parts |
| | 80.0 parts |

Method of preparation

The active ingredient, corn starch, lactose and polyvinyl pyrrolidone were thoroughly mixed and moistened with water. The moist mass was granulated through a screen with a mesh size of 1 mm, then dried at about 45° C., and the dry granulate was then passed through the same screen. After the addition of magnesium stearate, convex 80 mg-tablet cores were produced by compression in a tablet-making machine. The tablet cores thus produced were coated in known manner with a covering consisting essentially of sugar and talcum. The finished coated tablets were polished with wax.

EXAMPLE 138

Hypodermic solution containing 5 mg of
1-[7,8-dimethoxy-1,3,4,5-tetrahydro-2H-3-benzazepin-2-on-3-yl]-3-[N-methyl-N-(2-{3,4-dimethoxy-phenyl}-ethyl)-amino]-propane hydrochloride The solution was compounded from the following ingredients:
Active ingredient: 5.0 parts
Sorbitol: 50.0 parts
Water for injection ad: 2,000.0 parts by vol.

Method of preparation

In a suitable container, the active ingredient was dissolved in water for injection purposes, and the solution was made isotonic with sorbitol. After being filtered through a membrane filter, the solution was filled into clean, sterilized 2 cc-ampules in an N$_2$-atmosphere and autoclaved for 20 minutes in a current of steam.

EXAMPLE 139

Suppositories containing 15 mg of
1-[1,7,8-dimethoxy-1,3,4,5-tetrahydro-2H-3-benzazepin-2-on-3-yl]-3-[N-methyl-N-(2-{3,4-dimethoxy-phenyl}-ethyl)-aino]-propane hydrochloride The suppositories were compounded from the following ingredients:

| | |
|---|---|
| Active ingredient | 0.015 parts |

| | |
|---|---|
| -continued | |
| Suppository base (e.g. cocoa butter) | 1,685 parts |
| | 1,700 parts |

Method of preparation

The suppository base was melted. At 38° C. the finely divided active ingredient was homogeneously dispersed in the melt, which was then cooled to 35° C. and poured into cooled suppository molds.

EXAMPLE 140

Drop solution containing 10 mg of 1-[7,8-dimethoxy-1,3,4,5-tetrahydro-2H-3-benzazepin-2-on-3-yl]-3-[N-methyl-N-(2-{3,4-dimethoxy-phenyl}-ethyl)-amino]-propane hydrochloride per 5 ml The solution was compounded from the following ingredients:
Active ingredient: 0.2 parts
Hydroxyethyl cellulose: 0.15 parts
Tartaric acid: 0.1 parts
Sorbitol solution containing 70% dry matter: 30.0 parts
Glycerin: 10.0 parts
Benzoic acid: 0.15 parts
Distilled water ad: 100.0 parts by vol.

Method of preparation

The distilled water was heated to 70° C. The hydroxyethyl cellulose, benzoic acid and tartaric acid were dissolved therein while stirring. The mixture was cooled to room temperature, and the glycerin and sorbitol solution were added while stirring. At room temperature, the active ingredient was added and stirred until completely dissolved. Then the mixture was evacuated, while stirring, in order to eliminate air from the liquid.

Any one of the other compounds embraced by formula I or a non-toxic, pharmacologically acceptable acid addition salt thereof may be substituted for the particular ingredient in Examples 136 through 140. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain spcific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

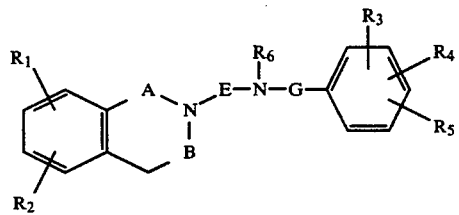

wherein

A is —CH$_2$—CH$_2$—, —CH=CH—, —NH—CO, —CH$_2$CO— or

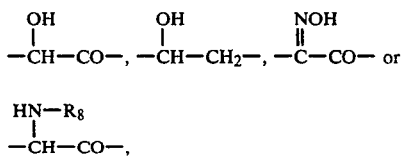

where R$_7$ is alkyl of 1 to 3 carbon atoms, and B is methylene, carbonyl or thiocarbonyl; or
A is —CO—CO—, —N=CH—, $$-\overset{OH}{\underset{|}{CH}}-CO-, \quad -\overset{OH}{\underset{|}{CH}}-CH_2-, \quad -\overset{NOH}{\underset{\|}{C}}-CO- \text{ or}$$

$$-\overset{HN-R_8}{\underset{|}{CH}}-CO-,$$

where R$_8$ is hydrogen or alkyl of 1 to 3 carbon atoms substituted by a phenyl, methoxyphenyl or dimethoxyphenyl, and B is methylene;
E is n-alkylene of 2 to 4 carbon atoms optionally substituted by an alkyl of 1 to 3 carbon atoms, 2-hydroxy-n-propylene, 2-hydroxy-n-butylene or 3-hydroxy-n-butylene;
G is n-alkylene of 1 to 5 carbon atoms optionally substituted by an alkyl of 1 to 3 carbon atoms, wherein one methylene group of an n-alkylene of 2 to 5 carbon atoms can be replaced by a carbonyl group, with the proviso that B is methylene or carbonyl; or methylene-n-hydroxy-alkylene of 1 to 4 carbon atoms, where the methylene group is attached to the nitrogen atom;
R$_1$ is hydrogen, fluorine, chlorine, bromine, trifluoromethyl, amino, hydroxyl, alkyl of 1 to 3 carbon atoms, alkoxy of 1 to 3 carbon atoms, phenyl(alkoxy of 1 to 3 carbon atoms), (alkyl of 1 to 3 carbon atoms)amino or di(alkyl of 1 to 3 carbon atoms)amino;
R$_2$ is hydrogen, fluorine, chlorine, bromine, hydroxyl, alkyl of 1 to 3 carbon atoms, alkoxy of 1 to 3 carbon atoms or phenyl(alkoxy of 1 to 3 carbon atoms); or
R$_1$ and R$_2$, together with each other, are alkylene of 1 to 2 carbon atoms)dioxy;
R$_3$ is hydrogen, fluorine, chlorine, bromine, hydroxy, cyano, nitro, trifluoromethyl, alkyl of 1 to 4 carbon atoms or alkoxy of 1 to 4 carbon atoms;
R$_4$ is hydrogen, alkyl of 1 to 3 carbon atoms, hydroxy, alkoxy of 1 to 3 carbon atoms, amino, (alkyl of 1 to 3 carbon atoms)amino, di(alkyl of 1 to 3 carbon atoms)amino, (alkanoyl of 1 to 3 carbon atoms)amino, (alkoxy of 1 to 3 carbon atoms)carbonylamino, bis[(alkoxy of 1 to 3 carbon atoms)carbonyl]amino, (trifluoromethyl-methyl)amino or (trifluoromethyl-ethyl)-amino; or
R$_3$ and R$_4$, together with each other, are (alkylene of 1 to 2 carbon atoms)dioxy;
R$_5$ is hydrogen, chlorine, bromine, cyano, hydroxy, alkyl or alkoxy, where each alkyl moiety may contain 1 to 4 carbon atoms; and
R$_6$ is hydrogen, alkyl of 1 to 3 carbon atoms, phenyl(alkyl of 1 to 3 carbon atoms), alkanoyl of 1 to 3 carbon atoms, (alkoxy of 1 to 3 carbon atoms)carbonyl or alkenyl of 3 to 5 carbon atoms;
or a non-toxic, pharmacologically acceptable acid addition salt thereof.

2. A compound of claim 1,
where
A is —CH$_2$CH$_2$—, —CH=CH—,

—NH—CO—, —CH$_2$—CO— or —C(CH$_3$)=N— and
B is methylene, carbonyl or thiocarbonyl; or

—N=CH—, —CH(OH)—CH$_2$—, —CH(OH)—CO—, —C(=NOH)—CO—,

—CH(NH$_2$)—CO— or —CH(NH—CH$_2$—CH$_2$—Ar)—CO— (where Ar = 3,4-dimethoxyphenyl)

A is —CO—CO—,

—N=CH—, —CH(OH)—CH$_2$—, —CH(OH)—CO—, —C(=NOH)—CO—,

—CH(NH$_2$)—CO— or —CH(NH—CH$_2$—CH$_2$—Ar)—CO—

B is methylene;
E is ethylene, n-propylene, n-butylene, 2-methyl-n-propylene or 2-hydroxy-n-propylene;
G is methylenecarbonyl, with the proviso that B represents a methylene or carbonyl group; n-alkylene of 1 to 5 carbon atoms or methylene-n-hydroxyalkylene of 1 to 2 carbon atoms, where the methylene group is attached to the nitrogen atom;
R$_1$ is hydrogen, chlorine, bromine, trifluoromethyl, methyl, hydroxyl, benzyloxy, alkoxy of 1 to 3 carbon atoms, amino, methylaino or dimethylamino;
R$_2$ is hydrogen, chlorine, bromine, methyl, hydroxyl or methoxy; or
R$_1$ and R$_2$, together with each other, are methylenedioxy;
R$_3$ is hydrogen, fluorine, chlorine, bromine, trifluoromethyl, nitro, cyano, alkyl of 1 to 4 carbon atoms or alkoxy of 1 to 4 carbon atoms;
R$_4$ is hydrogen, methoxy, amino, methylamino, dimethylamino, acetylamino, ethoxycarbonylamino, bis(ethoxycarbonyl)amino or β,β,β-trifluoroethylamino; or
R$_3$ and R$_4$, together with each other, are methylenedioxy;
R$_5$ is hydrogen, chlorine, bromine, methyl or methoxy; and
R$_6$ is hydrogen, alkyl of 1 to 3 carbon atoms, benzyl, allyl, acetyl or ethoxycarbonyl;
or a non-toxic, pharmacologically acceptable acid addition salt thereof.

3. A compound of claim 1,
where
A is —CH$_2$—CH$_2$—, —CH=CH— or

—C(CH$_3$)=N— and B is carbonyl or thiocarbonyl; or
A is —CH=CH—,

—NH—CO—, —CH(OH)—CO— or —CO—CO— and
B is methylene;
E is n-propylene;
G. is n-akylene of 2 to 5 carbon atoms, —CH$_2$—CH(OH)—, or —CH$_2$—CH$_2$—CH(OH)—;

R$_1$ is hydroxy, methoxy, amino, methylamino or dimethylamino;
R$_2$ is hydrogen or methoxy, or
R$_1$ and R$_2$, together with each other, are methylenedioxy;
R$_3$ is hydrogen, fluorine, chlorine, bromine, trifluoromethyl, methyl, methoxy or nitro;
R$_4$ is hydrogen, methoxy, amino or dimethylamine, or
R$_3$ and R$_4$, together with each other, are methylenedioxy;
R$_5$ is hydrogen, chlorine or bromine; and
R$_6$ is hydrogen, methyl, ethyl, n-propyl or allyl;
or a non-toxic, pharmacologically acceptable acid addition salt thereof.

4. A compound of claim 1, which is of the formula

[Structure: R$_1$, R$_2$-substituted phenyl—A—N(B)—CH$_2$CH$_2$CH$_2$—N(R$_6$)—G—phenyl-R$_3$,R$_4$,R$_5$]

wherein
A is —CH$_2$—CH$_2$— or —CH=CH— and B is carbonyl or thiocarbonyl; or
A is

—NH—CO—, —CH(OH)—CO— or —CO—CO— and B is methylene;
R$_1$ is methoxy, amino, methylamino or dimethylamino,
R$_2$ is hydrogen or methoxy, or
R$_1$ and R$_2$, together with each other, are methylenedioxy;
R$_3$ is hydrogen, fluorine, chlorine, bromine, methoxy or trifluoromethyl or nitro;
R$_4$ is hydrogen, methoxy, amino, methylamino or dimethylamino, or chlorine, when R$_6$ is hydrogen, or
R$_3$ and R$_4$, together with each other, are methylenedioxy;
R$_5$ is hydrogen, chlorine or bromine;

R₆ is hydrogen, methyl or allyl, and
G is n-alkylene of 2 to 5 carbon atoms or

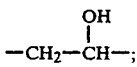

or a non-toxic, pharmacologically acceptable acid addition salt thereof.

5. A compound of claim 3, where
A is —CH₂CH₂— and
B is carbonyl or thiocarbonyl, or
A is

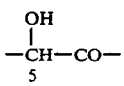

and
B is methylene;
R₁ and R₂ are each methoxy, or R₁ and R₂ are methylenedioxy;
R₃ is hydrogen, chlorine or bromine or methoxy;
R₄ is methoxy, amino or dimethylamino;
R₅ is hydrogen or chlorine;
R₆ is methyl, and
G is n-alkylene of 2 to 5 carbon atoms or a

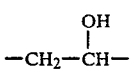

group,
or a non-toxic, pharmacologically acceptable addition salt thereof.

6. A compound of claim 1, which is 1-[7,8-dimethoxy-1,3,4,5-tetrahydro-2H-3-benzazepin-2-on-3-yl]-3-[N-methyl-N-(2-{3,4-dimethoxy-phenyl}-ethyl)-amino]-propane or a non-toxic, pharmacologically acceptable acid addition salt thereof.

7. A compound of claim 1, which is 1-[7,8-dimethoxy-1,3,4,5-tetrahydro-2H-3-benzazepin-1,2-dione-3-yl]-3-[N-methyl-N-(2-{3,4-dimethoxy-phenyl}-ethyl)-amino]-propane or a non-toxic, pharmacologically acceptable acid addition salt thereof.

8. A compound of claim 1, which is 1-[7,8-dimethoxy-1,3,4,5-tetrahydro-2H-3-benzazepin-2-on-3-yl[-3-[N-methyl-N-(2-{4-amino-3,5-dichloro-phenyl}-ethyl)-amino]-propane or a non-toxic, pharmacologically acceptable acid addition salt thereof.

9. A compound of claim 1, which is 1-[7,8-dimethoxy-1,3,4,5-tetrahydro-2H-3-benzazepin-2-on-3-yl]-3-[N-methyl-N-(2-{4-methoxy-phenyl}-ethyl)-amino]-propane or a non-toxic, pharmacologically acceptable acid addition salt thereof.

10. A compound of claim 1, which is 1-[7,8-dimethoxy-1,3,4,5-tetrahydro-2H-3-benzazepin-2-on-3-yl]-3-[N-methyl-N-(3-{3,4-dimethoxy-phenyl}-propyl)-amino]-propane or a non-toxic, pharmacologically acceptable acid addition salt thereof.

11. A compound of claim 1, which is 1-1-hydroxy-7,8-dimethoxy-1,3,4,5-tetrahydro-2H-3-benzazepin-2-on-3yl]-3-[N-methyl-N-(3-{3,4-dimethoxy-phenyl}-propyl)amino]-propane or a non-toxic, pharmacologically acceptable acid addition salt thereof.

12. A compound of claim 1, which is 1-[7,8-dimethoxy-1,3,4,5-tetrahydro-2H-3-benzazepin-2-on-3-yl[-3-[N-methyl-N-(3-{4-amino-3,5-dichloro-phenyl}-propyl)amino]-propane or a non-toxic, pharmacologically acceptable acid addition salt thereof.

13. A bradycardiac pharmaceutical composition consisting essentially of an inert pharmaceutical carrier and an effective bradycardiac amount of a compound of claim 1.

14. The method of lowering the heart rate of a warm-blooded animal in need thereof, which comprises per-orally, parenterally or rectally administering to said animal an effective bradycardiac amount of a compound of claim 1.

* * * * *

UNITED STATES PATENT AND TRADEMARK OFFICE
CERTIFICATE OF CORRECTION

PATENT NO. : 4,490,369

DATED : December 25, 1984

INVENTOR(S) : MANFRED REIFFEN ET AL.

It is certified that error appears in the above-identified patent and that said Letters Patent is hereby corrected as shown below:

Column 8, line 12, "eraby" should read -- erably --.

Column 8, line 23, "of" should read -- or --.

Column 8, line 31, "hyro" should read -- hydro --.

Column 8, line 37, "preferaboy" should read -- preferably --.

Column 9, line 63, "$R_3$ and $R_5$" should read -- $R_3$ to $R_5$ --.

Column 10, line 66, "crrried" should read -- carried --.

Column 11, line 46, "an" should read -- and --.

Column 12, line 36, "an" should read -- and --.

Column 13, line 27, "of" should read -- or --.

UNITED STATES PATENT AND TRADEMARK OFFICE
CERTIFICATE OF CORRECTION

PATENT NO.  : 4,490,369
DATED       : December 25, 1984
INVENTOR(S) : MANFRED REIFFEN ET AL.

It is certified that error appears in the above-identified patent and that said Letters Patent is hereby corrected as shown below:

Column 13, line 34, "slat" should read -- salt --.

Column 13, line 61, "efined" should read -- defined --.

Column 15, line 21, "an" should read -- and --.

Column 15, line 23, "1 1 to 4" should read -- 1 to 4 --.

Column 15, line 35, "of" should read -- or --.

Column 15, line 42, "pallladi" should read -- palladi --.

Column 15, line 45, "suitabe" should read -- suitable --.

Column 15, line 51, "compond" should read -- compound --.

Column 15, line 54, "reating" should read -- reacting --.

Column 15, line 64, "an" should read -- and --.

Column 18, line 4, "N'" should read -- N,N' --.

UNITED STATES PATENT AND TRADEMARK OFFICE
CERTIFICATE OF CORRECTION

PATENT NO. : 4,490,369
DATED : December 25, 1984
INVENTOR(S) : MANFRED REIFFEN ET AL.

It is certified that error appears in the above-identified patent and that said Letters Patent is hereby corrected as shown below:

Column 24, line 58, "2-on-3-N" should read -- 2-on-3-yl)-3-N --.

Column 24, line 64, "-1,3-dimethoxy" should be deleted.

Column 25, line 63, "64.5 gm   2.03 ml" should read
   -- 64.5 gm ≙ 2.03 ml --.

Column 26, line 14, "(7-Bromo" should read -- 1-(7-Bromo --.

Column 27, line 12, "[N-methyl" should read
   -- yl]-3-[N-methyl --.

Column 27, line 16, "(0.0006 mol)" should read -- (0.006 mol) --.

Column 31, line 65, "cyanoboronhydride" should read
   -- cyanoborohydride --.

Column 31, line 67, "dimethoxyl" should read -- dimethoxy --.

Column 33, line 8, "[3-(4,8" should read -- [3-(7,8 --.

UNITED STATES PATENT AND TRADEMARK OFFICE
CERTIFICATE OF CORRECTION

PATENT NO. : 4,480,369

DATED : December 25, 1984

INVENTOR(S) : MANFRED REIFFEN ET AL.

It is certified that error appears in the above-identified patent and that said Letters Patent is hereby corrected as shown below:

Column 37, line 2, "(3,5" should read -- (3,4 --.

Column 37, line 13, "(3,5" should read -- (3,4 --.

Column 39, line 42, "(14$" should read -- (14% --.

Column 39, line 62, "rooom" should read -- room --.

Column 40, line 3, "b 2.9 gm" should read -- 2.9 gm --.

Column 45, line 29, "an" should read -- and --.

Column 47, line 13, "2-1" should read -- 2- --.

Column 48, line 41, "aquoeus" should read -- aqueous --.

Column 50, line 65, "3-8 N" should read -- 3-[N --.

Column 56, line 24, "amino}" should read -- amino] --.

Column 58, line 43, "Hydoroxy" should read -- Hydroxy --.

UNITED STATES PATENT AND TRADEMARK OFFICE
CERTIFICATE OF CORRECTION

PATENT NO. : 4,490,369
DATED : December 25, 1984
INVENTOR(S) : MANFRED REIFFEN ET AL.

It is certified that error appears in the above-identified patent and that said Letters Patent is hereby corrected as shown below:

Column 60, line 4, "aded" should read -- added --.

Column 63, line 60, "[N-methyl-" should read
 -- [N-methyl-N- --.

Column 63, line 63, "[N-methyl-" should read
 -- [N-methyl-N- --.

Column 63, line 66, "[N-methyl-" should read
 -- [N-methyl-N- --.

Column 64, line 22, "aromt." should read -- aromat. --.

Column 64, line 40, "thos" should read -- those --.

Column 64, line 46, "heat" should read -- heart --.

Column 65, line 13, "aino]" should read -- amino] --.

Column 65, line 35, "aino" should read -- amino --.

Column 65, line 37, "tatrahydro" should read -- tetrahydro --.

UNITED STATES PATENT AND TRADEMARK OFFICE
CERTIFICATE OF CORRECTION

PATENT NO. : 4,490,369
DATED : December 25, 1984
INVENTOR(S) : MANFRED REIFFEN ET AL.

It is certified that error appears in the above-identified patent and that said Letters Patent is hereby corrected as shown below:

Column 65, line 38, "dimethylaino" should read
  -- dimethylamino --.

Column 65, line 66, "and" should read -- the --.

Column 68, line 63, "aino" should read -- amino --.

Column 70, line 45, "alkylene" should read -- (alkylene --.

Column 70, line 63, "pheny-" should read -- phenyl --.

Column 70, line 64, "l(alkyl" should read -- -(alkyl --.

UNITED STATES PATENT AND TRADEMARK OFFICE
CERTIFICATE OF CORRECTION

PATENT NO. : 4,490,369

DATED : December 25, 1984

INVENTOR(S) : MANFRED REIFFEN ET AL.

It is certified that error appears in the above-identified patent and that said Letters Patent is hereby corrected as shown below:

Column 71, lines 12-22, delete.

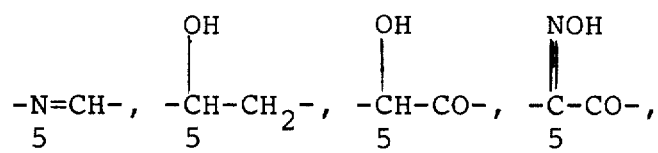

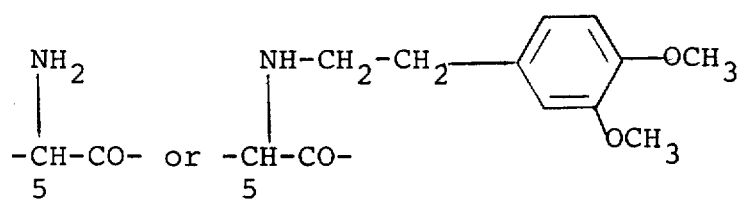

Column 71, line 35, insert -- and --.

Column 71, line 46, "methylaino" should read -- methylamino --.

Signed and Sealed this

Eighth Day of October 1985

[SEAL]

Attest:

DONALD J. QUIGG

Attesting Officer

Commissioner of Patents and Trademarks—Designate